US005608063A

United States Patent [19]

Hobbs, Jr. et al.

[11] Patent Number: 5,608,063
[45] Date of Patent: *Mar. 4, 1997

[54] METHOD, SYSTEM AND REAGENTS FOR DNA SEQUENCING

[75] Inventors: Frank W. Hobbs, Jr., Wilmington, Del.; George L. Trainor, Glen Mills, Pa.

[73] Assignee: E. I. Du Pont de Nemours and Company, Wilmington, Del.

[*] Notice: The term of this patent shall not extend beyond the expiration date of Pat. No. 5,047,519.

[21] Appl. No.: 412,409

[22] Filed: Mar. 28, 1995

Related U.S. Application Data

[63] Continuation of Ser. No. 181,358, Jan. 13, 1994, abandoned, which is a continuation of Ser. No. 981,148, Nov. 24, 1992, abandoned, which is a division of Ser. No. 780,346, Oct. 22, 1991, Pat. No. 5,242,796, which is a division of Ser. No. 57,566, Jun. 12, 1987, abandoned, which is a continuation-in-part of Ser. No. 881,372, Jul. 2, 1986, abandoned.

[51] Int. Cl.$^6$ .......................... C07F 9/6512; C07F 9/6561
[52] U.S. Cl. ............................................. 544/244; 544/243
[58] Field of Search ..................................... 544/243, 244

[56] References Cited

U.S. PATENT DOCUMENTS

| 4,711,955 | 12/1987 | Ward et al. | 536/29 |
|---|---|---|---|
| 5,013,644 | 5/1991 | Severson et al. | 435/6 |
| 5,047,519 | 9/1991 | Hobbs, Jr. et al. | 536/23 |
| 5,093,232 | 3/1992 | Urdea et al. | 435/6 |
| 5,151,507 | 9/1992 | Hobbs, Jr. et al. | 544/243 |

FOREIGN PATENT DOCUMENTS

| 252683 | 1/1988 | European Pat. Off. |
|---|---|---|
| 251786 | 1/1988 | European Pat. Off. |
| 3446635 | 12/1984 | Germany. |
| 3501306 | 1/1985 | Germany. |
| 60-242368 | 12/1985 | Japan. |
| 61-109797 | 5/1986 | Japan. |
| 8403285 | 8/1984 | WIPO. |
| 8602929 | 5/1986 | WIPO. |

OTHER PUBLICATIONS

A. M. Maxam et al, Methods in Enzym., Sequencing End-Labeled DNA with Base-Specific Chemical Cleavages', 1980, vol. 65, pp. 499–559.
F. Sanger et al., Proc. Nat. Acad. Sci., DNA Sequencing with chain-terminating inhibitors, Oct. 3, 1977, vol. 74, pp. 5463–5467.
Lloyd M. Smith et al., Nucleic Acids Research, vol. 13, Mar. 19, 1985, pp. 2399–2412.
Naimski et al., 1980, vol. 106, Anal. Biochem., pp. 471–475.
Chidgeavadge, Z. G. et al, Nucl. Acids. Res., vol. 12, pp. 1671–1686, 1984.
Krayevsky A. et al. Nucl. Acids. Res., Symp. Series No. 14,283, 1984, pp. 283–284.
Robert S. Beabealashvilli et al., Biochim. Biophys. Acta., vol. 868, 1986, pp. 136–144.
Zurab G. Chidgeavadze et al., Biochim Biophys. Acta, 1986, pp. 145–162, vol. 868.
Bergstrom et al., J. Am. Chem. Soc., vol. 98, pp. 1587, 1976.
Langer et al., Proc. Natl. Acad. Sci. USA, vol. 78, No. 11, pp. 6633–6637, 1981.
Draper, Nucleic Acids Research, vol. 12, No. 2, 989–1002 (1984).
Barr et al., J. Chem. Soc., Perkins Trans. I, 1263–1267 (1978).
Bergstrom et. al., J. Am. Chem. Soc., vol. 100, 8106, (1978).
Vincent et al., Tetrahedron Letters, vol. 22, 945–947 (1981).
Robins et al., J. Org. Chem., vol. 48, 1854–1862 (1983).
Sonogashira et al., Tetragedron Letters, No. 50, 4467–4470 (1975).
Edo et al., Chem. Pharm. Bull., vol. 26, No. 12, 3843–3850 (1978).
Seela, et al., Chem. Ber. vol. 111, 2925–2930 (1978).
Schram et al., J. Carbohydrates, Nucleosides and Nucleotides, vol. 2, No. 2, 177–184 (1975).
Bergstrom et al., J. Org. Chem., vol. 46, No. 7, 1423–1431 (1981).
Bergstrom et al., Nucleic Acids Research, vol. 8, 6213–6219 (1980).
Haralambidis et al., Nucleic Acids Research, vol. 15, No. 12, 4857–4876 (1987).
Gibson et al., Nucleic Acids Research, vol. 15, No. 16, 6455–6467 (1987).

*Primary Examiner*—Emily Bernhardt

[57] ABSTRACT

A DNA sequencing system and method are described to detect the presence of radiant energy emitted from different excited reporter dye-labeled species (DNA fragments) following separation in time and/or space, and the identity of the species which emit radiant energy closely spaced in wavelength. Functions of the emitted energy are obtained which vary over the wavelengths of the closely spaced spectra in different senses and the functions ratioed, whereby the ratio is indicative of the identity of the DNA fragments.

The emitting portion of the reporter-labeled DNA fragment is preferably one of a family of fluorescent dyes based on 9-carboxyethyl-6-hydroxy-3-oxo-3H-xanthene. These xanthene dyes are covalently attached to the DNA fragments through the carboxylic acid functionality, preferably via an amide linkage. The dyes may be protected by including an alkoxy group at the 9-position. A spacer may be inserted between the dye and the amine. The fluorescent dye preferably is attached to the DNA chain terminators and provides many advantages. Thus only DNA sequencing fragments resulting from bona fide termination events will carry a reporter. The DNA sequencing may also be labeled using the xanthene dyes which have general utility as fluorescent labels. Also acyclonucleoside triphosphates are described as being useful as chain terminators in DNA sequencing using a modification of the Sanger method.

3 Claims, 8 Drawing Sheets

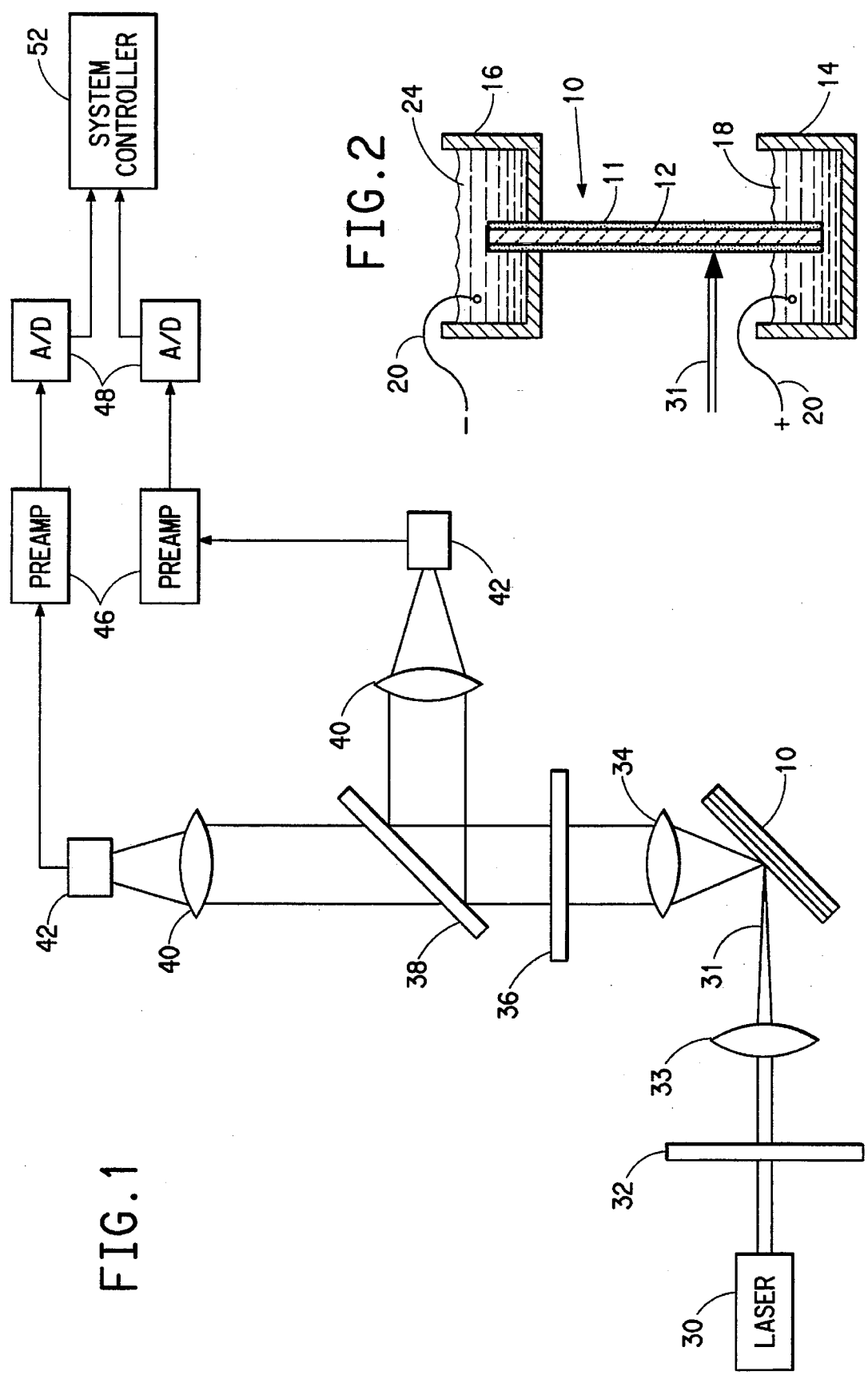

METHOD, SYSTEM AND REAGENTS FOR DNA SEQUENCING

This application is a continuation of Ser. No. 181,358, filed Jan. 13, 1994, now abandoned, which in turn, is a continuation of application Ser. No. 981,148, filed Nov. 24, 1992, now abandoned, which, in turn, is a divisional of application Ser. No. 780,346, filed Oct. 22, 1991, now U.S. Pat. No. 5,242,796, which, in turn, is a divisional of application Ser. No. 057,566, filed Jun. 12, 1987, now abandoned, which, in turn, is a continuation-in-part of application Ser. No. 881,372, filed Jul. 2, 1986, now abandoned.

FIELD OF THE INVENTION

This invention relates to DNA sequencing using reporter-labeled DNA and, more particularly, to a fluorescence-based system for detecting the presence of radiant energy from different species following separation in time and/or space, and fluorescent dyes for use therewith. The dyes are a family of closely-related yet distinguishable fluorescent dyes. Methods for protecting, activating, and coupling these dyes are disclosed. A set of fluorescence-labeled DNA chain-terminators, prepared using this methodology, are employed for the generation of fluorescence-labeled DNA sequencing fragments. A photometric detection system capable of detecting these fragments during electrophoretic separation and identifying the attached fluorescent reporter is described.

BACKGROUND OF THE INVENTION

DNA sequencing is one of the cornerstone analytical techniques of modern molecular biology. The development of reliable methods for sequencing has led to great advances in the understanding of the organization of genetic information and has made possible the manipulation of genetic material (i.e. genetic engineering).

There are currently two general methods for sequencing DNA: the Maxam-Gilbert chemical degradation method [A. M. Maxam et al., *Meth. in Enzym.* 65 499–559 (1980)] and the Sanger dideoxy chain termination method [F. Sanger. et al., *Proc. Nat. Acad. Sci. USA* 74 5463–5467 (1977)]. A common feature of these two techniques is the generation of a set of DNA fragments which are analyzed by electrophoresis. The techniques differ in the methods used to prepare these fragments.

With the Maxam-Gilbert technique, DNA fragments are prepared through base-specific, chemical cleavage of the piece of DNA to be sequenced. The piece of DNA to be sequenced is first 5'-end-labeled with $^{32}P$ and then divided into four portions. Each portion is subjected to a different set of chemical treatments designed to cleave DNA at positions adjacent to a given base (or bases). The result is that all labeled fragments will have the same 5'-terminus as the original piece of DNA and will have 3'-termini defined by the positions of cleavage. This treatment is done under conditions which generate DNA fragments which are of convenient lengths for separation by gel electrophoresis.

With Sanger's technique DNA fragments are produced through partial enzymatic copying (i.e. synthesis) of the piece of DNA to be sequenced. In the most common version, the piece of DNA to be sequenced is inserted, using standard techniques, into a large, circular, single-stranded piece of DNA such as the bacteriophage M13. This becomes the template for the copying process. A short piece of DNA with its sequence complementary to a region of the template just upstream from the insert is annealed to the template to serve as a primer for the synthesis. In the presence of the four natural deoxyribonucleoside triphosphates (dNTP's), a DNA polymerase will extend the primer from the 3'-end to produce a complementary copy of the template in the region of the insert. To produce a complete set of sequencing fragments, four reactions are run in parallel, each containing the four dNTP's along with a single dideoxyribonucleoside triphosphate (ddNTP) terminator, one for each base ($^{32}P$-Labeled dNTP is added to afford labeled fragments.) If a dNTP is incorporated by the polymerase, chain extension can continue. If the corresponding ddNTP is selected, the chain is terminated. The ratio of ddNTP to dNTP's is adjusted to generate DNA fragments of appropriate lengths. Each of the four reaction mixtures will, thus, contain a distribution of fragments with the same dideoxynucleoside residue at the 3'-terminus and a primer-defined 5'-terminus.

In both methods, base sequence information which generally cannot be directly determined by physical methods has been converted into chain-length information which can be determined. This determination can be accomplished through electrophoretic separation. Under denaturing conditions (high temperature, urea present, etc.) short DNA fragments migrate as stiff rods. If a gel matrix is employed for the electrophoresis, the DNA fragments will be sorted by size. The single-base resolution required for sequencing can usually be obtained for DNA fragments containing up to several hundred bases.

To determine a full sequence, the four sets of fragments produced by either Maxam-Gilbert or Sanger methodology are subjected to electrophoresis in four parallel lanes. This results in the fragments being spatially resolved along the length of the gel. The pattern of labeled fragments is typically transferred to film by autoradiography (i.e. an exposure is produced by sandwiching the gel and the film for a period of time). The developed film shows a continuum of bands distributed between the four lanes often referred to as a sequencing ladder. The ladder is read by visually scanning the film (starting with the short, faster moving fragments) and determining the lane in which the next band occurs for each step on the ladder. Since each lane is associated with a given base (or combination of bases in the Maxam-Gilbert case), the linear progression of lane assignments translates directly into base sequence.

The Sanger and Maxam-Gilbert methods for DNA sequencing are conceptually elegant and efficacious but they are operationally difficult and time-consuming. Analysis of these techniques shows that many of the problems stem from the use of a single radioisotopic reporter.

The use of short-lived radioisotopes such as $^{32}P$ at high specific activity is problematic from both a logistical and a health-and-safety point of view. The short half-life of $^{32}P$ requires that reagent requirements must be anticipated several days in advance and that the reagent be used promptly. Once labeled DNA sequencing fragments are generated they are prone to self-destruction and must be immediately subjected to electrophoretic analysis. The large electrophoresis gels required to achieve single base separation lead to large volumes of contaminated buffer which must be disposed of properly. The autoradiography required to subsequently visualize the labeled DNA fragments in the gel is a slow process (overnight exposures are common) and adds considerable time to the overall operation. Finally, there are the possible health risks associated with use of such potent radioisotopes.

The use of only a single reporter to analyze the position of four bases lends considerable operational complexity to the overall process. The chemical/enzymatic steps must be run in separate containers and electrophoretic analysis must be carried out in four parallel lanes. Thermally induced distortions in mobility result in skewed images of labeled DNA fragments (e.g. the smile effect) which in turn, lead to difficulties in comparing the four lanes. These distortions often limit the number of bases that can be read on a single gel.

The long times required for autradiographic imaging along with the necessity of using four parallel lanes force one into a "snapshot" mode of visualization. Since one needs simultaneous spatial resolution of a large number of bands one is forced to use large gels that are typically 40 cm or more in length. This results in additional problems: large gels are difficult to handle and are slow to run adding more time to the overall process.

Finally, there is a problem of manual interpretation. Conversion of a sequencing ladder into a base sequence is a time-intensive, error prone process requiring the full attention of a highly skilled scientist. Numerous attempts have been made to automate the reading and some mechanical aids do exist but the process of interpreting a sequence gel is still painstaking and slow.

To address these problems one can consider replacing $^{32}$P/autoradiography with some alternative, non-radioisotopic reporter/detection system. Such a detection system would have to be exceptionally sensitive to achieve a sensitivity comparable to $^{32}$P; each band on a sequencing gel contains on the order of $10^{-16}$ mole of DNA. One method of detection which is capable of reaching this level of sensitivity is fluorescence. DNA fragments could be labeled with one or more fluorescent dyes. Excitation with an appropriate light source would result in a characteristic emission from the dye thus identifying the band.

The use of a fluorescent dye as opposed to a radioisotopic label would allow one to more easily tailor the detection system for this particular application. For example, the use of four different fluorescent dyes distinguishable on the basis of some emission characteristic (e.g. spectrum, life-time, polarization) would allow one to uniquely link a given tag with the sequencing fragments associated with a given base. With this linkage established, the fragments could be combined and resolved in a single lane and the base assignment could be made directly on the basis of the chosen emission characteristic.

The "real-time" nature of fluorescence detection would allow one either to rapidly scan a gel containing spatially resolved bands (resolution in space) or sit at a single point on the gel and detect bands as they sequentially pass through the detection zone (resolution in time). Large gels would not necessarily be required. Furthermore, a "real-time", single lane detection mode would be very amenable to fully automated base assignment and data transfer.

Several attempts to develop a fluorescence-based DNA sequencing system have been described. One system developed by a group at the California Institute of Technology, has been disclosed in L. M. Smith, West German Pat. Appl. #DE 3446635 Al (1984): L. E. Hood et al., West German Pat. Appl. #DE 3501306 Al (1985): and L. M. Smith et al., *Nucleic Acids Research*, 13 2399–2412 (1985). This system conceptually addresses the problems described in the previous section but the specifics of the implementation appear to render this approach only partially successful.

The Cal Tech system employs four sets of DNA sequencing fragments, each labeled with one of four fluorescent dyes. Two representative sets of fluorescent dyes are described. Each set is comprised of dyes from at least two different structural classes.

The emission maxima are spread over a large range (approximately 100 nm) to facilitate discrimination between the four, but unfortunately the absorption (excitation) maxima are also-comparably spread. This makes it very difficult to efficiently excite all four dyes with a single monochromatic source and adequately detect the resulting emissions.

In contrast, the use of dyes with closely spaced absorption (and corresponding emission) peaks to enhance the excitation efficiency causes other difficulties. A detection system for DNA sequencing must be able to distinguish between four different dye emission spectra in order to identify the individual labeled fragments. These emissions are typically of relatively low intensity. Therefore, the detection system must have a high degree of sensitivity (better than $10^{-16}$ moles DNA per band) and selectivity, along with a means to minimize stray light and background noise, in order to meet desired performance characteristics. The system also must be able to frequently monitor the-detection area in order to avoid missing any fragments that migrate through the gel past the detection window. Such a detection system should be relatively cost efficient to allow for multiple detection devices within a single instrument without detrimentally affecting mill cost.

Many detection devices are known which utilize fluorescence in a detection scheme. One such device is discussed in "Quantitative Fluorescence Analysis of Different Conformational Forms of DNA Bound to the Dye . . . and Separated by Electrophoresis" by Naimski et al., Anal. Biochem., 106,471–475, 1980. In this electrophoresis/detection system a glass tube is filled with agarose gel for separating the relatively large DNA fragments. A scanning monochromator is then used as the detection system for defining each of the large fragments. It is known that scanning monochromators can accurately measure a wide range of spectral characteristics; however, much light is lost due to the limited ability of the monochromator and its associated optics to collect and disperse emitted light. These detection techniques limit the fraction of light that can be sensed and measured. Consequently, their sensitivity for low light applications is limited. Additionally, light collected sequentially is typically inefficient.

The detection apparatus disclosed by Smith et al. (see above) uses a series of narrow band interference filters in order to select the wavelengths impinging upon a single or multiple photodetectors. This type of system has the advantage of being rather simple and inexpensive; however, it does have substantial deficiencies. The specific system described uses a filter photometer which can either use multiple interchangeable filters with one photodetector or multiple stationary filters with corresponding detectors. The first of these devices, a rotary filter with a single detector (see FIG. 3 of Smith et al.), has the disadvantage of limiting the time period during which each of the filtered regions can be measured. The detector time must be shared with the different filters in order to distinguish among different emission spectra. The Smith et al. system has additional optical difficulties which need not be dealt with here.

More serious problems still result from using dyes which have different net charges. The conventional sequencing gel displayed in the Smith et al., *Nucleic Acids Research* paper illustrates T-lanes produced from primers labeled with each of four dyes. It is clear that there are significant differential perturbations in the electrophoretic mobilities. A complete set of sequencing fragments bearing these four dyes will, when combined, show considerable overlap and perhaps even misordering when subjected to electrophoresis in a single lane. This effect, combined with the aforementioned large dynamic range in signal intensity, makes it difficult to perform single-lane sequencing with this dye set.

Finally, the methodology used to prepare the fluorescence-labeled sequencing fragments creates difficult sequencing conditions. For Maxam-Gilbert sequencing, 5'-labeled oligonucleotides are enzymatically ligated to "sticky ended", double-stranded fragments of DNA produced through restriction cleavage. This limits one to sequencing fragments produced in this fashion. For Sanger sequencing, 5'-labeled oligonucleotides are used as primers. Four special primers are required. To use a new vector system one has to go through the complex process of synthesizing and purifying four new dye-labeled primers.

A second approach to automation of non-radiolabel DNA sequencing was disclosed by Ansorge, W., et al., *J. Biochem. Biophys. Methods,* 13:315–323 (1986), in which a single fluorescent label was covalently attached to the 5' end of a 17-base oligonucleotide primer. This primer was reacted in four vessels with the standard dideoxynucleotide sequencing chemistry method that was modified to omit the radiolabeled nucleotide, to produce sets of enzymatically copied DNA fragments of varying length. Each of the four vessels contained a dideoxynucleotide chain terminator corresponding to one of the four DNA bases which allowed terminal base assignment from conventional electrophoretic separation in four gel lanes. Each fragment carried a 5'-tetramethylrhodamine fluorescent label which was excited by an argon ion laser passing through the width of the entire gel. Fluorescent emissions of DNA bands resolved over time were collected from the four lanes with separate, stationary means for each lane comprising imaging optics, field apertures, light guides, filter assemblies, and photomultipliers in series.

One advantage claimed by this approach is the need for fewer moving parts in the apparatus due to stationary detectors which allows continuous monitoring of the four gel lanes. This monitoring method, although more complex than that used with one lane, reportedly offers the advantage of determining the presence of a labeled band for base assignment relative to the absence of bands in the remaining three lanes to improve confidence in the assignment. In fact, the use of a single label requires the use of four lanes for base assignment and the system as presented is incapable of further simplification to improve the capacity or throughput of the instrument. The system is also limited in potential accuracy by the requirement for faithful lane-to-lane relative positioning for a single sequence analysis. Operational complexities such as thermal gradients and gel impurities may defeat this positional integrity to produce local gel distortions which affect band mobilities, that may in turn, compromise base sequence assignments.

The use of labeled primers by Ansorge et al. and Smith et al. is inferior in other respects as well. The polymerization reactions must still be carried out in separate vessels. All DNA fragments—be they bona fide termination fragments or extraneous fragments—will be labeled. This is similar to the existing system where effectively all fragments containing incorporated adenosine nucleotides are labeled. Thus, the resulting sequencing pattern will retain most of the artifacts (e.g. false or shadow bands, pile-ups) encountered in the current methods.

Finally. Brumbaugh, J. A. et al. in European Patent Application 85103155.9, published Oct. 9, 1985, disclosed a system and method for post-labeling strands of DNA which optionally contained pre-marked nucleosides. The pre-marking could be accomplished by covalent attachment of biotin to a desired chain terminating nucleotide before the nucleotide was used in a modification of the Sanger DNA chain termination method. However, the pre-marked nucleotide was not detectable in the disclosed system. The pre-marked strands of DNA prepared in separate vessels corresponding to the A, T, C, and G DNA bases, were electrophoretically separated and then exposed to a complementary binding material, typically avidin, which had a fluorophore such as fluorescein covalently attached to it. The fluorophore was detected and the signal presence was related to the particular vessel or gel/lane corresponding to A, T, C, or G originally prepared. This post-labeling method requires the preparation and subsequent electrophoretic separation of marked DNA strands in separate vessels and gels/lanes, respectively. There is no disclosure of any method or system capable of labeling DNA strands differentially in the same vessel simultaneously during the reactions of a chain termination method, or differentiating labels during strand detection in a single gel/lane of a suitable detection system.

SUMMARY OF THE INVENTION

This invention seeks to overcome many of the disadvantages of the prior art. It includes a DNA sequencing system which has many of the desired performance characteristics without many of the deficiencies previously discussed. This invention is a system for detecting the presence of radiant energy from different species, typically reporter-labeled DNA, following separation in time and/or space, and identifying the species. The system includes means responsive to the spectra of the species for generating a first signal that varies in amplitude in a first sense as a function of the nature of the species, means responsive to the spectra for generating a second signal that varies in amplitude in a second sense different than the first sense as a function of the nature of the species, and means responsive to the first and second signals for obtaining a third signal corresponding to the ratio of functions of the first and second signals, the amplitude of the third signal being indicative of the identity of the species.

The means for generating the first and second signals may include a dichroic filter, with a transmission/reflection characteristic that varies as a function of wavelength, means to direct the emissions to the filter, first and second detectors positioned respectively to receive the transmitted and reflected emissions and generate first and second signals corresponding to the intensities of each. Preferably the dichroic filter characteristic has a relatively sharp transition from transmission to reflection which occurs near the center of the species emission spectra. With the transition point located near the center, the change in amplitude of the third signal is more evenly distributed over the range of spectra.

Typically, the species to be analyzed are DNA fragments or other molecules covalently labeled with fluorescent materials that have closely spaced spectra. These molecules are typically contained in an electrophoresis gel adapted to separate them by size, charge, or other physical properties. The system includes a laser or other radiant energy source with an output within the excitation region of the fluorescent material.

The emitting portion of the labeled species to be detected, e.g., a DNA fragment, can have the structure

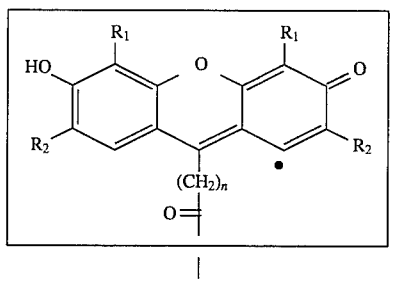

wherein n=2 or 3 and $R_1$ and $R_2$ include H, lower alkylo halo, lower alkoxy and cyano.

There is also described a method of detecting the presence of radiant energy emitted from different species, following separation in time and/or space, and determining the identity of each such species that emit, comprising the steps of obtaining functions of the emitted energy which vary over the wavelengths of the closely spaced spectra in different senses, ratioing such functions, the ratio being indicative of the identity of the species. The function of the emitted energy may be obtained by passing the radiant energy through a dichroic filter with a transmission/reflection characteristic which varies as a function of wavelength.

A process is described for DNA sequence analysis according to a modification of the Sanger chain termination method where the chain terminator carries the reporter. Preferably, the chain terminator carries a colored, more preferably fluorescent reporter. The chain terminator can be one of the following structures

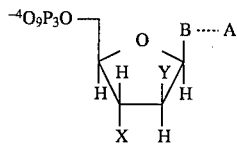

where
(a) X is H, $NH_2$, or halo, and Y is H, $NH_2$, OH, or halo, or
(b) X=Y=OH.
or

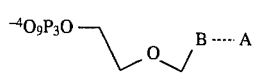

where A can be a fluorescent reporter having the structure

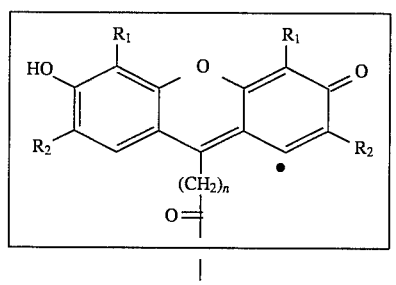

where n is 2 or 3, and $R_1$ and $R_2$ are H, lower alkyl, halo, lower alkoxy, and cyano, B is a heterocyclic base such as uracil, cytosine, 7-deazaadenine, 7-deazaguanine, or 7-deazahypoxanthine where the pyrimidines are linked to the sugar part through the $N_1$ position and the deazapurines are linked to the sugar part through the $N_9$ position (purine numbering), and the dotted line is a linker and optional spacer (group of atoms) joining the fluorescent part (A), preferably via an amide bond, and the heterocyclic base (B) provided that if B is a pyrimidine the linker is attached to the 5-position of that pyrimidine and if B is a deazapurine the linker is attached to the 7-position (purine numbering) of that deazapurine.

According to another aspect of this invention, a process of DNA sequence analysis according to the Sanger chain termination method as modified by this invention, is provided where each of the four chain terminators corresponding to the four bases carries a different distinguishable reporter. The four chain termination reactions may thus be carried out in separate vessels and combined prior to electrophoretic analysis or carried out in a single vessel.

The combined DNA sequencing fragments thus produced can be subjected to simultaneous electrophoretic separation in a single lane. Excitation of the fragments bearing their respective reporters by a single source results in their characteristic emission thereby allowing detection and identification.

The set of four reporters are chosen such that all four are efficiently excited by a single source and have emission spectra that are similar but distinguishable. The differential perturbations in electrophoretic mobility of the attached DNA fragments are small. This requirement can generally be satisfied if the four reporters have similar molecular weights, shape, and charge.

These criteria can be met with reporters having fluorescent parts with the structure

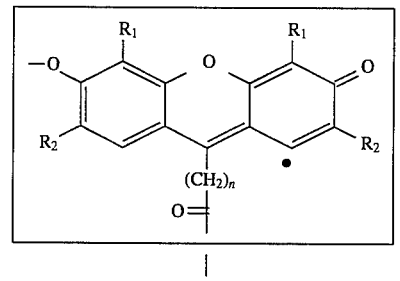

where n is 2 or 3 and $R_1$ and $R_2$ are chosen from the group H, lower alkyl, lower alkoxy, halo, and cyano. Such reporters may be introduced via protected, activated intermediates of the structure

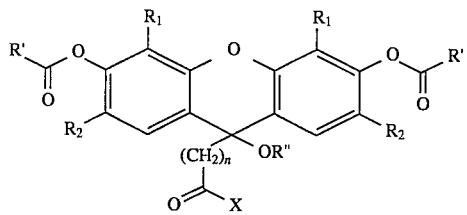

where n is 2 or 3, $R_1$ and $R_2$ are H, lower alkyl, lower alkoxy, halo, and alkoxy, R" is alkyl, R' is alkyl or aryl, and X is a good leaving group.

The system and method of this invention have the ability to distinguish in real time between the relatively small wavelength differences in emission spectra, while maintaining a relatively high degree of sensitivity. The system delivers a high portion of the usable light onto the photometric detectors. Finally, the detection system provides continuous monitoring of the gel containing the fluorescent species. This feature reduces the possibility of deriving incomplete data that are typically inherent in intermittent type detection systems. All of the above-mentioned features are incorporated into this unique system at a relatively low mill cost.

BRIEF DESCRIPTION OF THE DRAWINGS

The invention may be more fully understood from the following detailed description thereof taken in connection with accompanying drawings which form a part of this application and in which:

FIG. 1 is a partial block, partial diagrammatic layout of a system constructed in accordance with this invention for detecting the presence of radiant energy from different sources that each emit energy at different but closely spaced wavelengths:

FIG. 2 is a diagrammatic representation of a single electrophoresis gel capable of being used in the system of FIG. 1

FIGS. 4 and 5 shows typical detector signals obtained as a function of time for the labeled bases T, G, A and C

DETAILED DESCRIPTION OF THE INVENTION

Figure 3:
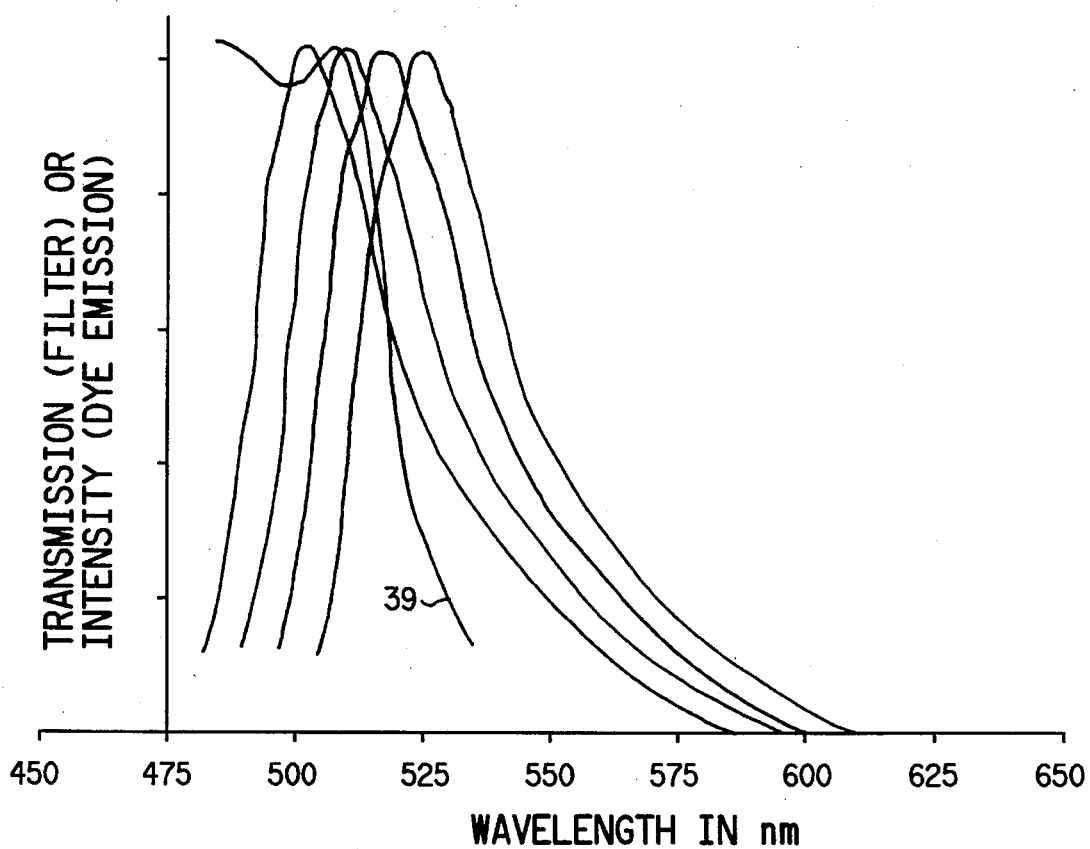
FIG. 3 shows the relationship of the dye emission radiation and the transmission/reflection characteristics of the dichroic filter used in the system of FIG. 1

The radiation from very closely spaced emission bands may be detected using the system of this invention. These closely spaced emissions are produced from preselected reporter species which are irreversibly bound to the materials that are to be analyzed in the system. Acceptable reporters are generally one or more species chosen for their ability to emit radiation over a narrow range of wavelengths, typically between a 50 and 100 nm range, preferably over a 20 to 50 nm range. Preferably, the peak maxima should be spaced no closer than 2 nm. One reporter species may be capable of emitting energy at more than one wavelength range, depending upon the manner of attachment to the materials of interest and the conditions of analysis in the system. However, individual reporters with unique emission characteristics in the system are more conventionally chosen to emit radiation in the wavelength range to be detected. Preferred reporter species are described below.

Although the system of this invention has broad applicability, it will be described in a particular application of DNA sequencing.

In this preferred form of the invention, reporter-labeled DNA sequencing fragments are produced in a single vessel. The contents of this vessel, reporter-labeled DNA chains of varying lengths, are passed through an electrophoresis apparatus for separation. For this purpose, as is illustrated in FIG. 2, the electrophoresis may be carried out by a suitable electrophoresis slab 10 arrangement having a thickness of about 0.2 mm to 0.4 mm and about 25 to 40 centimeters long. Other sizes may be used as appropriate. This slab 10 has a suitable gel 11, typically 6% to 8% polyacrylamide sandwiched between glass or plastic supports 12. The slabs (gels) are prepared in a conventional manner.

The slab 10 is typically placed in an upright position in a holder with the upper end of the slab 10 extending through and into an upper container 16 holding a buffer solution 24 and downwardly into a second container 14 also holding a buffer solution 18. The buffer solution is any suitable buffer typically a 0.1M tris-borate-EDTA, pH 8.3 may be used. In this manner, the buffer contacts the gel at either end of the slab in order to make electrical contact therewith. With this arrangement, a sample of the reporter-labeled DNA fragments can be pipetted into a cavity (not shown) that is created at the top of the gel. An electrical circuit is then completed through the terminals 20 in reservoir containers 14 and 16. A suitable potential is needed to obtain separations for gels of this particular length and thickness. The positive electrode is located at the lower end of the slab to cause the DNA fragments to migrate downwardly. Under these conditions, as the fragments migrate through the gel they are separated spatially into bands. The detection zone is located near the bottom of the slab. In this zone, the fragments are irradiated by a laser beam 31 and excitation/ emission occurs as the fragments move through the zone.

An optical arrangement for irradiating the electrophoresis slab 10 is shown in FIG. 1. The system of FIG. 1 may be used with any fluorescent or other type reporter system to distinguish between and measure the intensity of closely spaced emission radiation bands. However, it will be described, as noted above, in the preferred application of detecting the emissions from reporter-labeled DNA fragments, where the reporter species are fluorescent compounds. It includes the laser 30 which is selected to provide a specific wavelength determined as a function of the excitation wavelengths of the preferred excitable reporter species used. For example, the specific source used for the fluorescent reporters disclosed herein is an argon ion laser with a wavelength of 488 nm and a 0.8 mm diameter light beam operated at about 25 to 40 mW. The laser beam passes through an excitation filter 32 and focusing lens 33 which concentrates the beam to a diameter of about 0.2 mm at the detection zone of the electrophoresis slab 10.

The filter 32 is selected to block out the undesired excitation wavelengths that could otherwise interfere with the detection process. If the laser light is very pure, this filter may be omitted. The light beam entering the slab excites the reporter-labeled material, here fluorescently labeled DNA fragments, as they migrate through the detection zone, causing them to fluoresce at wavelengths shifted from the excitation wavelength. Although the peak emission wavelengths characteristic of the particular dyes disclosed hereinafter, when free in solution, are 505, 512, 519 and 526 nm, it is to be noted that the detection system is adaptable to discriminate wavelengths associated with other sets of reporters with closely spaced emission bands. Furthermore, while a laser source is preferred since it allows a minimum of extraneous light to impinge upon the sample, with suitable filtering and optics, other sources including a non-coherent source such as a xenon arc lamp could be used.

The light emitted by the fluorescent species is collected by suitably positioned collimating lens 34 which produces a collimated beam of light for transmission to dichroic filter 38 via an emission filter 36 to eliminate essentially all light except for the specific wavelengths characteristic of the fluorescence. Using this filter, substantially all of the light below 500 nm and above 560 nm is filtered out with the light between these limits being transmitted with greater than 50% efficiency.

In accordance with this invention, the dichroic interference filter 38 enables this system to distinguish between closely spaced emission spectra. It is oriented typically to about 45° with respect to the incident beam. Light impinging on this filter will either be reflected or transmitted through the filter. For the emission maxima of the fluorescent reporters, when coupled to DNA fragments, disclosed hereinafter, namely, 515, 524, 530 and 536 nm filter 38 has been chosen to have the reflective/transmissive characteristics shown in FIG. 3. The dichroic filter 38 is seen to have a sharp transmission/reflection transition 39 which lies approximately in the center of the fluorescence bands which are characteristic of these four reporters. As the fluorescence spectrum shifts from the lower to higher wavelengths, the ratio of transmitted to reflected light decreases in a continuous manner. Although this particular filter has been chosen to accommodate the reporters selected for this application, a different set of reporters would require different filter characteristics.

Light (reflected or transmitted) from the dichroic filter 38 passes through respective focusing lenses 40 to respective detectors 42. The detectors 42, preferably are photomultiplier tubes. They are known to have a high degree of sensitivity within the spectral bands of interest. Alternatively, silicon photodiodes or other similar detectors may be used. In the instance where the detectors 42 are positioned within a close, predetermined distance from a collecting aperture, the collimating lens 34 can be omitted. When this lens is omitted, the collecting aperture may be defined by having an opening that corresponds to the desired sensing area of the detector 42, or an aperture can be defined by an alternate means, such as a fiber optic face plate. In similar fashion, the focusing lenses 40 can be omitted if the detector sensing area is large enough to sufficiently and directly collect the available light.

Figure 7:
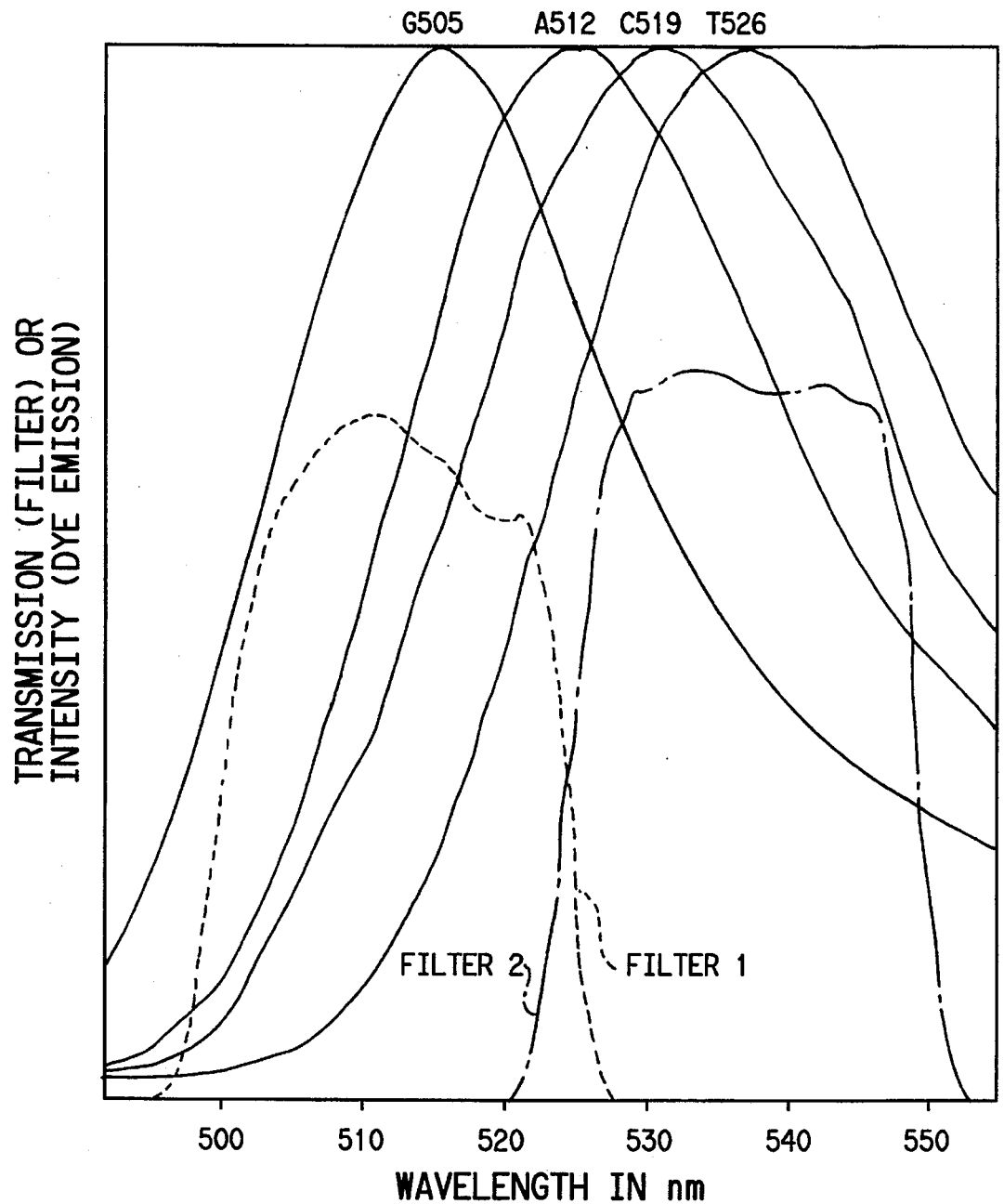

It should be apparent that the function of the dichroic filter 38 could also be and preferably is served by two separate filters and appropriate apertures placed in the light path from the emitted light source to the detectors 42, in which each filter has in a transmission sense, two different transmission characteristics. i.e., either the reflective or transmissive transition characteristic of the dichroic filter. In this manner, the two detectors 42 are still dedicated to the transmissive and reflective characteristics provided by the dichroic filter in the previous description. The passbands of these two filters is seen more clearly in FIG. 7 and are labeled Filter 1 and Filter 2. The passbands of these two filters are seen to overlap at about the center of the fluorescence bands which are characteristic of the four reporter labeled terminators used herein of G515, A524, C530, and T536 nm.

A system of this type using two filters is described in the copending Robertson et al. application, the contents of which are incorporated herein by reference. As described in Robertson et al., a pair of modules are positioned above and below a plane in which the reporter exciting light beam scans multiple lanes on an electrophoresis gel. Each channel contains reporter-labeled DNA fragments. Each detection module comprises a photomultiplier tube having a wide entrance area and a separate wavelength selective filter positioned between its PMT and the fluorescent species in the gel. These filters are interference filters having complementary transmission band characteristic which simulate the dichroic filter action. The filters permit the PMT's to generate signals that vary in amplitude in different senses as a function of the nature of the species. One filter largely passes the lower emission wavelengths and rejects the high emission wavelengths while the other filter does precisely the reverse. Transmission filters may be used with each interference filter to reject light from off axis angles greater than a predetermined angle. The wavelength filters have roughly complementary transmission vs. wavelength characteristics in the emission region of the four dyes, with the transition wavelengths occurring near the center of the species radiant energy spectra.

Figure 4A:
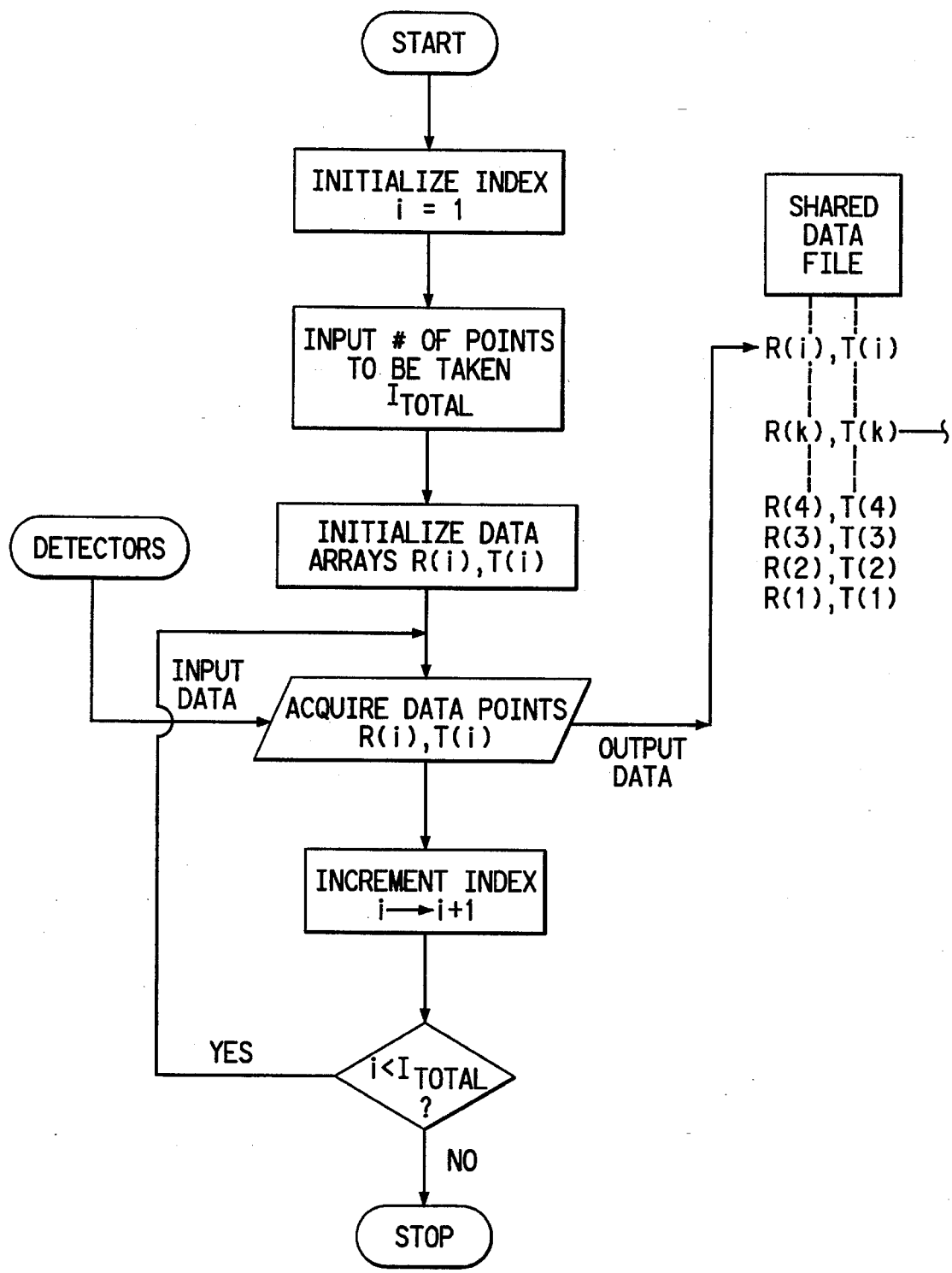
FIGS. 4A, 4B and 4C are flow diagrams of the data processing steps used to evaluate the detected emission peaks
Figure 4B:
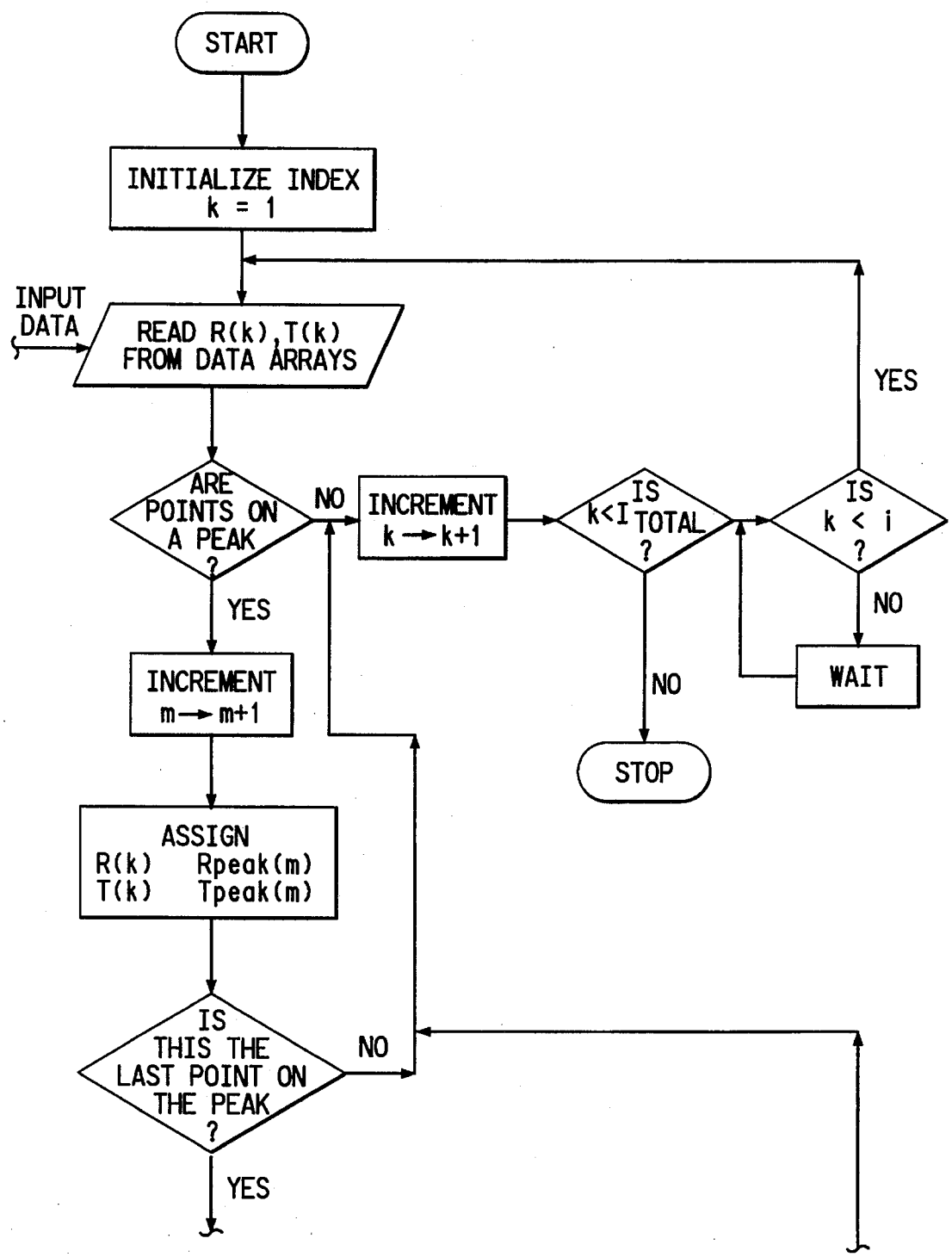
Figure 4C:
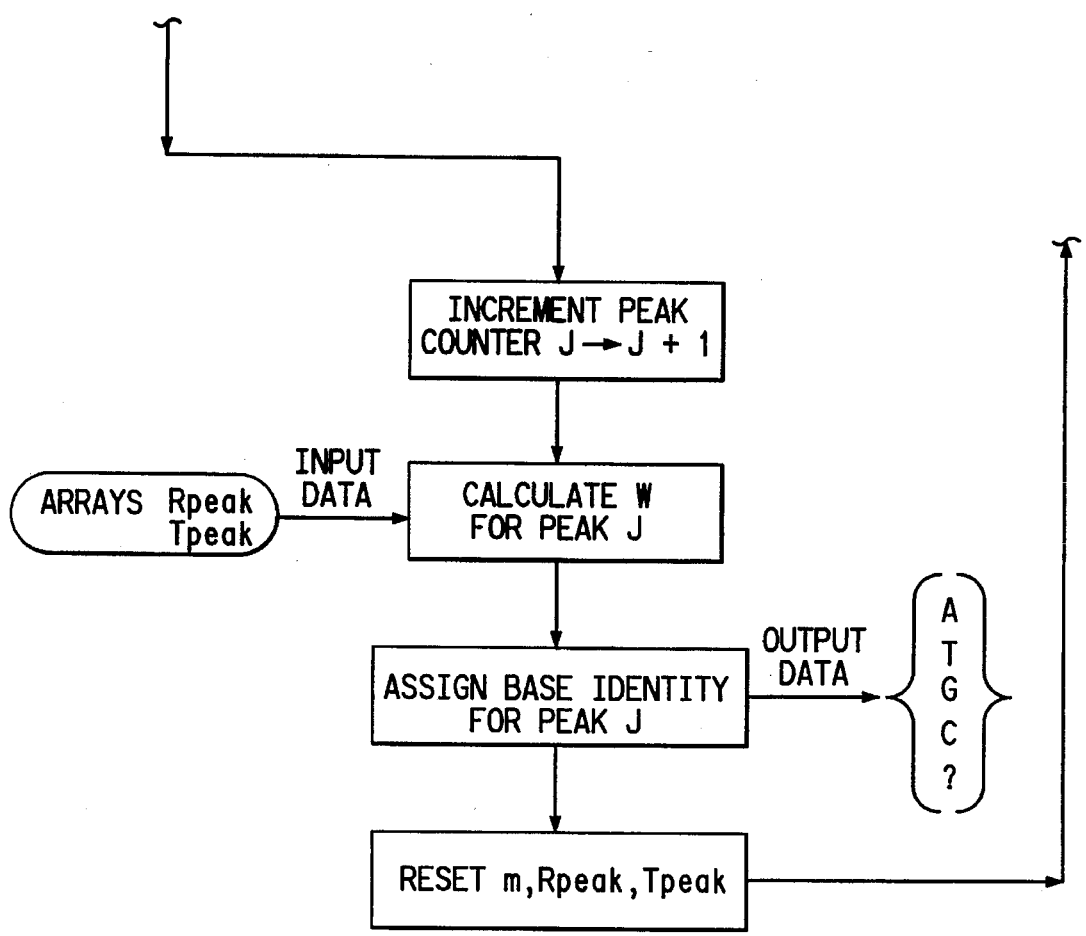

The electrical signals from the detectors 42 are then passed via respective preamplifiers 46 to analog-to-digital (A/D) converters 48 and thence to a system controller 52. The tasks of the system controller 52 may be performed by a small computer such as an IBM PC. A function of the system controller which is described by the flow diagram of FIG. 4, is to compute the ratio of the two signal functions. The dichroic filter 38 modulates the intensity of the signals in each of the different wavelength bands according to wavelength, i.e., for the reflected light detector, the shorter wavelength emissions will have a lower amplitude signal value and the longer wavelength emissions will have a higher amplitude. Thus, as a particular reporter species, i.e., a fluorescently-labeled DNA fragment in the preferred embodiment of the invention, passes through the detection zone following separation in space in the gel 10, its emissions will be varying in amplitude as a function of its wavelength and also time (because of the movement through the gel 10). The amplitude modulated light signals are converted to electrical signals and digitized for such processing as described. After conversion, the digital signals are ratioed, i.e., to obtain the quotient of the reflected to transmitted fluorescent light. These digital signals are those representing a peak in the light signal corresponding to a set of DNA fragments. Signals corresponding to either the peak height or peak area are the ones ratioed. The magnitude of the ratio signal is indicative of the identity of the species. The function W is defined as the ratio of peak intensity in one detector to peak intensity in the other detector, for example, the peak intensity in the transmitted light detector divided by the peak intensity in the reflected light detector. The magnitude of the ratio signals for each reporter tends to fall into grouping or clusters which are uniquely indicative of each reporter as may be seen in the illustrative Example 10 below.

This amplitude modulation and ratioing procedure, whether accomplished with a dichroic filter or with separate filters to generate two signals that each vary in different senses in response to the same spectra of the same species under test, may be described mathematically. Thus, the total electrical signal (corresponding to the detected light signal) present during a reporter peak emission consists of components due to scattering and stray light as well as the signal due to the fluorescence itself from each of the different reporters. During electrophoresis, the reporter fluorescence signal may be distinguished from other background components because the fluorescence signals vary in time or space in a predictable manner. This is in contrast with the background noise signal which contributes a relatively constant signal, particularly when there is no relative motion between the detector and gel. In a stationary gel and detector configuration, the fluorescence signals vary in time due to the movement of the reporter through the gel. Alternatively, the gel may remain stationary following electrophoresis, and the detection system moved relative to the gel or vice versa. In still another alternative, the detection system may be moved while migration in the gel is still taking place.

Figure 5:
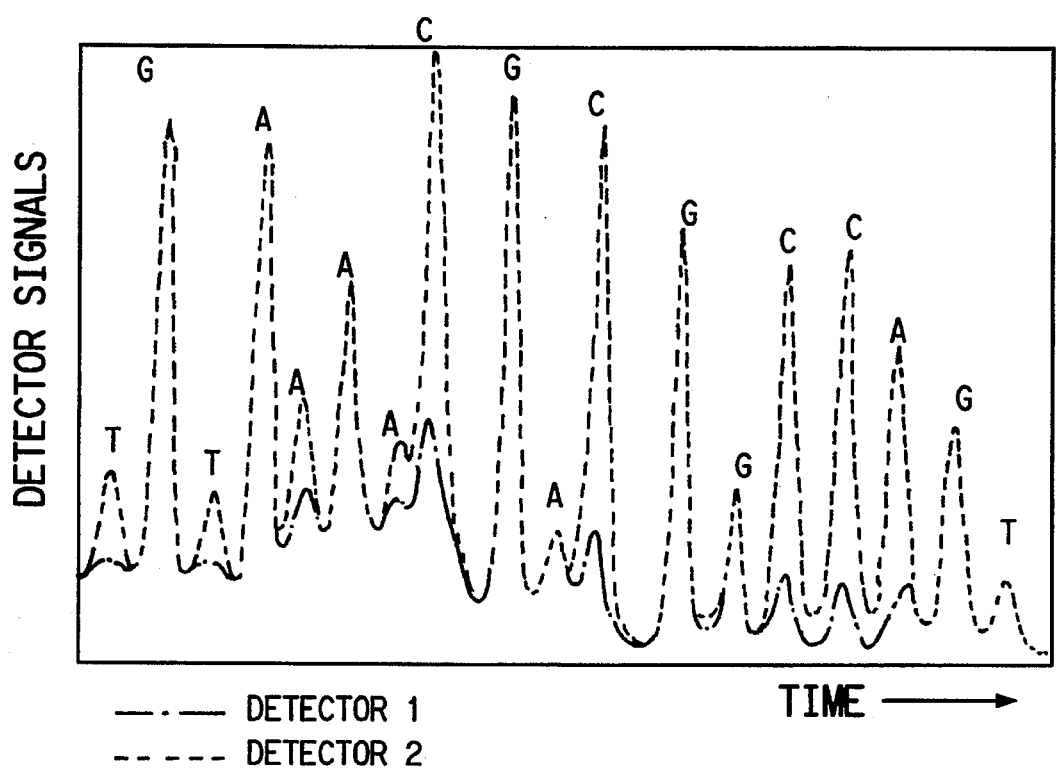

There may be seen in FIG. 5 a representation of how the two detector output signals vary as a function of time. Each pair of peaks in the figure corresponds to a different set of DNA fragments which correspond to the sequence of bases occurring in the piece of DNA under test. The ratios of each pair of peaks falls into four groupings each corresponding to a particular DNA base. It is these ratio groupings which identify the particular base T, C, A, or G.

In order to improve selectivity between the reporters (determined by values of W), the change in W over all the combinations of the different fluorescent reporter emissions must be optimized. This can be accomplished by choosing a dichroic filter, or its equivalent as noted above, with transmission/reflection characteristics which change substantially over the different reporter emission spectra. However, for a closely spaced group of reporters, it is preferable to have a relatively sharp filter transition that occurs near the center of the reporter emissions in order to evenly distribute the change in W for the different emission spectra (FIG. 3).

In essence, this system provides uncommon measurement sensitivity and selectivity performance. With this unique system, light is efficiently directed to the two closely coupled detectors; and high levels of sensitivity and selectivity are feasible in an inexpensive, compact, and easy to use system.

FLOW CHART

The system controller 52 converts the digital signals received from the A/D converters 48 into DNA sequence information. In most cases, this will be done by a computer executing programs in real time. This means that data is processed and sequence information is determined concurrently with the acquisition of raw data from the detectors.

Conceptually, the operation of the system controller may be broken down into three interacting processes: data acquisition or input, data analysis, and output. The processes interact by sharing data and by sharing timing information which keeps them "in step" and prevents them from interfering with one another. The details of how these interactions are accomplished depend on the language and hardware chosen and is of no fundamental concern here.

The data acquisition and processing so performed can be understood by referring to the flow charts in FIG. 4. This figure represents a general method by which the raw data from the DNA sequencer detectors may be converted into output, i.e., the DNA sequence of the sample. FIG. 5 shows hypothetical curves of raw detector output vs. time and illustrates some of the variables used in what follows. In this discussion we define the following terms:

1. i is the index of the current data point being acquired. This point is acquired at time t(i) min.
2. k is the index of the current data point being processed. This point corresponds to data taken at t(k)min. In a general data processing scheme, k need not equal i, i.e. data processing may lag behind data acquisition.
3. t(i) is an array of time points at which data was acquired. Example: t(5)=6.2 min would indicate the 5th data point was acquired at 6.2 minutes after the start of the run.
4. R(i) is the array of data from the reflection detector.
5. T(i) is the array of data from the transmission detector.
6. J is a count of peaks detected.
7. N is the number of data points across a given peak.
8. m is an index of points across a defined peak in either R(i) or T(i). m=1 at the start of a peak; m=N at the end of a peak.
9. W is the function defined in the previous section.

Data Acquisition

A general data acquisition process is shown by the flow chart on the left of FIG. 4. The index i, which points to the current acquired data, is initialized. The program accepts an input which determines how long the run will take, i.e. the total number of data points $I_{total}$. After the raw data arrays R and T are initialized, the process enters an acquisition loop as shown in FIG. 4. Data are read from the detectors, digitized, and placed in the arrays as R(i) and T(i) for the reflected and transmitted signals, respectively, acquired at time t(i). (For the purposes of this discussion, the two readings are simultaneous.) At this point, the index i is incremented and compared to $I_{total}$. If i is less than $I_{total}$, the acquisition loop is repeated. If i equals $I_{total}$, the run is stopped. In a more elaborate scheme, the program could sense when to end the run automatically by measuring several performance parameters (such as signal/noise ratio, peak resolution, or uncertainty in assigning bases) at each peak of the run. If a combination of such factors failed to meet preset criteria, the run would be terminated by the computer. The primary data input is the raw data from the detectors and the output is stored in the data arrays R(i) and T(i) which are shared between the acquisition and the data analysis processes. This scheme is depicted schematically in FIG. 4. Although the two programs run independently and simultaneously, some control information must be passed between them in order to maintain proper timing. For example, the processing program cannot be allowed to overtake the acquisition step because it would then be attempting to process nonexistent data.

Data Processing

The data processing algorithm depicted on the right side of FIG. 4 is an example of a general scheme to detect and identify reporter-labeled species. It is not meant to be all-inclusive. Rather, it illustrates the primary features that are necessary in developing any real analyzer program.

After initializing the processing index k (as distinct from the acquisition index i), the program enters a simple loop which reads data R(k) and T(k) from the raw data arrays provided by the acquisition process. The program then asks whether the current point is on a peak. A number of algorithms exist which can determine this condition; details are not needed here. The term "peak" is meant in a general sense. A peak in R will generally be accompanied by a peak in T. However, depending on the identity of the reporter, the peaks in these two channels may differ considerably in intensity. They will, however, coincide in time. Therefore, a weighted average of the two signals, the stronger of the two signals, or some other combination of R(k) and T(k) could be used to define a "peak" in time.

If the current processed point is not on a peak, the index k is incremented and compared with the acquisition index i. If k equals $I_{total}$, the run is over and the program stops. If k is less than i, the next data points are fetched from the arrays R and T and the loop executes again. If k is equal to i, it means that processing has caught up with data acquisition. In this event, the processing program waits a small period of time (typically a second) and again tests the values of k and i until processing can resume.

If the current processed point is on a peak, the index m is incremented. Index m counts the number of points across the current peak. The values R(k) and T(k) are placed in temporary arrays called Rpeak(m) and Tpeak(m), respectively. The program then tests whether the current point is the last point of the peak (again, known algorithms exists for determining this). If this is not the last point on the peak, program control returns to the upper loop which increments k, tests its value against i, and reads the next pair of data from the arrays R and T.

If the current point is the last point on the peak, the peak counter J is incremented and the program proceeds to determine the identity of the peak. The result is the identity of the next base in the DNA sequence. The program calculates the function W for the current peak as described above, using the arrays Rpeak(m) and Tpeak(m) as input data. Each nucleotide base will have associated with it a pair of peaks which give a characteristic W. Thus, based on the value of W for this peak, the program gives as output the DNA base identity A, T, C, G. The peak point index m and the arrays Rpeak and Tpeak are reset to 0, and the program again enters the upper data acquisition loop as shown in FIG. 1.

Labeling Methods in DNA Sequencing

The strategy used to attach reporters to DNA sequencing fragments in a base-specific fashion is a critical feature of any DNA sequencing system. There are a number of possible approaches each with inherent advantages and disadvantages.

Primer Labeling

The aforementioned primer labeling approach reported by Smith et al. has the advantage that the dye can be placed on the distal, 5'-terminus of the primer using intermediates generated in an automated oligonucleotide synthesizer. Very little interference with the enzymatic 3'-chain extension is expected. However, this approach has a number of disadvantages. Four different dye-labeled oligonucleotide primers are required and the production of sequencing fragments must be carried out in four separate reactions, thus complicating any attempt to automate the overall process. The need for special primers reduces one's flexibility with regards to choice of vector (template). For example, the use of labeled primers makes it difficult to take full advantage of strategies for the rapid sequencing of large amounts of contiguous DNA (e.g., the "walking through the gene" technique). There is a more serious disadvantage in the area of performance. The primer labeling approach results in all fragments being labeled—bona fide sequencing fragments as well as many artifactual fragments will carry the label. Thus, many of the artifacts encountered in conventional sequencing (shadow bands, pile-ups, etc.) will be retained.

Fragment Post-Labeling

Another possible approach is a post-labeling scheme. In this scheme the dye-labeling would be carried out after generating the mixture of sequencing fragments. The advantage here is that standard protocols (either Maxam-Gilbert or Sanger) could be used up to the point of labeling the fragments. The major disadvantage is that labeling would have to be exceptionally selective. Since the attachment of a reporter can be expected to have a measurable incremental effect on the electrophoretic mobility of a DNA sequencing fragment it is essential that this effect be constant for all fragments. Multiple labeling would destroy the relationship between chain-length and electrophoretic mobility and would be disastrous.

Chain Terminator Labeling

According to this invention a third approach is preferred, i.e. chain terminator labeling in a modification of the Sanger DNA sequencing method. The classical Sanger method uses a primer, DNA template, DNA polymerase I (Klenow fragment), three unlabeled deoxynucleotides and one radiolabeled deoxynucleotide in four reaction vessels that each contain one of four 2',3'-dideoxynucleotides, which correspond to the four DNA bases (A,C,T,G). Appropriate reaction conditions are created which allow the polymerase to copy the template by adding nucleotides to the 3' end of the primer. A multitude of reactions occur simultaneously on many primer copies to produce DNA fragments of varying length which all contain the radiolabel at appropriate nucleotides in each fragment, and which also irreversibly terminate in one of the four dideoynucleotides. This set of fragments is typically separated on a polyacrylamide slab electrophoresis gel in four lanes, one lane corresponding to each of the four dideoxynucleotide reaction mixtures. After the fragments have been separated, a photosensitive film is placed on the gel, exposed under appropriate conditions, and a DNA sequence is inferred from reading the pattern of bands on the film in order of their appearance in the four lanes from the bottom of the gel.

The modifications to the Sanger method according to the subject invention, include omitting the radiolabeled nucleotide and substituting reporter-labeled chain terminators for the unlabeled 2',3'-dideoxynucleotides. Reaction mixtures will now contain fragments which are irreversibly labeled on their 3' ends with an appropriate reporter that corresponds to each of four DNA bases. The reaction mixtures are combined and electrophoretically separated. Sequence is inferred by the order of appearance of distinguishable reporters associated with each fragment by the methods of this invention.

Figure 6:
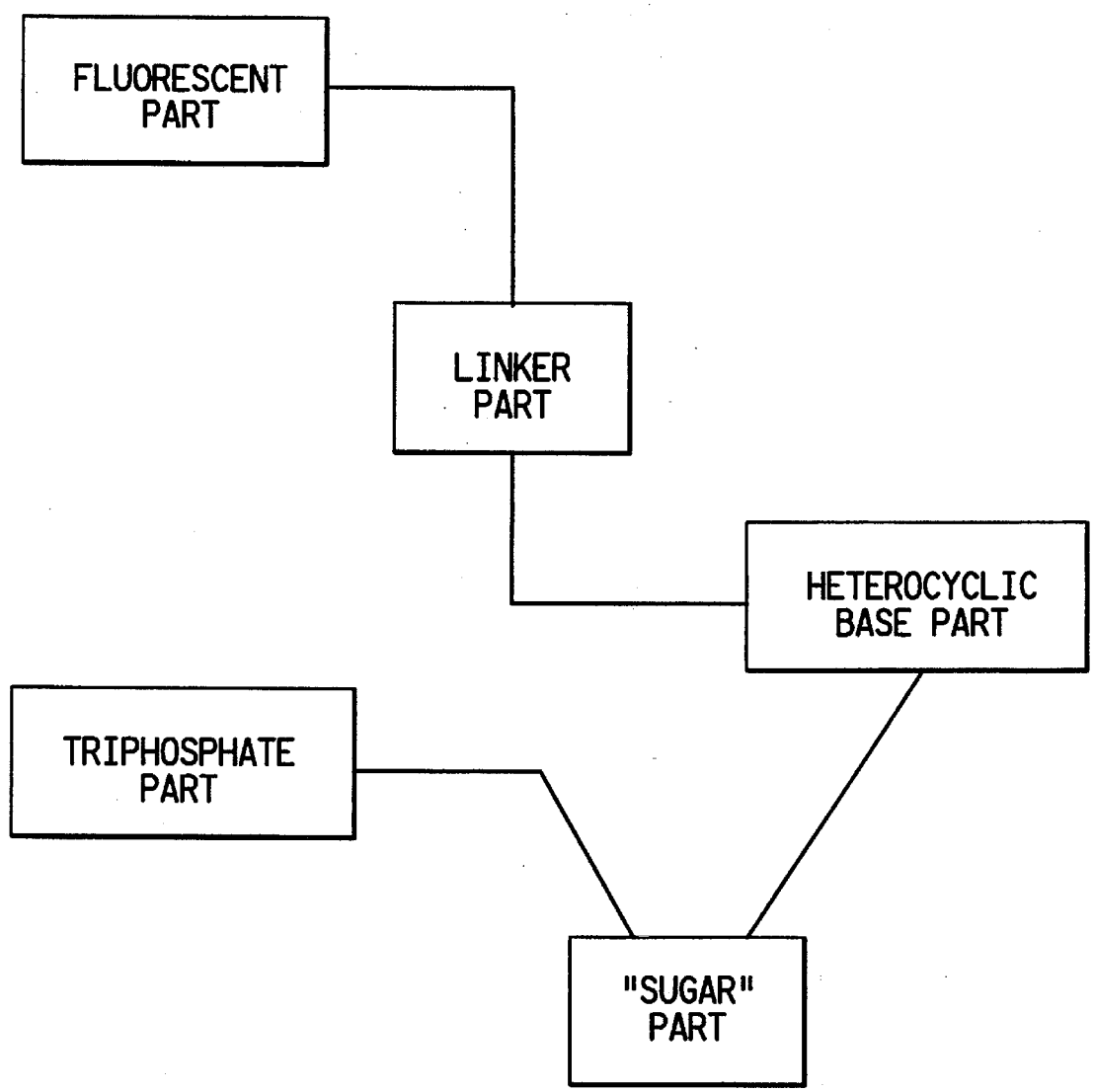
FIG. 6 is a block diagram of a fluorescence-labeled chain terminator and FIG. 7 shows the relationship of the dye emission radiation and the passbands of two filters used to replace the dichroic filter.

To delineate the structural scope and rationale of the reporter-labeled chain terminators used herein, it is useful to break the structure down into five components illustrated schematically in FIG. 6. A fluorescence-labeled chain terminator, for example, contains (i) a triphosphate part (ii) a "sugar" part, (iii) a heterocyclic base part, (iv) a linker part, and (v) a reporter part, where the reporter is a fluorescent compound.

It should be apparent from the preceding description that the term "chain terminator" is generic to the process of DNA sequencing with the Sanger methodology. The improved process of this invention utilizes more specialized varieties of chain terminators which advantageously also have a reporter attached to them. These novel compounds can be differentiated from generic chain terminators in that the latter compounds typically contain only the triphosphate (i), "sugar" (ii), and heterocyclic base (iii) parts outlined above. The chain terminators of this invention will be termed "reporter-labeled chain terminators," and typically contain all five parts described hereinafter.

Triphosphate Part

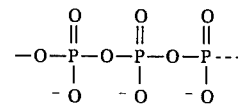

The triphosphate part or a close analog (e.g., alpha-thiotriphosphate) is an obligate functionality for any enzyme substrate, chain terminating or otherwise. This functionality provides much of the binding energy for the substrate and is the actual site of enzyme-substrate reaction.

Sugar Part

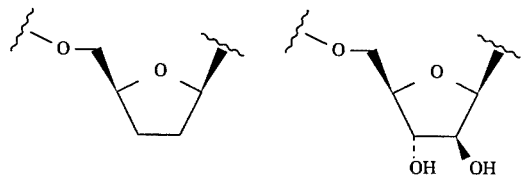

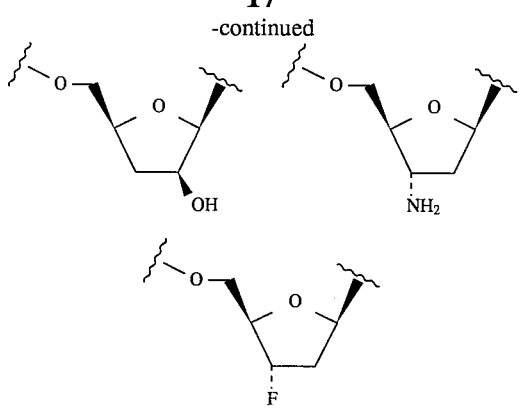

The "sugar" part corresponds to the 2'-deoxyribofuranose structural fragment in the natural enzyme substrates. This portion of the molecule contributes to enzyme recognition and is essential for maintaining the proper spatial relationship between the triphosphate part and the heterocyclic-base portion. One requirement of a chain-terminator is that when the "sugar" part is a ribofuranose, the 3'-position must not have a hydroxy group capable of being subsequently used by the DNA polymerase. The hydroxy group must be absent, replaced by another group, or otherwise rendered unusable. Alternatively, a ribofuranose analog could be used, such as arabinose, for the "sugar" part. The existing art shows that a number of modified furanose fragments may serve this function including: 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl [F. Sanger et al., *Proc. Nat. Acad. Sci. USA*, 74, 5463–5467 (1977): Z. G. Chidgeavadze et al., *Nuc. Acids Res.*, 12, 1671–1686 (1984): and Z. G. Chidgeavadze et al., *FEBS Lett.*, 183, 275–278 (1985)].

Heterocyclic Base Part

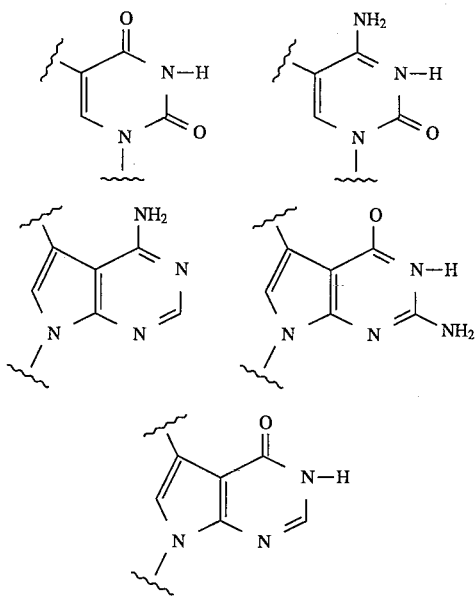

The heterocyclic-base part functions as the critical recognition element in nucleic acids that acts as a hydrogen-bonding acceptor and donor in a particular spatial orientation. These base elements are essential for incorporation of the appropriate nucleotide directed by the template with the high fidelity necessary for accurate sequencing. This structural part also carries the reporter. The art shows that the 5-position on the pyrimidines and the 7-position on purines may carry even a relatively bulky substituent without significantly interfering with overall binding or recognition [R. M. K. Dale et al., *Proc. Nat. Acad. Sci. USA*, 70, 2238–2242 (1973)]. Thus, preferred heterocyclic-base parts include: uracil, cytosine, 7-deazaadenine, 7-deazaguanine, and 7-deazahypoxanthine. The unnatural 7-deazapurines are employed so that the reporter may be attached without adding a net charge to the base portion or destabilizing the glycosidic linkage. Therefore, the natural purines do not serve as suitable heterocyclic base parts because they acquire net charge and quickly degrade after the alkylation reactions typically used to prepare reporter-labeled chain terminators. In addition, other heterocyclic bases having similar functional groups may be used.

Linker Part

The linker may be simply an amino group alone or a chain with a backbone containing such atoms as carbon, nitrogen, oxygen, or sulfur.

The linker is preferably an alkynylamino group in which one end of the triple bond is attached to an amine through a substituted or unsubstituted diradical moiety, $R_1$, of 1–20 atoms; the other end of the triple bond is covalently attached to the heterocyclic base at the 5-position for pyrimidines or the 7-position (purine numbering) for the 7-deazapurines. The amine nitrogen of the alkynylamino group is attached to a reactive functional group (e.g., carbonyl) on the fluorescent label. The linker must not significantly interfere with binding to or incorporation by the DNA polymerase. The diradical moiety can be straight-chained alkylene, $C_1$–$C_{20}$, optionally containing within the chain double bonds, triple bonds, aryl groups or heteroatoms such as N, O or S. The heteroatoms can be part of such functional groups as ethers, thioethers, esters, amines or amides. Substituents on the diradical moiety can include $C_1$–$C_{16}$ alkyl, aryl, ester, ether, amine, amide or chloro groups. Preferably, the diradical moiety is straight-chained alkylene, $C_1$–$C_{10}$; most preferably the diradical is —$CH_2$—. A more detailed description of the linkers most appropriate for use in the reporter-labeled chain terminators of this invention can be found in copending patent application by Hobbs et al.

Reporter Part

The preceding disclosure emphasizes the utility of a detection means which is particularly adapted to measurement of closely spaced spectra preferably of a set of fluorescent reporters as the emitting species. However, other species which emit radiation with closely spaced spectra can also be used to label DNA fragments. Several criteria can be identified for selection of appropriate reporter species to perform the methods of this invention. These criteria include:

efficient excitation by a monochromatic source and a strong, distinguishable emission response;

presence of a chemically reactive functional group capable of covalent attachment either directly or indirectly to nucleotide chain terminators or their analogs;

relatively small mass to minimize perterbation of steric relationships in oligonucleotide fragments:

charge and size characteristics which resemble those in other members of a chosen group or set of reporters selected for differentiation of chain terminators;

stability in a wide range of sample preparation, reaction and fragment separation conditions of pH, ionic strength, and temperature with respect to physical integrity and detection characteristics;

properties which have minimal deleterious effect on the production of or separation of DNA sequencing fragments.

Appropriate reporter species may be found in several categories of materials which can function with the above-mentioned properties. Among them are chromophores, fluorophores, chemiluminescers, spin labels, and electron dense materials. Detection of each of these species of materials can also be accomplished by a variety of means. For example, fluorescent species emissions can be detected as discussed previously in a manner that differentiates spectral distributions. In alternate fluorescent detection systems, additional species properties such as polarization and differential time-resolution can be employed to uniquely identify fragments having labeled DNA chain terminators corresponding to each base. The detection means selected can be optimized by known methods to maximize the signal-to-noise ratio and achieve acceptable sensitivity by minimizing background or extraneous signals. The unique properties and advantages of this invention are achieved by coupling an appropriate detection means with the reporter-labeled chain terminator in sequencing DNA.

In similar fashion, conventional photometry can be used to detect chromophores meeting the requirements of reporters in the methods of this invention. Four unique chromophores can be selected, which may also possess fluorescent properties, to be incorporated on chain terminators to introduce reporters detectable by a number of means, including absorption and photon counting spectrophotometry. A typical example of chromophores which may be useful are 2,4-dinitrophenol and its derivatives. Appropriate substitutions can result in different emission characteristics under a given set of conditions that are similar, which allows their detection by the apparatus previously described with little modification.

Luminescent reporters are differentiated from fluorescent reporters in the period of time required to re-emit incident radiation. Fluorescent reporters generally re-emit absorbed incident energy on the order of $10^{-8}$ to $10^{-3}$ seconds. The term "phosphorescent" is also often used to refer to compounds which are luminescent and the terms are generally used interchangeably. These compounds take longer to re-emit incident absorbed energy than fluorescent compounds. Typical luminescent reporters are derivatives of 2,2'-dihydroxybiphenyl-5,5'-diacetic acid, for example 2,2'-dihydroxy-3,3'-dimethoxybiphenyl-5,5'-diacetic acid, 2,2'-dihydroxybiphenyl-5,5'-dialanine, 2,2'-dihydroxybiphenyl-5,5'-diethylamine, etc.

Additional reporter species can be covalently attached to chain terminators that serve as electron dense reagents, such as colloidal gold particles. These materials can be used in an imaging system capable of detecting small changes in transmissive properties of light incident on an electrophoresis gel lane. Spin labels may also be used with appropriate detectors to uniquely label each chain terminator to make base assignments. The complexity of detection means in these instances may require the simplification of maintaining separate samples for each reporter-labeled chain terminator, rather than combining them into one sample before subjecting the sample(s) to a separation means.

It should be apparent to one skilled in the art that appropriate means to detect a combination of the above mentioned reporters can be readily devised to further differentiate the four reporter-labeled nucleotide chain terminators in a given system. This is especially applicable with the compounds covalently attached to chain terminators having both strong fluorescent and absorption properties. However, any combination of the above reporters which are selected for use according to the desirable properties already disclosed, can be used in systems having a complementary array of detection means.

In the more specific instance of the preferred embodiment of this invention, the fluorescent part provides detectable, emitted radiation following excitation by absorption of energy from an appropriate source such as an argon ion laser. It is desirable to have a unique fluorescent reporter for each DNA base encountered in sequencing applications and a set of four distinguishable fluorescent reporters is generally adequate.

A family of reporters which are useful in the DNA sequencing methods of this invention was devised especially for this purpose and is based on the known dye 9-carboxyethyl-6-hydroxy-3-oxo-3H-xanthene. Other dyes are known which are also derived from this parent compound. S. Biggs et al., *J. Chem. Soc.*, 123, 2934–2943 (1923) disclosed the preparation of several succinylfluorescein derivatives presumed to have bromine substitutions at either two or four (succinyleosin) positions in the resorcinol ring structure. Additional derivatives bearing dinitro and tetranitro substituents on succinylfluorescein were also prepared. These dyes were apparently prepared by simpler and more efficient methods over previous processes. However, no relationship of these dyes was disclosed and no significant characterization of their physical properties, including their emission spectra, was performed. This family of fluorescent reporters found useful for DNA sequencing by the methods of this invention has the general structure

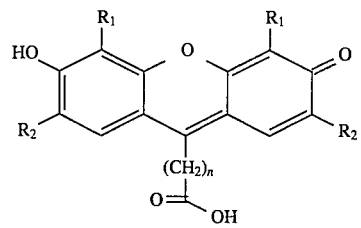

where n is 2 or 3 and $R_1$ and $R_2$ are H, lower alkyl, lower alkoxy, halo, and cyano. These materials are easily prepared by condensing either succinic or glutaric anhydride with the appropriate substituted resorcinol in methanesulfonic acid. This is a modification of the procedure reported by Biggs et al. for the preparation of the parent compound.

P. Khanna et al. [U.S. Pat. No. 4,481,136 (1984)] have described a class of compounds that include the structure 1 when $R_2$ is alkyl and $R_1$ is H and their use in the preparation of fluorescent antigen conjugates. While their individual use in fluorescent immunoassays is demonstrated, there is no indication of a utility requiring a family of such dyes or of any application to DNA sequencing.

The xanthene dyes are understood to be capable of existing in several different, generally interconvertible molecular forms. These forms, indicated below for the parent (1, n=2, $R_1=R_2=H$) are designated the quino-, delta-, spiro-, and leucoforms. The form that is observed in a given situation will be determined by the nature of n, $R_1$, and $R_2$, and by conditions such as temperature, solvent, pH, and crystal form. For clarity and convenience, only the quino- form will be used in naming and drawing structures.

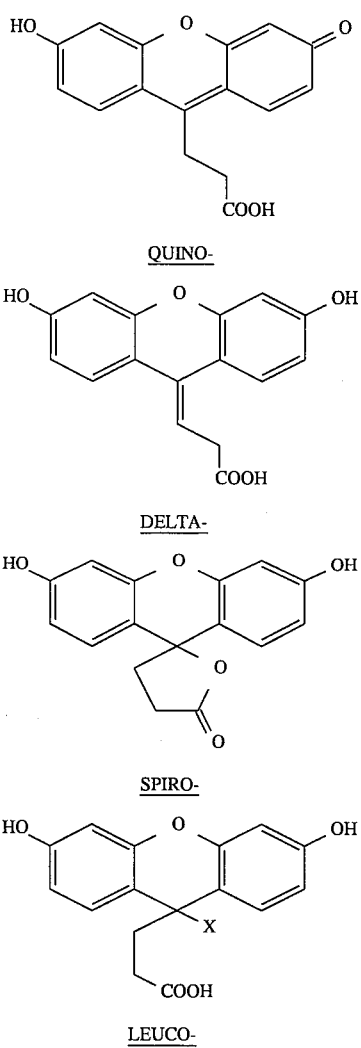

QUINO-

DELTA-

SPIRO-

LEUCO-

The actual fluorescent species is the dianion 2, formally derived from the quino- form. This species will generally predominate in aqueous solution above pH 7. The dianion derived from the parent dye (n=2, $R_1=R_2=H$) is very well suited to excitation by an argon ion laser operating at 486 nm. At pH 8.2 this species shows an absorption maximum at 487 nm with an absorption coefficient of about 72,600. The species emits at 505 nm with an efficiency comparable to that of fluorescein (quantum yield about 0.9).

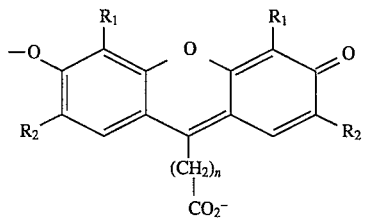

A set of four distinguishable fluorescent dyes can be generated by inducing small changes in the emission maximum of the parent chromophore through changes in the nature of the substituents $R_1$ and $R_2$. The correspondingly small differences in the absorption spectra maintain efficient excitation with an argon ion laser operated at 486 nm. By limiting the choice of $R_1$ and $R_2$ to relatively small substituents carrying no net charge one can insure that differential effects on the electrophoretic mobility, when the dyes are attached to DNA fragments, will be small.

A preferred set of such dyes suitable for DNA sequencing is: (structure 1, n=2, 1) $R_1=R_2=H$, abs. 486 nm, emis. 505 nm; 2) $R_1=H$, $R_2=CH_3$, abs. 494 nm, emis. 512 nm; 3) $R_1=CH_3$, $R_2=H$, abs. 500 nm, emis. 519 nm; 4) $R_1=R_2=CH_3$, abs. 509 nm, emis. 526 nm. The dye with the longest wavelength absorption maxima shows an excitation efficiency of about 50%. These four dyes are easily detected and distinguished at concentrations suitable for DNA sequencing.

Dye Attachment to Chain Terminators

Covalent attachment of these xanthene dyes is made through the carboxylic acid functionality, via an amide bond with a linker amine group. It is useful to introduce chemical protecting groups to lock the dyes into a suitable form and minimize side-reactions during coupling.

Reaction of the dye (1) with an alkyl or aryl acid anhydride (R') in pyridine, followed by treatment with an alkyl alcohol (R") in excess, affords a new composition, the protected dye (3) which bears acyloxy groups at the 3- and 6-positions and an alkoxy group (derived from the alcohol) at the 9-position. Compounds where the acyl group is acetyl and the alkoxy group is ethoxy are easy to prepare and show good stability, crystallinity, and organic solubility. Brief treatment with concentrated aqueous ammonia regenerates the free dye.

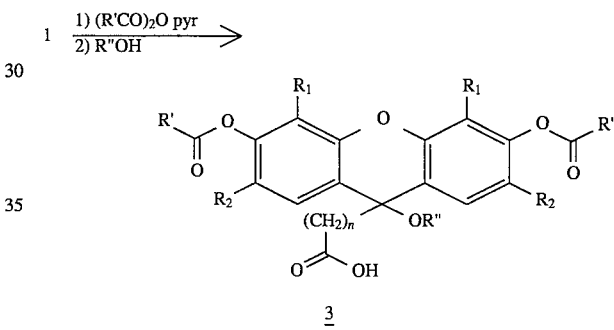

The protected dyes (3) may be coupled to amines via the carboxyl group using any one of a number of standard procedures. Amide bonds are preferred because they are stable, easy to form, and compatible with aqueous systems. The active species in these procedures is generally an intermediate of structure 4 where —X is a good leaving group.

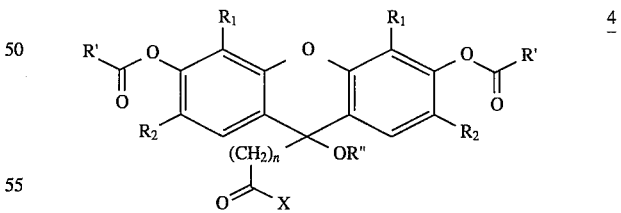

These active species are usually generated and coupled in situ but in some cases the intermediates can be isolated and purified. One particularly useful class of isolable, activated intermediates is the NHS esters 5. The compounds are easily prepared by treating the protected dyes 3 with an appropriate carbodiimide, such as N,N-dicyclohexylcarbodiimide, or preferably 1-(3-dimethylaminopropyl)-3-ethylcarbodiimide hydrochloride, in the presence of N-hydroxysuccinimide. They are stable, highly crystalline compounds which will react cleanly with primary and secondary amines in a variety of solvents. The primary and secondary amines are contributed by the material of interest to be analyzed in the system of this invention. These materials are typically dideoxynucleotides or their analogs containing the desired deazapurine and pyrimidine bases useful in the modified Sanger DNA chain extension protocol.

The NHS esters 5 may be used directly for coupling to a wide variety of secondary amines. Deprotection of the product with aqueous ammonia affords a dye-labeled amine derivative 6 which shows full fluorescence intensity.

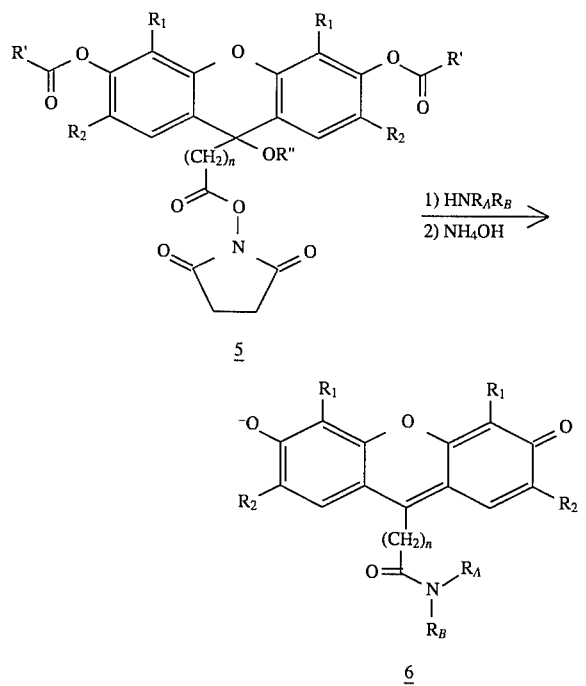

Coupling of an NHS ester 5 to primary amines is rapid and clean but deprotection generally affords a labeled amine which displays reduced fluorescence intensity. This is attributable to a partial equilibration of the fluorescent product 7a to the nonfluorescent spirolactam form 7b. The degree of equilibration is solvent, pH, and amine dependent. This problem can be alleviated by inserting a spacer between the dye and the amine. The spacer can be selected from diamines, diacids, or from molecules bearing secondary amines and carboxylic acids. Preferred spacers contain reactive amines which can form amide bonds with dye carboxyl groups. The spacer is associated primarily with the reporters, particularly the fluorescent dyes, and it functions to move the reactive amine away from the dye in order to prevent cyclization to the spirolactam form. It is also consistent with observation that the spacer functions to extend the dye farther from the DNA polymerase active site. This extension may improve the incorporation of reporter-labeled chain terminators into DNA fragments.

In contrast, the coupling of an NHS ester 5 to a preferred secondary amine affords a species which does not show appreciable cyclization to the spirolactam form but which carries a carboxylic acid for activation and coupling to the amine of interest.

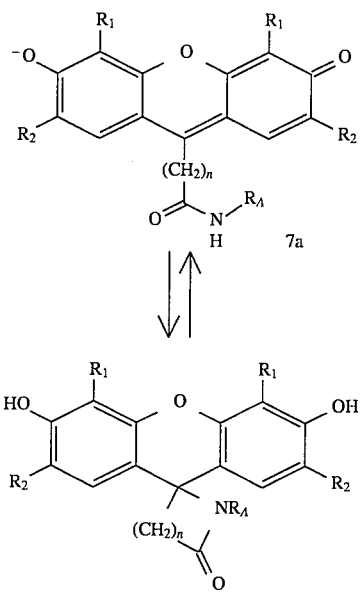

For example, a simple and effective spacer can be constructed from the amino acid sarcosine. Coupling of an NHS ester (5) to sarcosine benzyl ester followed by removal of the benzyl ester affords a carboxylic acid of the structure 8. As with the protected dyes (3) themselves, these carboxylic acids (8) can be coupled to amines using any one of a number of standard methods. Again, NHS esters of the structure 9 are isolable and particularly useful in this context.

Coupling of NHS esters 9 to amines followed by deprotection in aqueous ammonia affords dye-labeled amine derivatives of general structure 10 which are fully fluorescent.

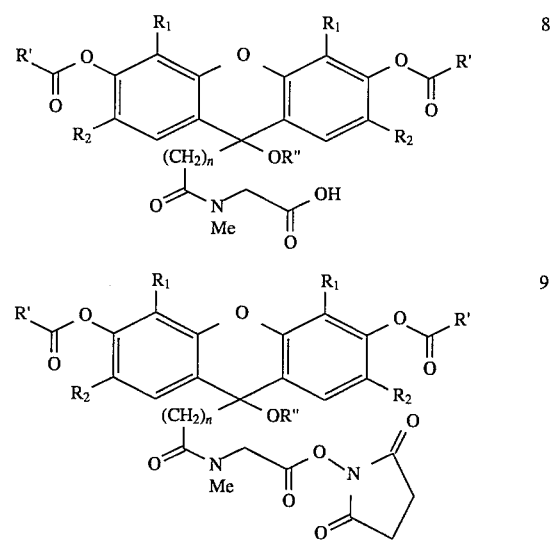

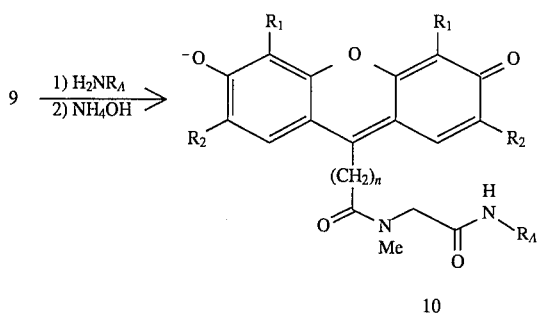

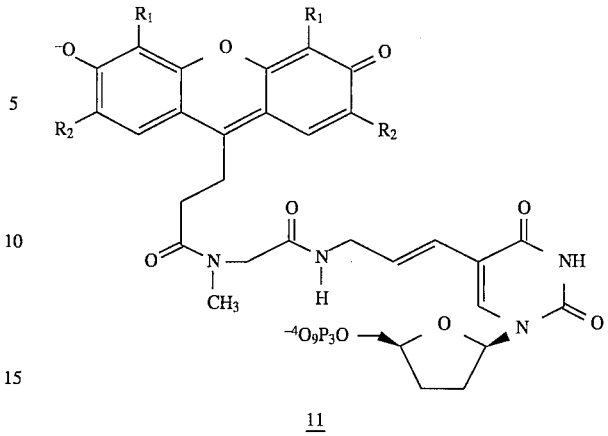

As a general rule, it would be preferable to design or obtain a material of interest that contained a primary amine, which could be reached with an appropriate spacer. The insertion of the spacer is believed to prevent cyclization reactions. Secondary amines can be used but do not react as rapidly or as efficiently as primary amines.

A representative fluorescence-labeled-chain-terminator is 11. This material can be constructed via a convergent route. 2',3'-Dideoxyuridine is prepared from commercially available 2'-deoxyuridine in 5 steps [K. E. Pfitzner et al., *J. Org. Chem.*, 29, 1508–1511 (1964)]. The 5'-triphosphate is prepared directly adapting the one-vessel procedure of J. L. Ruth et al., *Mol. Pharmacol.*, 20, 415–422 (1981). A 3-amino-1-propen-1-yl linker is appended to the 5-position on the heterocyclic-base through an adaptation of the sequence of reactions described by P. Langer et al., *Proc. Nat. Acad. Sci USA*, 78, 6633 (1981) and *Eur. Pat. Appl.* #82301804.9 (1982). Reaction of 5-(3-amino-1-propen-1-yl)-2',3'-dideoxyuridine-5'-triphosphate with the NHS ester 9 (N=2, $R_1$=$R_2$=H) followed by deprotection by brief treatment with aqueous ammonia affords the novel fluorescence-labeled-chain-terminator 11.

Compound 11 can substitute for ddTTP in the modified Sanger protocol. A full set of four chain terminators can consist of 11 and three analogues with different heterocyclic base and fluorescent parts. Preparation of the three analogues to substitute for the remaining non-labeled chain terminators of the modified Sanger protocol involves replacement of the heterocyclic base part of 11 (uracil) by cytosine (for ddCTP), 7-deazaadenine (for ddATP), and 7-deazaguanine (for ddGTP). The fluorescent part can be altered by changing the aromatic substituents $R_1$ and $R_2$ from both H (in 11) to, respectively, $CH_3$ and H, H and $CH_3$, and both $CH_3$. The compounds are prepared through routes similar to that described for 11.

It has been found that replacement of the 3-amino-1-propen-1-yl linker with a 3-amino-1-propyn-1-yl linker affords functionally equivalent reporter-labeled chain terminators that can be prepared more easily. The use of a propynyl linker allows preparation of more stable reporter-labeled chain terminators in higher yield than those prepared with the propenyl linker. Another advantage is that the propynyl linker is more regioselectively attached to nucleotide bases than the propenyl linker.

Therefore, the preferred reporter-labeled chain terminators for use in the Sanger chain extension method as modified by this invention are 12, 13, 14, and 15.

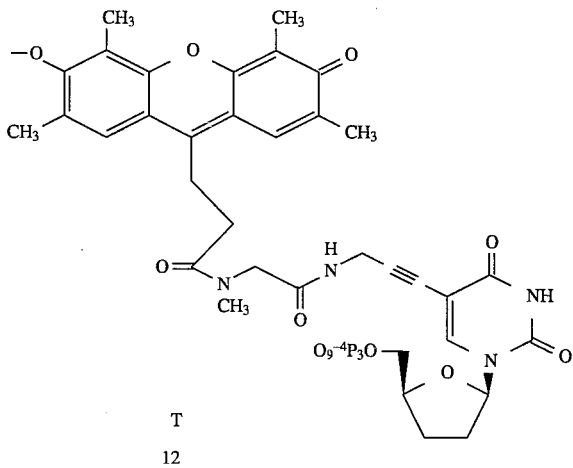

-continued

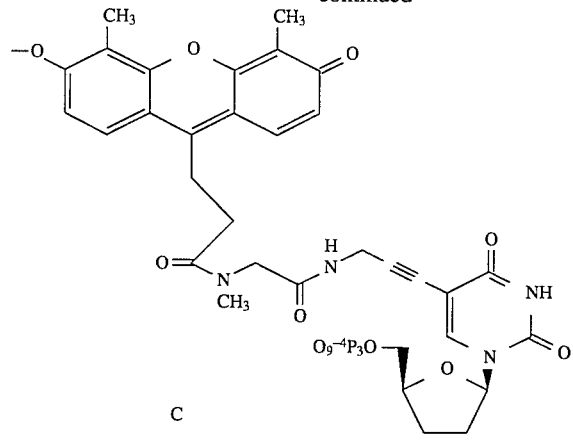

C
13

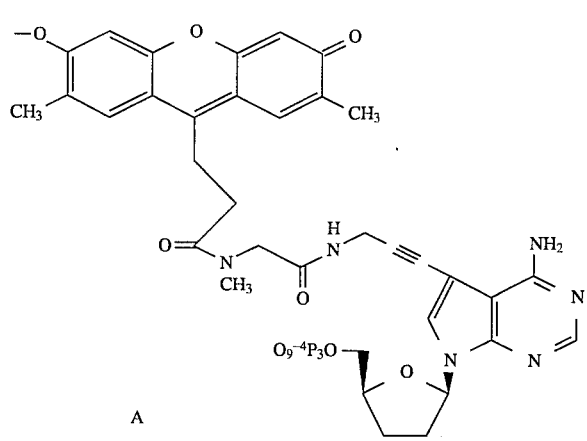

A
14

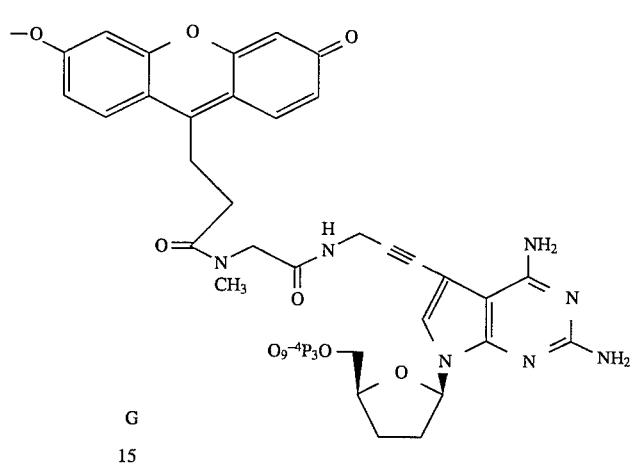

G
15

Further, it is expected that once a fluorescent dye is covalently coupled to a deazapurine or pyrimidine base through a linker and optional spacer, that its nominal emission maximum will shift toward a somewhat longer wavelength. This effect depends to an extent upon the nature of the base and upon the conditions of measurement such as pH, ionic strength, solvent, separation medium etc. Alternatively, one factor which does not appear to influence the emission characteristics of the fluorophores is the nature of the adjacent nucleosides in the DNA fragment containing the fluorescently-labeled chain terminator. Emissions of a given fluorophore appear to remain constant when its chain terminator is enzymatically coupled next to any of the pyrimidines and purines. For example, the reporter-labeled chain terminators disclosed above have fluorophores which emit maximally at 515 nm (12), 524 nm (14), 530 nm (13), and 536 nm (15) after 488 nm excitation. Under similar conditions of measurement, these fluorophores in the uncoupled state free in solution, had nominal emission maxima of 505 nm, 512 nm, 519 nm, and 526 nm, respectively. These shifts in emission maxima are easily measured and within routine experimentation to determine. Characterization of this distribution of emission maxima, in turn, allows one to select the desired reflection/transmission characteristic of the dichroic filter or its equivalent in the system of this invention.

The choice of DNA synthesizing enzyme will be largely determined by the specific structure of the chain-terminator. For example, compound 11 fails to give sequence-specific terminations with the Klenow fragment of DNA polymerase I enzyme but with AMV reverse transcriptase or bacteriophage T7 polymerase, terminations virtually identical to those observed with ddTTP (as judged using conventional $^{32}$P labeling) are obtained at comparable concentrations.

The chain-extension/termination reactions can be carried out in separate vessels or in a single vessel depending on the circumstances (e.g., range of terminations desired, degree of automation involved). The fluorescent-labeled chain-terminator and dNTP concentrations are adjusted to give a suitable distribution of sequencing fragments. The fluorescent-labeled DNA sequencing fragments show greater stability than their $^{32}$P labeled counterparts and may be electrophoretically analyzed immediately or at a later time, unlike the $^{32}$P labeled fragments which decompose over time.

In addition to overcoming many of the inherent disadvantages of the prior art, the chain terminator labeling approach of this invention is also significant since it offers a number of operational advantages. Most importantly, terminator labeling firmly links the attached reporter with the base-specific termination event. Only DNA sequencing fragments resulting from bona fide termination events will carry a reporter. This eliminates many of the artifacts observed in conventional sequencing. This affords complete flexibility in the choice of sequencing vector since no special primers are involved. Automation is facilitated by the fact that the reporters are carried by the four low molecular-weight chain terminators of this invention, and can be selectively introduced in a single reaction. There are no inherent operational disadvantages: the problems with this approach are encountered in the design stage. In general, DNA polymerases are highly substrate selective. The four reporter labeled chain-terminating reagents must be carefully designed so that the attached reporter groups do not excessively interfere with the degree or fidelity of incorporation.

The high performance potential and numerous operational advantages render the reporter-labeled chain terminator approach the superior method for preparing reporter-labeled DNA sequencing fragments via the modified Sanger methodology.

Primer Labeling

While the dyes described herein are used to greatest advantage in the preparation of fluorescent-labeled chain terminators, they may also be used in the primer labeling approach. The superior performance of these materials with regards to detection, discrimination, and electrophoretic mobility would render this application a substantial improvement of the Smith et al. system.

In the Smith et al. approach, a protected, amino-derivatized nucleoside phosphoramidite was used to prepare a 5'-amino-5'-deoxyoligonucleotide using an automated synthesizer. This material was purified and then coupled in separate, non-automated reactions to four different dyes. The four dye-labeled oligonucleotides were purified and used as primers in a Sanger protocol which omitted the customary radiolabeled deoxynucleotide.

The availability of protected derivatives of the dyes described in this application (e.g., 3) allow one to design nucleoside phosphoramidites which are labeled with the protected dyes. When used in an automated synthesizer, such a reagent allows the final 5'-residue and the fluorescent reporter to be introduced simultaneously. This advantage allows the elimination of the need to carry out a manual coupling and extra purification.

A typical protected, dye-labeled nucleoside phosphoramidite reagent was constructed as follows. An NHS ester (5) was generated in situ and allowed to react with 5'-deoxy-5'-(methylamino)thymidine to afford a protected, dye-labeled nucleoside derivative 16. 3'-Phosphitylation using standard techniques ["Oligonucleotide Synthesis", Ed., M. J. Gait, IRL Press, Washington. D.C. (1984)] afforded the corresponding phosphoramidite 17.

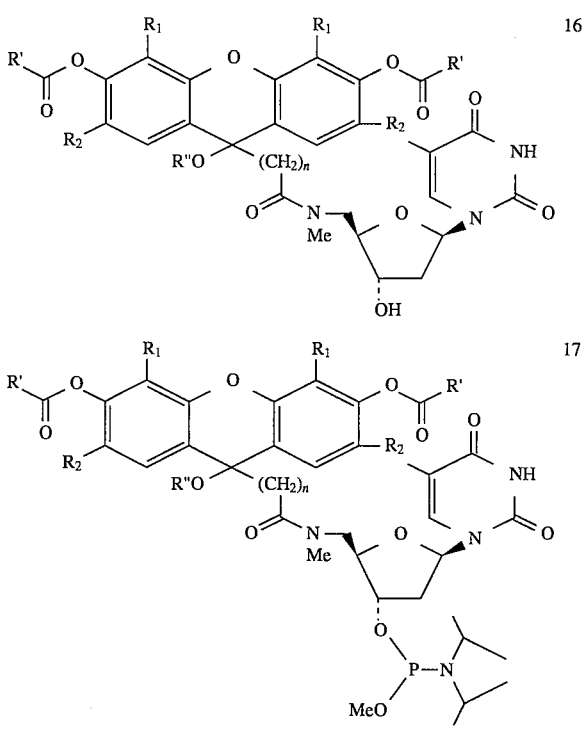

To construct a 5'-dye-labeled oligonucleotide to serve as a primer, a sequence with a 5'-terminal T residue is chosen. The automated synthesis is carried out as usual except that 17 is used as the final phosphoramidite reagent. [(Since no dimethoxytrityl (DMT) protecting group is present the final acid treatment can be eliminated.] The treatment with aqueous ammonia that releases the oligonucleotide from the solid support also serves to deprotect the dye. Deprotection is complete following the prolonged ammonia treatment used to deprotect the nucleotide bases. Standard preparative gel electrophoresis affords the dye-labeled oligonucleotide.

This approach does not circumvent the problems inherent in a primer labeling approach but should offer superior performance to the primers used in the Smith et al. system. Differential shifts in electrophoretic mobility should be minimized and detection/discrimination is greatly improved as described.

Other Dye Utilities

In addition to being useful in labeling DNA chain terminators or primers, these dyes are expected to be generally useful as fluorescent reporters. They can be used to label proteins, haptens, ribonucleic acids or other molecules of biological interest for use in immunoassays, specific binding assays, histochemical staining or any other uses requiring fluorescent labeling. Labeling of these substances is expected to be accomplished using known procedures analogous to that described above for the labeling of amines. These compositions are expected to be particularly useful when more than one fluorescent reporter is required in a given application, because they can be efficiently excited with a single monochromatic light source and detected as distinct reporters due to the shifted emission maxima. These are the same fluorescent properties which make these dyes useful as reporters in DNA sequencing. These dyes have the further advantage that each can be attached using the same chemical functionality, rather than the varied functions generally required with the known fluoresceins.

Acyclo Nucleoside Derivatives

Although the 2',3'-dideoxynucleoside triphosphates (ddNTP's) are used virtually exclusively as the chain terminators in conventional $^{32}$P sequencing, other sugar-modified derivatives, as mentioned above can also be used. These materials have the disadvantage (shared somewhat by the ddNTP's) of-being relatively difficult to prepare. An effective set of chain terminators having a less complex, more easily introduced "sugar" would be useful in both conventional $^{32}$P DNA sequencing and in fluorescence-based sequencing (with a fluorescent reporter linked to the heterocyclic base).

In the antiviral drug Acyclovir (acycloguanosine). a 2-hydroxyethoxymethyl group is substituted for the 2'-deoxyribofuranosyl group. Acyclovir is metabolized to the corresponding triphosphate (AcyGTP) in situ. AcyGTP has been reported to be both a competitive and a non-competitive inhibitor of various polymerases. It is also widely assumed to be a chain-terminating alternative substrate for these enzymes [P. V. McGuirt et al., *Antimicrob. Agents and Chemother.* 25, 507 (1984)] but its inhibitory component has complicated proper analysis of its substrate behavior. As the antiviral activity of Acyclovir can be explained by its ability to selectively inhibit vital polymerases, the rate of and products from processing of AcyGTP have never been completely characterized. (The corresponding acyclic triphosphates of thymidine, adenosine, and cytidine have been reported but their interactions with polymerases are even more poorly characterized.) Nowhere in the known art is there any evidence to suggest that acyclonucleoside triphosphates (AcyNTP's) will chain terminate DNA polymerization with anywhere near the efficacy and fidelity of compounds such as the ddNTP's. In particular, no AcyNTP has been reported to afford a sequencing ladder when used as a potential chain terminator in a DNA sequencing experiment.

In accordance with another aspect of this invention, acyclonucleoside triphosphates (AcyNTP's) have been demonstrated to be useful as chain terminators in DNA sequencing by the Sanger methodology.

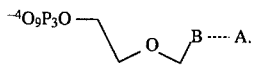

This was demonstrated by carrying out conventional Sanger sequencing ($^{32}$P nucleotide reporter) with the AcyNTP's substituting for the ddNTP's. The resulting sequencing ladders were virtually identical except that a higher concentration of AcyNTP (roughly 10×) was required to obtain a similar distribution of DNA fragments. The AcyNTP's were effective with both DNA Polymerase I (Klenow fragment) and AMV reverse transcriptase.

The AcyNTP's have the advantage of being more easily synthesized than the ddNTP's. This is not a major problem in conventional sequencing but it is significant when structurally complex, reporter-labeled chain terminators are being prepared. The use of the 2-oxyethoxymethyl group as a "sugar" part (as defined earlier) greatly simplifies reagent synthesis while maintaining acceptable performance.

EXPERIMENTAL

The following examples are offered by way of illustration and not by way of limitation.

All temperatures are in degrees centigrade. (25° refers to ambient or room temperature). All parts and percentages not otherwise indicated are by weight, except for mixtures of liquids which are by volume. The following abbreviations are employed: DMF—dimethylformamide; DMSO—dimethylsulfoxide; NHTFA—trifluoroacetamido group; TEAB—triethylammonium bicarbonate; Tris—tris(hydroxymethyl)aminomethane; SF—succinylfluorescein; NMR—nuclear magnetic resonance spectrum; IR—infrared spectrum: UV—ultraviolet spectrum or detection; TLC—thin layer chromatography on silica gel; HPLC—high pressure liquid chromatography; GC—gas chromatography: mp—melting point; mp d—melting point with decomposition; bp—boiling point. In reporting NMR data, chemical shifts are given in ppm and coupling constants (J) are given in Hertz. All melting points are uncorrected. Ion exchange resins were washed with appropriate aqueous and organic solvents prior to use. The identity of all compounds described herein was established by appropriate spectroscopic and analytical techniques. Unless otherwise noted, purification by chromatography on silica gel was performed as described by Still et al., *J. Org. Chem.*, 43, 2923–2926 (1978).

EXAMPLE 1

Preparation of a 505 nm fluorescent-labeled spacer-activated ester intermediate

A. Preparation of 9-(Carboxyethylidene)-3,6-dihydroxy-9H-xanthene (SF-505)

Resorcinol (33.0 g, 0.300 mol) and succinic anhydride (30.0 g, 0.300 mol) were placed in a round bottomed flask and purged with nitrogen. Methane-sulfonic acid (150 mL) was added and the solution was stirred at 65° C. for 2 hours under an atmosphere of nitrogen. The reaction mixture was added dropwise to rapidly stirred, ice-cooled water (1 L) with simultaneous addition of 50% aqueous sodium hydroxide to maintain pH 2.5 ±/0.5. The product which appeared as a granular precipitate was collected by filtration and rinsed with water (3×100 mL) then acetone (3×100 mL). The product was air-dried then vacuum-dried (vacuum oven) at 110° C. for 18 hours to afford a dark red powder (37.7 g, 88%).

An analytical sample was prepared by dissolving 1.0 g of product in 25 mL of hot 0.3N HCl. The precipitate which formed on cooling was removed by filtration and discarded. Dilute aqueous sodium hydroxide was added to raise the pH to 1.25. The resulting precipitate was collected by filtration, rinsed with water, air-dried, then vacuum-dried over $P_2O_5$ at 140° C. for 36 hours.

Anal: Calc. [C(16)H(12)O(5)] C 67.60, H 4.26. Found: C 67.37, H 4.34, 0.52% water (K-F). NMR (DMSO-$d_6$): (mostly spirolactone form) δ2.690 (t, J=8.6 hz, 2H): 3.07 (t, J=8.6 hz, 2H), 6.530 (d, J=1.8 hz, 2H): 6.676 (dd, J=8.7, 1.8 hz, 2H), 7.432 (d, J=8.7, 1.8 hz, 2H), 7.432 (d, J=8.7 hz, 2H), and 9.964 (s, 2H). Vis. abs. (pH 8.2; 50 mM aq Tris/HCl): max 486 nm (72,600).

B. Preparation of 9-(2-Carboxyethyl)-3,6-diacetoxy-9-ethoxy-9H-xanthene (Ac2EtSF-505)

SF-505 (29.3 g, 103 mmol) was added to ice-cold acetic anhydride (500 mL) followed by pyridine (100 mL). The mixture was stirred in ice for 20 minutes then added over 20 minutes to rapidly stirred, ice-cold water (7 L). After stirring for an additional 30 minutes, the intermediate product was filtered and resuspended in water (4 L) and stirred for another 30 minutes. The solid was collected by filtration, dissolved in absolute ethanol (1 L), and refluxed for 45 minutes. The solution was concentrated on a rotary evaporator to 200 mL which resulted in crystallization. The product was collected by filtration, air-dried, then vacuum-dried to afford pale-orange microcrystals (21.9 g, 51%).

Recrystallization from methylene chloride/cyclohexane gave colorless microcrystals. M.p.: 142°–143° C. Anal: Calc. [C(22)H(22)O(8)] C 6.63.76, H 5.35. Found: C 63.58, H 5.39. NMR (DMSO-$d_6$): δ1.035 (t, J=6.9 hz, 3H), 1.667 (m, 2H), 2.232 (m, 2H), 2.294 (s, 6H), 2.888 (q, J=6.9 hz, 2H), 7.0–7.1 (m, 4H), and 7.575 (d, J=9.1 hz, 2H).

C. Preparation of 9-(2-(N-Succinimidyloxycarbonyl-))ethyl)-3,6-diacetoxy-9-ethoxy-9H-xanthene (Ac2EtSF-505-NHS)

Ac2EtSF-505 (10.4 g, 25.1 mmol) was mixed with methylene chloride (300 mL) and 1-(3-dimethylaminopropyl)-3-ethylcarbodiimide hydrochloride (9.70 g, 50.6 mmol) and N-hydroxysuccinimide (4.32 g, 37.5 mmol) were added. The mixture was stirred for one hour and then washed with water (5×50 mL). The combined aqueous layers were back extracted with methylene chloride (50 mL) and the pooled organic layers were dried over sodium sulfate and stripped down. Trituration with ethanol (75 mL) followed by filtration and air-drying afforded the crude product as a light yellow solid (c. 10 g). This material was dissolved in methylene chloride (50 mL) and cyclohexane (50 mL) was added. One teaspoon of charcoal was added, the mixture was filtered, and the product was brought down with an additional portion of cyclohexane (100 mL). Collection by filtration, air-drying, and vacuum-drying afforded colorless crystals (6.94 g, 54%).

A second crystallization from ethanol afforded an analytical sample. M.p.: 162°–3° C. Anal: Calc. [C(26)H(25)N(1)O(10)] C 61.05, H, 4.93, N 2.74. Found: C 60.78, H 5.01, N 2.65. NMR (DMSO-$d_6$): δ1.056 (t, J=7.0 hz, 3H), 2.4–2.1 (m, 4H), 2.293 (s, 6H), 2.757 (s, 4H), 2.922 (q, J=7.0 hz, 2H), 7.069 (m, 4H), and 7.617 (p d, J=9.1 hz, 2H).

D. Preparation of 9-(2-(N-methyl-N-(benzyloxycarbonylmethyl)carboxiamido)ethyl)-3,6-diacetoxy-9-ethoxy-9H-xanthene (Ac2EtSF-505-Sar-OBn)

To a solution of sarcosine benzyl ester* (1.13 g, 6.31 mmol) in methylene chloride (50 mL) was added Ac2EtSF-505-NHS (2.58 g, 5.05 mmol) and 5% aq sodium bicarbonate solution (30 mL). The two-phase mixture was stirred rapidly for 20 hours. The layers were separated and the organic layer washed with 3×15 mL water, dried over sodium sulfate, and concentrated to 25 mL. The solution was diluted to 150 mL with cyclohexane, charcoal-treated, and reduced to 75 mL under a stream of nitrogen resulting in the precipitation of the product. The supernatant was decanted away and the residue coevaporated with methylene chloride to afford a colorless foam (1.70 g, 58%).

Extensive vacuum-drying afforded an analytical sample. Anal: Calc. [C(32)H(33)N(1)O(9)] C 66.77, H 5.78, N 2.43. Found: C 66.66, H 5.89, N 2.25. NMR (DMSO-$d_6$): (Shows 5:2 mixture of amide bond rotamers.) δ(major and minor) 1.040 and 1.018 (t, J=6.7 hz, 3H), 1.789 and 1.670 (m, 2H), 2.211 (m, 2H), 2.290 and 2.276 (s, 6H), 2.713 and 2.695 (s, 3H), 2.893 (q, J=6.7 hz, 2H), 3.963 (s, 2H), 5.075 and 5.039 (s, 2H), 7.044 (m, 4H), 7.324 (m, 5H), and 7.573 and 7.516 (p d, J=9.2 hz, 2H).

* Sarcosine benzyl ester p-tosylate salt (Adams Chemical Co.) was taken up in methylene chloride and washed repeatedly with 5% aqueous sodium bicarbonate, then water washed, dried over sodium sulfate, and stripped down.

E. Preparation of 9-(2-(N-Methyl-N-(N'-succinimidyl-oxycarbonylmethyl)carboxamido)ethyl)-3,6-diacetoxy-9-ethoxy-9H-xanthene (Ac2EtSF-505-Sar-NHS)

To a solution of Ac2ETSF-505-Sar-OBn (1.55 g, 2.69 mmol) in absolute ethanol (60 mL) was added 10% palladium on carbon (0.15 g). The mixture was stirred under balloon pressure of hydrogen for 30 minutes. The catalyst was removed by filtration and the ethanol stripped off to afford a syrupy residue.

This residue was dissolved in methylene chloride (85 mL) and N-hydroxysuccinimide (0.495 g, 4.30 mmol) and 1-(3-dimethylaminopropyl)-3-ethylcarbodiimide hydrochloride (1.12 g, 5.84 mmol) were added (4×25 mL). The solution was concentrated to 25 mL, diluted to 175 mL with cyclohexane, charcoal treated, and reduced in volume to 75 mL under a stream of nitrogen. The solid product was collected by filtration, air-dried, and vacuum-dried to afford a colorless powder (0.97 g, 62%).

Coevaporation with methylene chloride followed by extensive vacuum-drying at 40° C. removed traces of cyclohexane and afforded an analytical sample as an amorphous solid. Anal: Calc. [C(29)H(30)N(2)O(11)] C 59.79, H 5.19, N 4.81. Found: C 59.37, H 4.62, N 4.62, 0.93% water (K-F). NMR (DMSO-$d_6$): (Shows a 4:1 mixture of amide bond rotamers.) δ(major and minor) 1.034 (t, J=6.9 hz, 3H), 1.827 and 1.935 (m, 2H), 2.223 (m, 2H), 2.289 (s, 6H), 2.758 (s, 4H), 2.779 and 2.824 (s, 3H), 2.888 (q, J=6.8 hz, 2H), 4.333 and 4.473 (s, 2H), 7.043 (m, 4H), and 7.587 (per d, J=9.1 hz, 2H).

EXAMPLE 2

Preparation of a 512 nm fluorescent-labeled spacer-activated ester intermediate

A. Preparation of 4-Methylresorcinol 2,4-Dihydroxybenzaldehyde (33.97 gm, 0.246 mol) (recrystallized from toluene) was dissolved in spectroscopic grade 2-propanol (3 L) in a round bottom flask fitted with a gas inlet and a bubbler outlet. 10% Palladium on carbon (1.35 gm) was added followed by phosphoric acid (3 mL) and the mixture was sparged with nitrogen. The nitrogen flow was switched to hydrogen and the mixture was rapidly stirred with ice cooling. After 3 hours hydrogen uptake was complete and the catalyst was removed by filtration. The filtrate was stripped down to 200 mL and 200 mL of ethyl acetate was added. The solution was washed with 4×200 mL of water and the combined water extracts back-extracted with ethyl acetate. These organic extracts were water washed and the combined organic layers dried over sodium sulfate and stripped down to afford the product as a colorless crystalline solid (29.95 gm, 98%). M.p.: 106° C. (Lit. 106°–107° C. [J. C. Bell, W. Bridge, and A. Robertson, *J. Chem. Soc.*, 1542–45 (1937)]). NMR (DMSO-$d_6$): δ1.961 (s, Me), 6.076 (dd, H-6, J[5,6]=8 hz, J[2,6]=2 hz), 6.231 (d, H-2), 6.760 (d, H-5) 8.867 (s, OH), and 9.008 (s, OH).

B. Preparation of 9-Carboxyethylidene-3,6-dihydroxy-2,7-dimethyl-9H-xanthene (SF-512)

4-Methylresorcinol (25.8 g, 0.208 mol) and succinic anhydride (20.8 g, 0.208 g) were placed in a round bottom flask and the flask was purged with nitrogen. Methanesulfonic acid (150 mL) Was added and the solution heated under nitrogen to 65° C. for 2 hours. The solution was added dropwise to 1 L of rapidly stirred, ice-cooled water with the simultaneous addition of 50% aq sodium hydroxide to maintain the pH at 2.25±0.25. The product was collected by centrifugation and washed with water (3×) and acetone (2×). The solid was air-dried, then vacuum-dried at 110° C. to afford a brick-red powder (24.1 g, 74%).

Purification was effected by allowing ethyl acetate to slowly diffuse into a solution of the product in dimethyl sulfoxide. The precipitate was collected by filtration, air-dried, then vacuum-dried. NMR (DMSO-$d_6$): (Shows pure delta form along with one mole each of water and dimethyl sulfoxide.) δ2.124 (s, 6H), 3.421 (d, J=7.2 hz, 2H), 5.769 (t, J=7.2 hz, 1H); 6.512 (s, 1H), 6.573 (s, 1H); 7.295 (s, 2H), 9.681 (s, 1H), 9.825 (s, 1H), and 12.346 (bs, 1H). Vis. abs. (pH 8.2 aq Tris): max 493.5 nm.

C. Preparation of 9-Carboxyethyl-3,6-diacetoxy-2,7-dimethyl-9-ethoxy-9H-xanthene (Ac2EtSF-512)

A sample of SF-512 (20.0 g, 64.0 mmol) was added to acetic anhydride (350 mL) followed by pyridine (80 mL). This was stirred for 1 hour and then filtered to remove traces of unreacted dye. The filtrate was poured into 3.5 L of rapidly stirred water. The solid intermediate was collected by filtration, resuspended in 2 L cold water, stirred for 15 minutes, then recollected and air-dried to afford the spirolactone intermediate (20.8 g). This was dissolved in absolute ethanol (600 mL) and refluxed for 45 minutes. The solution was charcoal-treated and concentrated to 300 mL. The product was collected by filtration, rinsed with cold ethanol (2 ×50 mL), air-dried, and then vacuum-dried to afford colorless microcrystals (14.9 g, 53%). M.p.: 143° C. Anal: Calc. [C(24)H(26)O(8)] C 65.15, H 5.92. Found: C 65.31, H 5.97. NMR (DMSO-$d_6$): δ1.027 (t, J=6.9 hz, 3H), 1.628 (m, 2H), 2.136 (s, 6H), 2.207 (m, 2H), 2.303 (s, 6H), 2.884 (q, 6.9 hz, 2H), 6.939 (s, 2H), and 7.417 (s, 2H).

D. Preparation of 9-(2-(N-Succinimidyloxycarbonyl)-ethyl)-3,6-diacetoxy-2,7-dimethyl-9-ethoxy-9H-xanthene (Ac2EtSF-512-NHS)

To a solution of Ac2EtSF-512 (9.42 g, 21.3 mmol) in methylene chloride (175 mL) was added N-hydroxysuccinimide (3.62 g, 31.5 mmol) followed immediately by 1-(3-dimethylaminopropyl)-3-ethylcarbodiimide hydrochloride (8.05 g, 42.0 mmol). The solution was stirred at room temperature for 2 hours. The mixture was washed with water (4×100 mL) and the aqueous washings back-extracted with methylene chloride (2×50 mL). The combined organic layers were dried over sodium sulfate and stripped down to an oil. Absolute ethanol was added and crystallization was induced by scratching. The product was collected by filtration, air-dried, then vacuum-dried to afford pale-orange microcrystals (9.80 g, 85%).

An analytical sample was prepared by dissolving 1 g in methylene chloride (10 mL) and adding cyclohexane (40 mL). Charcoal treatment followed by cooling and scratching induced crystallization affording a colorless crystalline solid. M.p.: 159° C. Anal: Calc. [C(28)H(29)N(1)O(10)] C 62.33, H 5.42, N 2.60. Found: C 62.06, H 5.71, N 2.39. NMR (DMSO-$d_6$): δ1.053 (t, J=6.9 hz, 3H), 2.149 (s, 6H), 2.304 (s, 6H), 2.1–2.4 (m, 4H), 2.747 (s, 4H), 2.920 (q, J=6.9 hz, 2H), 6.975 (s, 2H), and 7.464 (s, 2H).

E. Preparation of 9-(2-(N-methyl-N-(benzyloxycarbonylmethyl)carboxamido)ethyl)-3,6-diacetoxy-2,7-dimethyl-9-ethoxy-9H-xanthene (Ac2EtSF-512-Sar-OBn)

To a solution of sarcosine benzyl ester (0.72 g, 4.02 mmol) in methylene chloride (25 mL) was added Ac2EtSF-512-NHS (1.73 g, 3.21 mmol) and 5% aq sodium bicarbonate solution (20 mL). The two-phase mixture was stirred rapidly for 20 hours. The layers were separated and the organic layer washed with 3×15 mL water, dried over sodium sulfate, and concentrated to 10 mL. The solution was diluted to 60 mL with cyclohexane, charcoal-treated, and reduced to 25 mL under a stream of nitrogen resulting in the precipitation of the product. The supernatant was decanted and the colorless solid vacuum-dried (1.44 g, 74%).

Recrystallization from methylene chloride/cyclohexane with charcoal treatment afforded an analytical sample. M.p.: 150°–2° C. Anal: Calc. [C(34)H(37)N(1)O(9)] C 67.65 H 6.18 N 2.32. Found: C 67.42 H 6.08 N 2.33. NMR (DMSO-$d_6$): (Shows 5:2 mixture of amide bond rotamers.) δ(major and minor) 1.049 and 1.008 (t, J=6.8 hz, 3H), 1.747 and 1.66 (m, 2H), 2.144 and 2.115 (s, 6H), 2.18 (m, 2H), 2.314 and 2.303 (s, 6H), 2.694 (s, 3H), 2.907 and 2.884 (q, J=6.8 hz, 2H), 3.961 (s, 2H), 5.075 and 5.016 (s, 2H), 6.960 and 6.917 (s, 2H), 7.430 and 7.396 (s, 2H), and 7.30 (m, 5H).

F. Preparation of 9-(2-(N-Methyl-N-(N'-succinimidyl-oxycarbonylmethyl)carboxamido)ethyl)-3,6-diacetoxy-9-ethoxy-2,4,5,7-tetramethyl-9H-xanthene (Ac2EtSF-512-Sar-NHS)

To a suspension of Ac2EtSF-512-Sar-OBn (0.45 g, 0.745 mol) in absolute ethanol (20 mL) was added 10% palladium on carbon (0.05 g). The mixture was stirred under balloon pressure of hydrogen for 30 minutes. The catalyst was removed by filtration and the ethanol stripped off to afford a syrupy residue.

This residue was dissolved in methylene chloride (25 mL) and N-hydroxysuccinimide (0.129 g, 1.12 mmol) and 1-(3-dimethylaminopropyl)-3-ethylcarbodiimide hydrochloride (0.292 g, 1.52 mmol) were added. The mixture was stirred for 30 minutes and then washed with water (3×15 mL). The solution was dried over sodium sulfate, concentrated to 10 mL, diluted to 40 mL with cyclohexane, charcoal treated, and reduced in volume to 20 mL under a stream of nitrogen. The supernatant was decanted and the residue subjected to a second precipitation from methylene chloride to afford a colorless powder (0.27 g, 59%). Anal: Calc. [C(31)H(34)N(2)O(11)] C 60.98, H 5.61, N 4.59. Found: C 60.28, H 5.71, N 4.40, 1.08% water (K-F). NMR (DMSO-$d_6$): (Shows a 5:1 mixture of rotamers about the amide bond.) δ(major and minor) 1.043 (t, J=7.0 hz, 3H), 1.793 and 1.933 (m, 2H), 2.145 and 2.133 (s, 6H), 2.198 (m, 2H), 2.314 (s, 6H), 2.740 (s, 4H), 2.778 and 2.821 (s, 3H), 2.900 (q, J=7.0 hz, 2H), 4.334 and 4.469 (s, 2H), 6.960 and 6.925 (s, 2H0, and 7.441 (s, 2H).

EXAMPLE 3

Preparation of a 519 nm fluorescent-labeled spacer-activated ester intermediate

A. Preparation of 9-(2-Carboxyethylidene)-3,6-dihydroxy-4,5-dimethyl-9H-xanthene (SF-519)

2-Methylresorcinol (37.2 g, 0.300 mol) and succinic anhydride (30.0 g, 0.300 mol) were placed in a round bottomed flask and purged with nitrogen. Methanesulfonic acid (150 mL) was added and the solution was stirred at 65° C. for 4 hours under an atmosphere of nitrogen. The reaction mixture was added dropwise to rapidly stirred, ice-cooled water (1 L) with simultaneous addition of 50% aqueous sodium hydroxide to maintain pH 6.0±0.5. The finely divided solid was collected by centrifugation and rinsed with water (4×250 mL), each time resuspending, spinning down, and discarding the supernatant. The crude product was suspended in water (1 L) and sufficient aqueous sodium hydroxide (50%) was added to raise the pH to 10.2. The solution was filtered and the filtrate brought to pH 1.2 with concentrated HCl. The product was collected by centrifugation and rinsed with water (3×350 mL) and acetone (3×250 mL) as described above resulting solid was azeotroped with toluene, collected by filtration, and vacuum-dried at 110° C. to afford a brick-red powder (24.6 g, 53%). Anal: Calc. [C(18)H(16)O(5)] C 69.22 H 5.16. Found: C 68.95 H 5.30, 0.80% water (K-F). NMR (DMSO-$d_6$) (mostly delta form): δ2.164 (s, 3H), 2.177 (s, 3H), 3.376 (d, J=7.1 hz, 2H), 5.749 (t, J=7.2 hz, 1H), 6.642 (d, J=8.8 hz, 1H), 6.672 (d, J=8.8 hz, 1H), 7.216 (d, J=8.5 hz, 1H), 7.227 (d, J=8.5 hz, 1H), 9.602 (bs, 1H), and 9.758 (bs, 1H). Vis. abs. (pH 8.2; 50 mM aq Tris/HCl) max 500 nm (69,800).

B. Preparation of 9-(2-Carboxyethyl)-3,6-diacetoxy-4,5-dimethyl-9-ethoxy-9H-xanthene (Ac2EtSF-519)

SF-519 (15.0 g, 48.0 mmol) was added to acetic anhydride (250 mL) and the solid was pulverized. (Sonication is useful to disperse the highly insoluble SF-519.) The suspension was ice-cooled, pyridine (50 mL) was added, and the mixture stirred for 20 minutes. The solution was filtered and added in a slow but steady stream to rapidly stirred ice-cold water (4 L). After stirring for an additional 20 minutes, the intermediate product was filtered, resuspended in water (3 L), and stirred for another 25 minutes. The solid was collected by filtration and air-dried. The dried intermediate was dissolved in absolute ethanol (600 mL) and refluxed for 1 hour. The solution was concentrated on a rotary evaporator to 200 mL which resulted in crystallization. The product was collected by filtration, air-dried, then vacuum-dried to afford colorless microcrystals (12.13 g, 57%).

An analytical sample was prepared by precipitation from methylene chloride solution with cyclohexane. NMR (DMSO-$d_6$): δ1.033 (t, J=6.9 hz, 3H), 1.674 (m, 2H), 2.189 (s, 6H), 2.19 (m, 2H), 2.348 (s, 6H), 2.878 (q, J=6.9 hz, 2H), 7.006 (d, J=8.6 hz, 2H), and 7.399 (d, J=8.6 hz, 2H).

C. Preparation of 9-(2-(N-Succinimidyloxycarbonyl)-ethyl-3,6-diacetoxy-4,5-dimethyl-9-ethoxy-9H-xanthene (Ac2EtSF-519-NHS)

Ac2ETSF-519 (7.80 g, 17.6 mmol) was mixed with methylene chloride (175 mL) and N-hydroxysuccinimide (2.75 g, 23.9 mmol) and 1-(3-dimethylaminopropyl)-3-ethylcarbodiimide hydrochloride (7.00 g, 36.5 mmol) were added. The mixture was stirred for 90 minutes and then washed with water (5×100 mL). The combined aqueous layers were back extracted with methylene chloride (2×50 mL) and the pooled organic layers were dried over sodium sulfate and stripped down. Trituration with ethanol (100 mL) followed by filtration and air-drying afforded the product as a light yellow solid (7.45 g, 78%).

Two recrystallizations from cyclohexane/methylene chloride with charcoal treatment afforded an analytical sample. M.p.: 164°–5° C. Anal: Calc. [C(28)H(29)N(1)O(10)] C 62.33, H 5.42, N 2.60. Found.: C 62.17, H 5.47, N 2.48. NMR (DMSO-$d_6$: δ1.051 (t, J=7.0 hz, 3H), 2.4–2.1 (m, 4H), 2.191 (s, 6H), 2.337 (s, 6H), 2.715 (s, 4H), 2.912 (q, J=7.0 hz, 2H), 7.015 (d, J=8.6 hz, 2H), and 7.429 (d, J=8.6 hz, 2H).

D. Preparation of 9-(2-(N-methyl-N-(benzyloxy-carbonylmethyl)carboxamido)ethyl)-3,6-diacetoxy-4,5-dimethyl-9-ethoxy-9H-xanthene (Ac2EtSF-519-Sar-OBn)

To a solution of sarcosine benzyl ester (0.557 g, 3.11 mmol) in methylene chloride (19 mL) was added Ac2EtSF-519-NHS (1.30 g, 2.41 mmol) and 5% aqueous sodium bicarbonate solution (15 mL). The two-phase mixture was stirred rapidly for 18 hours. The layers were separated and the organic layer washed with 3×10 mL water, dried over sodium sulfate, and concentrated to 10 mL. The solution was diluted to 40 mL with cyclohexane, charcoal-treated, and reduced to 20 mL under a stream of nitrogen resulting the precipitation of the product as a sticky solid. The supernatant was decanted away and the residue coevaporated with methylene chloride to afford a colorless foam (0.97 g, 67%).

Extensive vacuum drying afforded an analytical sample. Anal: Calc. [C(34)H(37)N(1)O(9)] C 67.65 H 6.18 N 2.32. Found: C 67.43 H 6.37 N 2.32. NMR (DMSO-$d_6$) (Shows 5:2 mixture of amide bond rotamers.): δ(major and minor) 1.044 and 1.020 (t, J=7.0 hz, 3H), 1.824 and 1.714 (m, 2H), 2.17 (m, 2H), 2.195 and 2.169 (s, 6H), 2.346 and 2.337 (s, 6H), 2.720 and 2.691 (s, 3H), 2.889 (q, J=7.0 hz, 2H), 3.959 and 3.988 (s, 2H), 5.073 and 5.048 (s, 2H), 7.000 and 6.954 (d, J=8.6 hz, 2H), and 7.45–7.25 (m, 7H).

E. Preparation of 9-(2-(N-Methyl-N-(N'-succinimidyl-oxycarbonylmethyl)carboxamido)ethyl)-3,6-diacetoxy-4,5-dimethyl-9-ethoxy-9H-xanthene (Ac2EtSF-519-Sar-NHS)

To a solution of Ac2EtSF-519-Sar-OBn (1.35 g, 2.24 mmol) in absolute ethanol (50 mL) was added 10% palladium on carbon (0.13 g). The mixture was stirred under balloon pressure of hydrogen for 20 minutes. The catalyst was removed by filtration and the ethanol stripped off to afford a syrupy residue.

This residue was dissolved in methylene chloride (50 mL) and N-hydroxysuccinimide (0.39 g, 3.39 mmol) and 1-(3-dimethylaminopropyl)-3-ethylcarbodiimide hydrochloride (1.57 g, 8.19 mmol) were added. The mixture was stirred for 75 minutes and then washed with water (4×15 mL). The solution was dried over sodium sulfate, concentrated to 25 mL, diluted to 125 mL with cyclohexane, charcoal treated, and reduced in volume to 50 mL under a stream of nitrogen. The supernatant was decanted and the remaining oil taken up in methylene chloride (5 mL) and added dropwise to rapidly stirred cyclohexane (75 mL) to afford a colorless powder (0.587 g, 43%).

To provide an analytical sample a portion of the product was taken up in methylene chloride, dried over molecular sieves, evaporated under a stream of nitrogen, and finally dried in a drying pistol at 48° C. over phosphorus pentoxide for 20 hours. Anal: Calc. [C(31)H(34)N(2)O(11)]; C 60.98, H 5.61, N 4.59. Found: C 60.15, H 5.71, N 4.51, water (K-F) 1.51%. NMR (DMSO-$d_6$) (Shows a 4:1 mixture of amide bond rotamers.): δ(major and minor) 1.039 (t, J=6.9 hz, 3H), 1.841 and 1.945 (m, 2H), 2.19 (m, 2H), 2.194 (s, 6H), 2.345 (s, 6H), 2.767 and 2.744 (s, 4H), 2.778 and 2.825 (s, 3H), 2.888 (q, J=6.9 hz, 2H), 4.328 and 4.461 (s, 2H), 7.000 (d, J=8.6 hz, 2H), and 7.410 (d, J=8.6 hz, 2H).

EXAMPLE 4

Preparation of a 526 nm fluorescent-labeled spacer-activated ester intermediate

A. Preparation of 2,4-Dihydroxy-3-methylbenzaldehyde

Phosphorus oxychloride (80 mL, 0.86 mol) was added to a stirred mixture of N-methylformanilide (102 mL, 0.82 mol) in ether (250 mL). The mixture was stirred for 1 hour at room temperature and then cooled in ice. 2-Methyl resorcinol (Aldrich, 100 g, 0.81 mol) was added and the mixture was allowed to warm to room temperature while stirring overnight. The precipitated intermediate product was collected by filtration and rinsed with ether (3×). The intermediate was hydrolyzed by dissolving in a mixture of acetone (250 mL) and water (250 mL) and stirring for 30 minutes. Water (2 L) was added, the mixture was brought to a boil, and then allowed to cool and deposit crystalline product. This was recrystallized a second time from water (4 L) to afford pure product (70 g, 57%). M.p. 150° C. (Lit. 152°–3° C. [W. Baker et al., *J. Chem. Soc.*, 2834–5 (1949).].

NMR (DMSO-d$_6$): δ1.973 (s, 3H), 6.551 (d, J=8.5 hz, 1H), 7.428 (d, J-8.5 hz, 1H), 9.703 (s, 1H), 10.745 (s, 1H), and 11.592 (s, 1H).

B. Preparation of 2,4-dimethylresorcinol

A solution of 2,4-dihydroxy-3-methylbenzaldehyde (30.0 g, 197 mmol) with isopropanol (3 L) was ice-cooled in a 5 L 3-neck flask fitted with a magnetic stirrer. Phosphoric acid (4 mL) and 10% palladium on carbon were added and the solution was sparged with nitrogen, then hydrogen. When uptake was judged to be complete (c. 1.5 hour) the solution was again sparged with nitrogen and then filtered through Celite®. The solvent was stripped off, the residue taken up in ethyl acetate, and the resulting solution washed with water (4×100 mL). The water washes were back-extracted with ethyl acetate and the combined organic layers dried over sodium sulfate and stripped down. Sublimation (95°, 0.05 torr) afforded a colorless solid (19.6 g, 72%). M.p. 107°–8° C. (Lit. 108°–109° C. [W. Baker et al., *J. Chem. Soc.*, 2834–5 (1949).]). NMR (DMSO-d$_6$): δ1.969 (s, 3H), 2.037 (s, 3H), 6.220 (d, J=8.1 hz, 1H), 6.637 (d, J=8.1 hz, 1H), 7.929 (s, 1H), and 8.785 (s, 1H).

C. Preparation of 9-(2-Carboxyethylidene)-3,6-dihydroxy-2,4,5,7-tetramethyl-9H-xanthene (SF-526)

2,4-Dimethylresorcinol (28.4 g, 0.205 mol) and succinic anhydride (20.0 g, 0.200 mol) were placed in a round bottomed flask and purged with nitrogen. Methanesulfonic acid (231 mL) was added and the solution was stirred at 70° C. for 20 hours under an atmosphere of nitrogen. The reaction mixture was added dropwise to a rapidly stirred mixture of aqueous sodium hydroxide (95 g in 150 mL water) and ice (3 L). Sufficient methanesulfonic acid was added to bring the final pH from 4.7 to 1.5. The resulting solid was collected by centrifugation and washed by suspending, spinning down, and decanting from water (5×1.2 L). The final suspension was collected by filtration, air-dried, then oven-dried at 110° C. for 6 hours to afford a brick-red solid (30.6 g, 44%).

A second precipitation from alkaline solution, followed by centrifugation and water washes afforded an analytical sample. Anal: Calc. [C(16)H(12)O(5)] C 70.57, H 5.92. Found: C 70.39, H 6.00, 0.21% water (K-F). NMR (DMSO-d$_6$) (mostly spirolactone form): δ2.172 (s, 12H), 2.508 (m, 2H), 3.342 (m, 2H), and 7.604 (s, 2H). Vis. abs. (pH 8.2; 50 mM aq Tris/HCl): 509 nm (71,300).

D. Preparation of 9-(2-Carboxyethyl)-3,6-diacetoxy-9-ethoxy-2,4,5,7-tetramethyl-9H-xanthene (Ac2EtSF-526)

SF-526 (25.2 g, 74 mmol) was added to ice-cold acetic anhydride (450 mL) followed by pyridine (100 mL) and the mixture was stirred with ice-cooling for 150 minutes. The reaction mixture was filtered then added in a slow, steady stream to rapidly stirred, ice-cold water (7 L). After stirring for an additional 30 minutes, the intermediate product was filtered, washed with water, resuspended in water (4 L) and stirred for another 30 minutes. The solid was collected by filtration and air-dried to afford the spirolactone intermediate (28.9 g). A portion of this intermediate (18.6 g) was dissolved in absolute ethanol (1 L), and refluxed for 90 minutes. The solution was concentrated on a rotary evaporator to 300 mL which resulted in crystallization. The product was collected by filtration, rinsed with ethanol, air-dried, then vacuum-dried to afford colorless microcrystals (11.6 g, 52% based on amount of intermediate used).

Recrystallization from methylene chloride/cyclohexane with charcoal treatment gave colorless microcrystals. M.p.: 154°–155° C. Two evaporations from methylene chloride removed traces of cyclohexane for analysis. Anal: Calc. [C(20)H(20)O(5)] C 70.57, H 5.92. Found: C 70.39, H 6.00, 0.21% water (K-F). NMR (DMSO-d$_6$) (mostly spirolactone form): δ2.172 (s, 12H), 2.508 (m, 2H), 3.342 (m, 2H), and 7.604 (s, 2H). Vis. abs. (pH 8.2; 50 mM aq Tris/HCl): 509 nm (71,300).

E. Preparation of 9-(2-(N-Succinimidyloxycarbonyl)-ethyl)-3,6-diacetoxy-9-ethoxy-2,4,5,7-tetramethyl-9H-xanthene (Ac2EtSF-526-NHS)

Ac2ETSF-526 (4.70 g, 9.99 mmol) was mixed with methylene chloride (75 mL) and 1-(3-dimethylaminopropyl)-3-ethylcarbodiimide hydrochloride (3.10 g, 16.2 mmol) and N-hydroxysuccinimide (1.50 g, 13.0 mmol) were added. The mixture was stirred for 90 minutes and then washed with water (4×50 mL). The combined aqueous layers were back extracted with methylene chloride (50 mL) and the pooled organic layers were dried over sodium sulfate and stripped down. Trituration with ethanol (75 mL) followed by filtration and air-drying afforded the crude product as a light yellow solid (c. 4.7 g). This material was dissolved in methylene chloride (50 mL) and cyclohexane (50 mL) was added. One teaspoon of charcoal was added, the mixture was filtered, and the product was brought down with an additional portion of cyclohexane (25 mL). Collection by filtration, air-drying, and vacuum-drying afforded colorless crystals (3.14 g, 55%).

A second precipitation from methylene chloride with cyclohexane afforded an analytical sample. Anal: Calc. [C(30)H(33)N(1)O(10)]; C 63.48, H 5.86, N 2.47. Found: C 63.08, H 6.00, N 2.37. NMR (DMSO-d$_6$): δ1.058 (t, J=6.9 hz, 3H), 2.136 (s, 6H), 2.155 (s, 6H), 2.228 (m, 4H), 2.371 (s, 6H), 2.748 (s, 4H), 2.918 (q, J=6.9 hz, 2H), and 7.300 (s, 2H).

F. Preparation of 9-(2-(N-methyl-N-(benzyloxycarbonylmethyl)carboxamido)ethyl)-3,6-diacetoxy-9-ethoxy-9H-xanthene (Ac2EtSF-505-Bar-OBn)

To a solution of sarcosine benzyl ester (0.72 g, 4.02 mmol) in methylene chloride (40 mL) was added Ac2EtSF-526-NHS (1.82 g, 3.21 mmol) and 5% aq sodium bicarbonate solution (30 mL). The two-phase mixture was stirred rapidly for 20 hours. The layers were separated and the organic layer washed with 4×15 mL water, dried over sodium sulfate, and concentrated to 15 mL. The solution was diluted to 100 mL with cyclohexane, charcoal-treated, and reduced to 50 mL under a stream of nitrogen resulting in the precipitation of the product. Filtration followed by air-drying afforded a colorless solid (0.96 g, 47%).

Coevaporation with methylene chloride followed by extensive vacuum drying afforded an analytical sample. Anal: Calc. for [C(36)H(41)N(1)O(9)] C 68.45, H 6.54, N 2.22. Found: C 68.29, H 6.70, N 2.07. NMR (DMSO-d$_6$) (Shows 5:2 mixture of amide bond rotamers.): δ(major and minor) 1.049 and 1.027 (t, J=6.8 hz, 3H), 1.783 and 1.700 (m, 2H), 2.129 and 2.099 (s, 6H), 2.159 and 2.129 (s, 6H), 2.14 (m, 2H), 2.379 and 2.371 (s, 6H), 2.699 and 2.690 (s, 3H), 2.873 (q, J=6.8 hz, 2H), 3.958 and 3.976 (s, 2H), 5.075 and 5.019 (s, 2H), 7.266 and 7.233 (s, 2H), and 7.25–7.40 (m, 5H).

G. Preparation of 9-(2-(N-Methyl-N-(N'-succinimidyl-oxycarbonylmethyl)carboxamido)ethyl)-3,6-diacetoxy-9-ethoxy-2,4,5,7-tetramethyl-9H-xanthene (Ac2EtSF-526-Sar-NHS)

To a solution of Ac2EtSF-526-Sar-OBn (0.96 g, 1.52 mmol) in absolute ethanol (40 mL) was added 10% palladium on carbon (0.10 g). The mixture was stirred under balloon pressure of hydrogen for 30 minutes. The catalyst was removed by filtration and the ethanol stripped off to afford a syrupy residue.

This residue was dissolved in methylene chloride (40 mL) and N-hydroxysuccinimide (0.26 g, 2.26 mmol) and 1-(3- dimethylaminopropyl)-3-ethylcarbodiimide hydrochloride (0.59 g, 3.08 mmol) were added. The mixture was stirred for 30 minutes and then washed with water (4×15 mL). The solution was dried over sodium sulfate, concentrated to 15 mL, diluted to 100 mL with cyclohexane, charcoal treated, and reduced in volume to 50 mL under a stream of nitrogen. The product was collected by filtration, air dried, and vacuum dried to afford colorless microcrystals (0.573 g, 59%).

Coevaporation with methylene chloride followed by extensive vacuum drying at 40° C. removed traces of cyclohexane and afforded an analytical sample as an amorphous solid. NMR (DMSO-$d_6$): δ1.043 (t, J=6.7 hz, 3H), 1.82 (m, 2H), 2.130 (s, 6H), 2.157 (s, 6H), 2.15 (m, 2H), 2.378 (s, 6H), 2.748 (s, 4H), 2.778 (s, 3H), 2.891 (q, J=6.7 hz, 2H), 4.327 (s, 2H), and 7.275 (s, 2H).

EXAMPLE 5

PREPARATION OF 5-(3-AMINO-1-PROPYNYL)-2',3'-DIDEOXYCYTIDINE 5'-TRIPHOSPHATE (5-AP3-ddCTP)

A. PREPARATION OF N-PROPARGYLTRIFLUORO-ACETAMIDE (18)

Propargylamine (24.79 g, 0.450 mole; Aldrich, 99%) was added dropwise over 1 hour to methyl trifluoroacetate (69.19 g, 0.540 mole, 1.2 eq, Aldrich) at 0°. After stirring an additional hour at 0°, distillation through a 15 cm Vigreaux column afforded 62.12 g (91%) of trifluoroacetamide 18 as a colorless liquid (bp 68.5°–69.5° at 11 torr). This material was homogeneous by NMR and GC and was used interchangeably with spectroscopically-identical material prepared by acylating propargylamine with trifluoroacetic acid anhydride.

$^1$H-NMR (CDCl$_3$): 6.85 (broad s, 1H, NHTFA), 4.17 (dd, J=5.6 and 2.5, 2H, CH$_2$), 2.35 (t, J=2.5, 1H, CH). IR (neat: cm$^{-1}$): 3300 (N—H), 3095 and 2935 (C—H), 2130 (acetylene), 1720 (C=O), 1550 (N—H), 1430, 1365, 1160, 1040, 998, 918, 857,829, 772, and 725.

B. PREPARATION OF 5-IODO-2',3'-DIDEOXYCYTIDINE (19)

A solution of 2',3'-dideoxycytidine (2.11 g, 10 mmol, Raylo) and mercuric acetate (3.35 g, 10.5 mmol, Fisher) in 50 mL of methanol was refluxed for 19 hours. The resulting white suspension was diluted with methanol (50 mL) and dichloromethane (100 mL). Iodine (3.05 g, 12 mmol) was added and the suspension was stirred at 25°. After 4 hours, the free base form of AG3X4A resin (20 mL, 38 meq, Bio-Rad) was added and hydrogen sulfide was bubbled into the reaction for 15 minutes. Complete precipitation of mercury(II) was verified by TLC. The reaction was filtered through filter aid and the filter aid was washed with 1:1 methanol-dichloromethane. The filtrate was evaporated onto silica gel (10 g) and the loaded silica gel was placed on top of a 150 g silica gel column. Elution with 5%, 10% and 20% methanol in dichloromethane afforded 2.79 g (83%) of iodide 19 as a colorless crystalline solid. Two recrystallizations from boiling water afforded, after vacuum-drying at 50°, large, analytically-pure prisms (mp: d 178°).

$^1$H-NMR (DMSO-$d_6$): 8.50 (s, 1H, H6), 7.73 (broad s, 1H, —NH$_2$a), 6.53 (broad s, 1H, —NH$_2$b), 5.86 (dd, J=6.5 and 2.1, 1H, H1'), 5.19 (t, 1H, 5'0H), 4.04 (m, 1H, H4'), 3.75 (ddd, J=12.1, 5.2, and 2.9, 1H, H5'a), 3.53 (dt, J=12.1 and 3.8, 1H, H5'b), and 2.3–1.7 (m, 4H, H2' and H3'). Calculated for C$_9$H$_{12}$N$_3$O$_3$I: C 32.07%, H 3.59%, N 12.46%. Found: C 32.05%, H 3.80%, N 12.46%.

C. PREPARATION OF 5-(3-TRIFLUOROACETAMIDO-1-PROPYNYL)-2',3'-DIDEOXYCYTIDINE (20): A GENERAL PROCEDURE FOR COUPLING AMINOALKYNES TO IODONUCLEOSIDES

A 50-mL, three-necked flask was charged with iodocytidine 19 (770 mg, 2.00 mmol) and cuprous iodide (76.2 mg, 0.400 mmol, 0.20 eq: Aldrich, Gold Label). After flushing the flask with argon, dry dimethylformamide (10 mn, Aldrich) was added to produce a 0.2M solution of iodocytidine which contained suspended cuprous iodide. N-Propargyltrifluoroacetamide (0.70 mL, 6.00 mmol, 3.0 eq) and triethylamine (0.56 mL, 4.00 mmol, 2.0 eq. stored over molecular sieves) were added via syringe. Tetrakis(triphenylphosphine)palladium(O) (231 mg, 0.20 mmol, 0.10 eq) was weighed into a vial in a dry box and added to the reaction mixture. The cuprous iodide dissolved, affording a yellow solution which gradually darkened over several hours. The reaction was allowed to proceed until TLC indicated that the starting material was completely consumed. After 4 hours, the reaction was diluted with 20 mL of 1:1 methanol-dichloromethane and the bicarbonate form of a strongly basic anion exchange resin (Bio-Rad AGl X8, 2.0 g, ca. 6 eq) was added. After stirring for about 15 minutes, evolution of gas ceased. After 30 minutes, the reaction mixture was filtered and the resin was washed with 1:1 dichloromethane-methanol. The combined filtrates were rapidly concentrated with a rotary evaporator. (Removal of dimethylformamide required about 10 minutes at 45° and 2 torr.) The residue was immediately purified by chromatography on 150 g of silica gel using 10%, 15% and 20% methanol in dichloromethane. Removal of solvent from the appropriate fractions afforded 651 mg (90%) of alkynylamine 20 as a pale yellow crystalline foam which was homogeneous by TLC and NMR. The product from a similar preparation was established to be a hemi-hydrate by elemental analysis.

$^1$H-NMR (DMSO-$d_6$): 9.96 (broad s, 1H, NHTFA), 8.32 (s, 1H, H6), 7.76 (broad s, 1H, NH$_2$a), 6.78 (broad s, 1H, NH$_2$b), 5.88 (dd, J=6.5 and 2.5, 1H, H1'), 5.13 (t, J=5.1, 1H, 5'0H), 4.28 (d, J=5.0, 2H, —CH$_2$—), 4.04 (m, 1H, H4'), 3.73 (ddd, J=12.0, 5.0 and 3.1, 1H, H5'a), 3.53 (dr, J=12.1 and 4.0, 1H, H5'b), 2.3–1.7 (m, 4H, H2' and H3'). $^{19}$F-NMR (DMSO-$d_6$): −74.0 (s). UV (MeOH): maxima at 238.5 (17,100) and 295.5 (9,300). Calculated for C$_{14}$H$_{15}$N$_4$O$_4$F$_3$.1/2H$_2$O: C 45.53, H 4.37, N 15.17. Found: C 45.56, H 4.52, N 15.26.

D. PREPARATION OF TRIS(TRI-N-BUTYLAMMONIUM) PYROPHOSPHATE

Tetrasodium pyrophosphate decahydrate (4.46 g, 10 mmol) was dissolved in the minimum amount of water (about 50 mL) and passed through a column of AG50W X8 resin (100–200 mesh, 4×10 cm bed) poured in water. The column was eluted with water and the eluent was collected in an ice-cooled flask until pH of the eluent approached neutrality. Tri-n-butylamine (Aldrich Gold Label, 7.1 mL, 30 mmol) was added to the eluent and the two phases were stirred vigorously until all of the amine dissolved. The resulting solution was lyophilized. The residue was coevaporated twice with dry pyridine and once with dry dimethylformamide. The residue was dissolved in dry dimethylforamide (10 mL) and the resulting 1.0M solution was stored (for as long as one month) at 0° under argon until used.

E. PREPARATION OF 5-(3-AMINO-1-PROPYNYL)-2',3'-DIDEOXYCYTIDINE 5'-TRIPHOSPHATE (5-AP3-ddCTP). A GENERAL PROCEDURE FOR CONVERTING PROTECTED ALKYNYLAMINO NUCLEOSIDES TO THE CORRESPONDING 5'-TRIPHOSPHATES AND REMOVING THE TRIFLUOROACETYL PROTECTING GROUP

Alkynylamino nucleoside 20 (361 mg, 1.00 mmol) was dissolved in trimethyl phosphate (2.0 mL, Aldrich Gold Label) while stirring under argon in an oven-dried flask. The solution was cooled to −10° and phosphorus oxychloride (0.093 mL, 1.00 mmol, Aldrich Gold Label) was added by syringe. After stirring the reaction mixture at −10° for 30 minutes, a second aliquot of phosphorus oxychloride (0.093 mL, 1.00 mmol) was added and the solution was allowed to warm slowly to 25° while stirring. Aliquots from the reaction mixture were quenched with 1N aqueous hydroxide and analyzed by HPLC. When conversion to the corresponding nucleotide monophosphate was at a maximum (in this case 100 minutes after the second addition of phosphorus oxychloride), the reaction mixture was added dropwise to a precooled (−10°) solution of tris(tri-n-butylammonium) pyrophosphate (6.0 mL of the above 1.0M solution in dry dimethylformamide). The solution was allowed to warm slowly to 25° while stirring under argon. After 100 minutes, the reaction solution was added slowly to a precooled (0°) solution of triethylamine (1.4 mL) in water (20 mL). The solution was stirred with ice-cooling for 15 minutes and then allowed to stand overnight at about 2°.

The volatiles were removed by vacuum evaporation at 25° and 0.5 torr. The residue was redissolved in water (75 mL) and applied to a column of DEAE-Sephadex A-25-120 (2.6×65 cm bed) that had been equilibrated with: 1) pH 7.6, 1.0M aqueous TEAB (300 mL), 2) 1.0M aqueous potassium bicarbonate (300 mL), and 3) pH 7.6, 0.1M aqueous TEAB (300 mL). The column was eluted with a linear gradient of pH 7.6 aqueous TEAB from 0.1M (1 L) to 1.0M (1 L). The column was driven at 100 mL/h while collecting fractions every 12 minutes. The elution was monitored by absorbance at 270 nm (40 AUFS). The desired material eluted as a well-separated, major band near the end of the gradient (Fractions 73–80). The product-containing fractions were pooled, concentrated (at below 30°), and co-evaporated twice with absolute ethanol. The residue was taken up in water (20.4 mL) and lyophilized.

The intermediate product was taken up in water (12.5 mL) and concentrated ammonium hydroxide (12.5 mL) was added. After stirring for 3.5 hours, the solution was stirred under aspirator vacuum for 2 hours to remove the excess ammonia gas and then lyophilized. The residue was taken up in pH 7.6 0.1M aqueous TEAB (10 mL) and applied to a column of DEAE-Sephadex A-25-120 (1.6×55 cm bed) that had been prepared as described above. The column was eluted while collecting 6 mL fractions with a linear gradient of TEAB from 0.1M (280 mL) to 1.0M (280 mL). The product eluted as a single major peak. The fractions estimated to contain pure product (#39–45) were pooled, concentrated (at below 30°), co-evaporated with absolute ethanol (2×), and taken up in water (9.8 mL). The solution was assayed by UV absorption and HPLC and then lyophilized.

A dilute solution of the product showed absorption maxima at 240 and 293.5 nm in pH 8.2 50 mM aqueous Tris buffer. Assuming an absorption coefficient for the product equal to that of the starting material (9,300), the yield of 5-AP3-ddCTP, based on the absorption at 293.5 nm, was 0.32 mmol (32%). HPLC (Zorbax SAX, 0.2M pH 6.5 aqueous potassium phosphate, monitoring 270 nm) of the final product showed essentially a single peak (>99%).

$^{1}$H-NMR (D$_2$O): 8 57 (s 1H H6), 6.03 (dd, J=6.4 and 1.6, 1H, H1'), 4.42 (m, 2H, H4' and H5'a), 4.18 (ddd, J=12, 5.5 and 3, 1H, H5'b), 4.036 (s, 2H, —CH$_2$—), 2.5–1.9 (m, 4H, H2' and H3'), plus counterion (triethylammonium) peaks. $^{31}$P-NMR (D$_2$O): −9.02 (d, J=20, IP), −9.74 (d, J=20, 1P), −21.37 (t, J=20, IP). UV (pH 8.2 aq Tris): maxima at 240 and 293.5 nm.

EXAMPLE 6

PREPARATION OF 5-(3-AMINO-1-PROPYNYL)-2',3'-DIDEOXYURIDINE 5'-TRIPHOSPHATE (5-AP3-ddUTP)

A. PREPARATION OF 5-IODO-2',3'-DIDEOXYURIDINE (21)

Dideoxyuridine (2.122 g, 10.0 mmol) was dissolved in 30 mL of warm methanol and, after cooling to 25°, iodine monochloride (4.06 g, 25 mmol, 2.5 eq, Fisher) in methanol (20 mL) was added over 5 minutes. The dark purple reaction mixture was heated in a 50° bath under nitrogen for 20 minutes and then immediately cooled in an ice-water bath. After standing without stirring for 165 minutes, the resulting precipitate was collected by filtration and washed with cold methanol (2×10 mL). Vacuum-drying overnight afforded 2.232 g (66%) of iodide 21 as off-white microcrystals. This material was used without further purification in the next reaction, but other preparations were purified by chromatography or recrystallization from boiling methanol (30 mL/g) to give white needles (mp d 160°–164°). NMR indicated that the crude precipitate was homogeneous, but also that the 5'-hydroxyl proton was very broad due to exchange catalyzed by trace impurities. Chromatographed or recrystallized materials afforded spectra in which this proton was, as usual, a sharp triplet.

$^{1}$H-NMR (DMSO-d$_6$): 11.60 (broad s, 1H, H3), 8.57 (s, 1H, H6), 5.90 (dd, J=2.0 and, 6.6, 1H, H1'), 5.2 (broad s, 1H, 5'OH), 4.06 (m, 1H, H4'), 3.75, and 3.53 (m, 1H, H5'), 2.26, 2.02 and 1.84 (m, 4H, H2' and H3').

B. PREPARATION OF 5-(3-TRIFLUOROACETAMIDO-1-PROPYNYL)-2',3'-DIDEOXYURIDINE (22)

Iodouridine 21 was coupled for 3 hours to N-propargyl-trifluoroacetamide following the general method given in Example 5C. Chromatography with a 0–5% methanol in dichloromethane gradient afforded material which was homogeneous by TLC, but which was difficult to dry. After co-evaporating the chromatographed product several times with chloroform and vacuum-drying, 536.5 mg of alkynylamino nucleoside 22 was obtained as a white foam. This material was homogeneous by TLC and was pure by NMR except for a small amount (39 mole %; corrected yield 66%) of chloroform.

$^{1}$H-NMR (DMSO-d$_6$): 11.61 (s, 1H, H3), 10.07 (distorted t, 1H, NHTFA), 8.35 (s, 1H, H6), 7.26 (s, 0.39H, CHCl$_3$), 5.89 (dd, J=6.6 and 3.2, 1H, H1'), 5.15 (t, J=5.2, 1H, 5'OH), 4.22 (broad d, 2H, —CH$_2$N—), 4.04 (apparent hept, J=3.5, 1H, H4'), 3.73, and 3.53 (m, 1H, H5'), 2.26, 2.03 and 1.84 (m, 4H, H2' and H3'). TLC (95:5 dichloromethane-methanol, two elutions, UV): Starting iodide 21, R$_f$=0.37; product 22, 0.28; catalysts, 0.95 and 0.80 plus slight streakiness.

C. PREPARATION OF 5-(3-AMINO-1-PROPYNYL)-2',3'-DIDEOXYURIDINE 5'-TRIPHOSPHATE (5-AP3-ddUTP, 23)

Alkynylamino nucleoside 22 (0.30 mmol) was converted to the corresponding triphosphate and its trifluoroacetyl group was removed following the general procedure given in Example 5E. After addition of the second aliquot of phosphorus oxychloride, phosphorylation was allowed to proceed for 210 minutes. Assuming an absorption coefficient for the product equal to that of the starting material (13,000), the yield of triphosphate 23, based on its UV absorption at 291.5 nm, was 18%.

EXAMPLE 7

PREPARATION OF 7-(3-AMINO-1-PROPYNYL)-2',3'-DIDEOXYGUANOSINE 5'-TRIPHOSPHATE (7-AP3-ddc7GTP)

A. PREPARATION OF 6-METHOXY-2-METHYLTHIO-9-(3,5-DI-O-p-TOLUOYL-2-DEOXY-β-D-RIBOFURANOSYL)-7-DEAZAPURINE (24)

6-Methoxy-2-methylthio-7-deazapurine (9.2 g, prepared following the procedure of F. Seela and R. Richter, Chem. Ber., 111, 2925 (1978)) was azeotropically dried by dissolving in 150 mL of dry pyridine and evaporating to dryness at 30°–35°. This material was suspended in 450 mL of dry acetonitrile at room temperature under nitrogen and sodium hydride (2.16 g of a 60% suspension in oil) was added with stirring. After 45 minutes, 1-chloro-2-deoxy-3,5-di-O-p-toluoyl-α-D-ribofuranose (18.6 g, prepared following the procedure of M. Hoffer, Chem. Ber., 93, 2777 (1960)) was added in three equal portions over a 20 minutes. After stirring the reaction mixture for an additional 45 minutes at room temperature, acetic acid (1 mL) and dichloromethane (300 mL) were added. The mixture was suction filtered through a pad of filter-aid, and the filtrate was evaporated to dryness. The residue was dissolved in benzene and this solution was washed with water (2×) and brine (1×). After drying the organic layer over sodium sulfate and evaporating, the residue was dissolved in methanol (400 mL) and allowed to crystallize affording 19.24 g (73.8%) of ribosylated product 24 as colorless crystals (mp 106°–107°).

$^1$H-NMR (CDCl$_3$, 360 MHz): 2.42 (s, 3H, toluoyl CH$_3$), 2.44 (s, 3H, toluoyl CH$_3$), 2.64 (s, 3H, SCH$_3$), 2.70 and 2.89 (m, 2H, H2'), 4.08 (s, 3H, OCH$_3$), 4.56, (m, 1H, H3'), 4.65 (m, 2H, H5'), 5.74 (m, 1H, H4'), 6.44 (d, J=4, 1H, H7), 6.77 (dd, J=8 and 6, 1H, H1'), 7.05 (d, J=4, 1H, H8) and 7.25 and 7.95 (m, 8H, toluoyl H). Recrystallization of a sample of the above material from methanol containing a small amount of dichloromethane afforded crystals of mp 109°–110°.

B. PREPARATION OF 6-METHOXY-2-METHYLTHIO-9-(2-DEOXY-β-D-RIBOFURANOSYL)-7-DEAZAPURINE (25)

A suspension of ester 24 (19 g) and the hydroxide form of a strongly basic anion exchange resin (38 g of Rexyn 201) in 600 mL of methanol was refluxed for 1.5 hour under nitrogen. The hot suspension was suction filtered to remove the resin and the filtrate was evaporated to dryness. The solid residue was dissolved in ether (450 mL) and, after 10 minutes, the solution was filtered through a pad of filter aid to remove a small amount of a colored impurity. The solution was seeded with crystals of the desired product obtained from a previous reaction and allowed to stand overnight at 25°. Crystalline diol 25 was collected by filtration and the mother liquor was concentrated to afford a second crop. Each crop was washed thoroughly with ether and dried to afford a total of 8.43 g (78.0%) of diol 2.5 as colorless crystals (mp 129°–130°).

$^1$H-NMR (DMSO-d$_6$, 360 MHz): 2.21 and 2.55 (m, 2H, H2'), 2, 56 (s, 3H, SCH$_3$), 3.53 (m, 2H, H5'), 3.82 (m, 1H, H3'), 4.02 (s, 3H, OCH$_3$), 4.36 (m, 1H, H4'), 4.90 (t, J=5.5, 1H, 5'OH), 5.30 (d, J=5.5, 1H, 3'OH), 6.48 (d, J=4, 1H, H7), 6.55 (dd, J=8 and 6, 1H, H1'), 7.48 (d, J=4, 1H, H8). Recrystallization of a sample of this material from dichloromethane containing a small amount of methanol afforded crystals of mp 130°–131°.

C. PREPARATION OF 6-METHOXY-2-METHYLTHIO-9-(5-0-TRIPHENYLMETHYL-2-DEOXY-β-D-RIBOFURANOSYL)-7-DEAZAPURINE (26)

Diol 25 (7.2 g) was azeotropically dried by dissolving in dry pyridine and evaporating the solution to dryness at 35°. The residue was dissolved in dry pyridine (100 mL) and triphenylmethyl chloride (8.0 g), triethylamine (4.0 mL), and 4-(dimethylamino)pyridine (300 mg) were added. After heating the reaction mixture at 65° under nitrogen for 30 minutes, a second addition of triphenylmethyl chloride (1.0 g) was made and heating was continued for 16.5 hours. After cooling, the reaction mixture was concentrated and the residue was partitioned between dichloromethane and water. The aqueous layer was extracted with dichloromethane and the combined organic layers were washed with 0.3N hydrochloric acid, aqueous sodium bicarbonate, and brine. After drying over sodium sulfate and concentrating, purification of the crude product by chromatography on silica gel with 0%, 1%, 1.5% and 2% methanol in dichloromethane afforded 12.1 g (94.5%) of monotrityl ether 26 as a colorless glass.

$^1$H-NMR (CDCl$_3$, 300 MHz): 2.58 (s, 3H, SCH$_3$), 2.42 and, 2.62 (m, 2H, H2'), 3.37 (m, 2H, H5'), 4.04 (m, 1H, H3'), 4.08 (s, 3H, OCH$_3$), 4.60 (m, 1H, H4'), 6.40 (d, J=4, 1H, H7), 6.68 (apparent t, J=7, 1H, H1'), 7.00 (d, J=4, 1H, H8), 7.27 and 7.43 (m, 15H, trityl H). This data was obtained from a different batch of 26 prepared as described above.

D. PREPARATION OF 6-METHOXY-2-METHYLTHIO-9-(5-0-TRIPHENYLMETHYL-2,3-DIDEOXY-β-D-RIBOFURANOBYL)-7-DEAZAPURINE (27)

A solution of trityl ether 26 (12.1 g), 4-dimethylaminopyridine (9.2 g), and phenyl chlorothionocarbonate (7.5 mL, Aldrich) dry dichloromethane (220 mL) was stirred at 25° for 2 hours under nitrogen. Since TLC analysis indicated that the reaction was incomplete, phenyl chlorothionocarbonate (4.0 mL) was added and the reaction mixture was stirred for an additional 1 hour. The solution was diluted with dichloromethane (280 mL) and washed sequentially with 0.5N hydrochloric acid (500 mL), 0.5N sodium hydroxide (500 mL), and brine. The organic layer was dried over sodium sulfate and evaporated to dryness.

The resulting crude thionocarbonate was dissolved in dry toluene (350 mL) and azoisobisbutyronitrile (350 mg) and tri-n-butyltin hydride (10 mL) were added. The resulting solution was heated at 100°–105° for 10 minutes. After cooling, the solution was diluted with a little ether and was shaken with 10% aqueous potassium fluoride (350 mL). The two layers were filtered through a pad of filter aid (to remove a dark sludge) and separated. The organic layer was washed with 0.75N potassium hydroxide and brine, dried over sodium sulfate and concentrated. Chromatography of the resulting oil on silica gel with 1:1 dichloromethane-ether and then with dichloromethane afforded 9.93 g (84.5%) of dideoxynucleoside 27 as a colorless solid (mp 122°–124°).

$^1$H-NMR (CDCl$_3$, 360 MHz): 2.10, 2.33, and 2,43 (m, 4H, H2' and H3'), 2.60 (s, 3H, SCH$_3$), 3.30 (m, 2H, H5'), 4.08 (s, 3H, OCH$_3$), 4.29 (m, 1H, H4'), 6.36 (d, J=3.7, 1H, H7), 6.53 (dd, J=7 and 4, 1H, H1'), 7.09 (d, J=3.7, 1H, H8), 7.25 and 7.45 (m, 15H, trityl H).

E. PREPARATION OF 7-IODO-6-METHOXY-2-METHYLTHIO-9-(5-0-TRIPHENYLMETHYL-2,3-DIDEOXY-β-D-RIBOFURANOSYL)-7-DEAZAPURINE (28)

N-Iodosuccinimide (10.0 g) was added to a solution of deazapurine 27 (9.9 g) in dry dimethylformamide (550 mL).

After stirring in the dark under nitrogen for 16 hours, 10% aqueous sodium bicarbonate (2.5 mL) was added and the reaction mixture was concentrated in vacuo at 50° to a volume of 100 mL. This solution was partitioned between water and ethyl acetate. The organic layer was washed with 5% aqueous sodium hydrosulfite and brine, dried over sodium sulfate, and concentrated. Chromatography of the slightly impure product on silica gel with dichloromethane afforded 11.68 g (95.6%) of iodide 28 as a colorless glassy solid.

$^1$H-NMR (CDCl$_3$, 300 MHz): 2.06, 2.24, and 2.41 (m, 4H, H2' and H3'), 2.58 (s, 3H, SCH$_3$), 3.30 (m, 2H, H5'), 4.10 (s, 3H, OCH$_3$), 4.29 (m, 1H, H4'), 6.47 (dd, J=6 and 4, 1H, H1'), 7.19 (s, 1H, H8), 7.30 and 7.46 (m, 15H, trityl H). This data was obtained from a different batch of 28 prepared as described above.

F. PREPARATION OF 7-IODO-2-METHYLTHIO-9-(5-0-TRIPHENYLMETHYL-2,3-DIDEOXY-β-D-RIBOFURA-NOSYL)-7-DEAZAPURI-4-ONE (29)

Sodium thiocresolate was prepared by adding sodium methoxide (1 eq) to a solution of thiocresol in methanol and then evaporating to dryness. A mixture of methyl ether 28 (4.0 g), sodium thiocresolate (4.0 g), and hexamethylphosphoramide (10 mL) in dry toluene (150 mL) was refluxed under nitrogen for 4.5 hours. After cooling, the mixture was partitioned between ethyl acetate and water. The organic layer was washed with water and brine, dried over sodium sulfate, and evaporated to dryness. Chromatography of the resulting crude product on silica gel with 0% and 2% methanol in dichloromethane afforded 3.80 g (97.0%) of deazapurinone 29 as a colorless glassy solid.

$^1$H-NMR (CDCl$_3$, 360 MHz): 2.05, 2.25, and 2.42 (m, 4H, H2' and H3'), 2.60 (s, 3H, SCH$_3$), 3.30 (m, 2H, H5'), 4.28 (m, 1H, H4'), 6.40 (dd, J=7 and 4, 1H, H1'), 7.05 (s, 1H, H8), 7.30 and 7.46 (m, 15H, trityl H), 10.00 (broad s, 1H, H1).

G. PREPARATION OF 7-IODO-5'-0-TRIPHENYLM-ETHYL-2',3'-DIDEOXY-7-DEAZAGUANOSINE (30)

Meta-chloroperoxybenzoic acid (1.23 g, 85%, Aldrich) was added to a stirred solution of methylthio ether 2.9 (3.6 g) in dry dichloromethane (150 mL) at 0° under nitrogen. After 15 minutes, the cooling bath was removed and stirring was continued at 25° for 40 minutes. This solution was washed with aqueous sodium bicarbonate and brine and dried over sodium sulfate. Methanol (two percent by volume) was added and the resulting solution was passed through a short plug of silica gel to remove polar impurities. The resulting crude sulfoxide (3.07 g) was dissolved in dioxane (40 mL) and placed in a glass-lined bomb. Ammonia (10.0 g) was added and the mixture was heated at 100° for 2 hours in an autoclave. The resulting solution was evaporated to dryness. The residue was dissolved in dichloromethane (20 mL) and filtered through a pad of filter-aid. Methanol (40 mL) was added to the solution and, on cooling, 1.57 g of colorless product crystallized. The mother liquor was evaporated and purified by medium pressure liquid chromatography on silica gel with 5% methanol in dichloromethane to afford an additional 328 mg of product as colorless crystals. The total yield of deazaguanosine 30 was 1.90 g (55.4%).

$^1$H-NMR, (CDCl$_3$, 300 MHz): 2.05, 2.23, and 2.35 (m, 4H, H2' and H3'), 3.29 (m, 2H, H5'). 4.26 (m, 1H, H4'), 5.90, (broad s, 1H, NH$_2$), 6.24 (dd, J=7 and 4, 1H, H1'), 6.90 (s, 1H, H8), 7.30 and 7.46 (m, 15H, trityl H) 10.90 (broad s, 1H, H1). Recrystallization of a sample of this material from methanol-dichloromethane afforded crystals of mp 201°–203°.

H. PREPARATION OF 2',3'-DIDEOXY-7-IODO-7-DEAZAGUANOSINE (31)

A solution of trityl ether 30 (1.7 g) in formic acid (12 mL) was stirred at room temperature for 10 minutes. The resulting yellow suspension was then quickly evaporated to dryness in vacuo at 30°. Chromatography of the residue on silica gel with 5%, 7%, and 10% methanol in dichloromethane afforded 940 mg of a colorless solid. Trituration of this solid with ether containing a little dichloromethane yielded 838 mg (81.0%) of nucleoside 31 as colorless crystals.

$^1$H-NMR (DMSO-d$_6$, 360 MHz): 1.95, 2.09, and 2.26 (m, 4H, H2', and H3'), 3.48 and 3.54 (m, 2H, H5'), 3.98 (m, 1H, H4'), 4.90 (broad t, J=5, 1H, 5'OH), 6.08 (m, 1H, H1'), 6.32 (broad s, 2H, NH$_2$). 7.12 (s, 1H, H8), 10.46 (broad s, 1H, H1).

I. PREPARATION OF 7-(3-TRIFLUOROACETAMIDO-1-PROPYNYL)-2',3+-DIDEOXY-7-DEAZAGUANOSINE (32)

Iodide 31 (376 mg, 1.00 mmol) was coupled for 2.25 hours to N-propargyltrifluoroacetamide by the general method given in Example 5C. Product and starting material were indistiguishable by TLC, so the reaction was monitored by reverse phase HPLC (10 cm ODS, 1 mL/minute, gradient from 100% water to 100% methanol over 5 minutes, then 100% methanol, with UV detection at 280 nm: starting iodide 31, 5.49 minutes; product 32, 5.75 minutes: intermediate, 6.58 minutes). The crude product was poorly soluble in dichloromethane, so it was concentrated from a dichloromethane-methanol solution onto 5 g of silica gel before being loaded onto the chromatography column. Elution with 2%, 5%, 7% and 10% methanol in dichloromethane afforded 300 mg (78%) of alkynylamino nucleoside 32 as a yellow solid.

$^1$H-NMR (DMSO-d$_6$, 360 MHz): 1.96, 2.08, and 2.28 (m, 4H, H2' and H3'), 3.47 and 3.55 (m, 2H, H5'), 3.99 (m, 1H, H4'), 4.22 (broad s, 2H, —CH$_2$—), 4.90 (t, J=5, 1H, 5'OH), 6.09 (dd, J=6 and 4, 1H, H1'), 6.33 (broad s, 2H, NH$_2$), 7.30 (s, 1H, H8), 10.05 (broad s, 1H, NHTFA), 10.50 (broad s, 1H, H1). $^1$H-Decoupled $^{13}$C-NMR (DMSO-d$_6$): 155.5 (q J=36.5, trifluoroacetyl carbonyl), 157.8, 153.1 and 149.9 (C2, C4 and C6), 122.6 (C8), 115.9 (q, J=288, CF3), 99.4 and 97.5 (C7 and C5), 84.2 and 77.4 (acetylenic), 83.2 and 81.0 (C1' and C4'), 62.9 (C5'), 29.7 (propargylic), 31.8 and 25.8 (C2' and C3'). This $^{13}$C-NMR data was obtained from a different batch of 32 prepared as described above.

J. PREPARATION OF 7-(3-AMINO-1-PROPYNYL)-2',3'-DIDEOXY-7-DEAZAGUANOSINE 5'-TRIPHOSPHATE (7-AP3-ddc7GTP)

Alkynylamino nucleoside 32 (0.90 mmol) was converted to the corresponding 5'-triphosphate and the trifluoroacetyl protecting group was subsequently removed following the general procedure given in Example 5F. After the second addition of phosphorus oxychloride, the reaction was stirred for an additional 165 minutes. Assuming an absorption coefficient for the product equal to that of the starting material (11,900), the yield of 7-AP3-ddc7GTP, based on its absorption at 272.5 nm, was 18%.

EXAMPLE 8

PREPARATION OF 7-(3-AMINO-1-PROPYNYL)-2',3'-DIDEOXY-7-DEAZAADENOSINE 5'-TRIPHOSPHATE (7-AP3-ddc7ATP)

A. PREPARATION OF 2'-ACETOXY-3'-BROMO-5'-(2-ACETOXYISOBUTYRYL)ADENOSINE (33)

2-Acetoxyisobutyryl bromide (19.5 mL, 150 mmol, 5 eq, prepared according to the procedure of Russell et al, J. Am. Chem Soc., 95, 4016–4030 (1973)) was added over 15 minutes to a suspension of tubercidin (7-deazaadenosine, 6.66 g, 25.0 mmol, Sigma) in dry acetonitrile (250 mL, Aldrich). The suspended solid dissolved in about 5 minutes and the reaction was stirred under nitrogen for 22 hours at 25°. The reaction mixture was added to a solution of dipotassium hydrogen phosphate (43.55 g, 300 mmol, 6 eq) in water (400 mL). After stirring for 30 minutes, the reaction mixture was extracted with ethyl acetate (1×400 mL and 2×200 mL). The combined organic layers were dried over magnesium sulfate and evaporated to dryness to afford 14.73 g (118%) of white foam. This material was greater than 95% one slightly broadened spot by TLC (with UV detection), but NMR showed that one major and at least one minor product were present. The NMR spectrum was consistent with the major product being bromoacetate 33.

$^1$H-NMR (DMSO-$d_6$) for the major component 33: 8.08 (s, 1H, H2), 7.34 (d, J=3.7, 1H, H8), 7.12 (broad s, 2H, $NH_2$), 6.70 (d, J=3.7, 1H, H7), 6.32 (d, J=3.8, 1H, H1'), 5.61 (dd, J=2.4 and 3.8, 1H, H2'), 4.89 (dd, J=2.4 and 4.5, 1H, H3'), 4.43 (m, 1H, H4'), 4.35 (dd, J=12 and 4, 1H, H5'a), 4.29 (dd, J=12 and 7, 1H, H5'b), 2.08 (s, 3H, OAc), 2.00 (s, 3H, OAc), and 1.49 (s, 6H, $2CH_3$).

B. PREPARATION OF 2',3'-DIDEOXY-2',3'-DIDEHYDRO-7-DEAZAADENOSINE (34)

Zinc-copper couple was freshly prepared by rapidly (total elapsed time of about 10 minutes) washing zinc dust (20 g, Mallinkrodt) with 1N hydrochloric acid (3×50 mL), water (2×50 mL), 2% cupric sulfate (2×50 mL), water (4×50 mL), ethanol (3×50 mL) and ether (2×50 mL). During each wash, the zinc dust was stirred in a fritted funnel until it was suspended and the wash was removed by suction while minimizing exposure of the zinc to air. The couple was vacuum-dried for 30 minutes. The above crude bromoacetate (14.63 g) was dissolved in dry dimethylformamide (150 mL, Aldrich) and approximately 25 mL of solvent was removed with a rotary evaporator (45°, at 2 torr). Fresh zinc-copper couple (14.63 g, about 9 eq) was added and the resulting suspension was stirred under nitrogen at 25°. Depending on the quality of the zinc-copper couple, this reaction can show an induction period and/or variable rate, so the reaction was allowed to proceed until TLC (90:9:1 dichloromethane-methanol-concentrated ammonium hydroxide: starting material $R_f$=0.45 and products $R_f$=0.39 and 0.36) indicated the starting material had been completely consumed. In this case, the reaction was complete in less than 15 minutes. After 100 minutes, saturated aqueous sodium bicarbonate (75 mL) was added carefully over 10 minutes to the reaction mixture. The reaction mixture was filtered through a filter aid and the filter aid was washed with methanol (2×50 mL). The combined filtrates were evaporated to dryness and the residue was partitioned between water (150 mL) and ethyl acetate (150 mL). The aqueous layer was extracted with ethyl acetate (2×100 mL) and the combined organic extracts were dried over magnesium sulfate, concentrated, and vacuum dried for 1 hour.

The resulting dark orange semisolid was dissolved in methanol (100 mL) and then water (25 mL) and Rexyn 201 resin (29 g, 4.3 meg/g, 5 eq, hydroxide form) were added. The reaction mixture was refluxed for a total of 210 minutes. Monitoring by TLC (85:13:2 dichlormethane-methanol-concentrated ammonium hydroxide: intermediate ester, $R_f$=0.49; final product 34, 0.24) indicated that the reaction had rapidly halted at about 70% conversion, so after 165 minutes, an additional 29 g of resin was added. Without cooling, the resin was removed by filtration and washed with 1:1 dichloromethane-methanol (2×75 mL). The combined filtrates were evaporated to dryness and the resulting purple solid was recrystallized from boiling isopropanol (150 mL) to afford 3.778 g of olefin 34 as a off-white needles (mp 205°–206°). A second crop of 0.631 g (pale purple needles, mp 202°–203°) was obtained by concentrating the mother liquors to 25 mL. Both crops (total 4.409 g, 76%) were homogeneous by TLC and pure by NMR except for a trace of isopropanol.

$^1$H-NMR (DMSO $d_6$): 8.07 (s, 1H, H2), 7.15 (d, J=3.6, 1H, H8), 7.12 (broad s, 1H, H1'), 7.01 (broad s, 2H, $NH_2$), 6.57 (d, J=3.6, 1H, H7), 6.43 and 6.02 (broad d, J=6.0, 1H each, H2' and H3'), 4.95 (t, J=6.5, 1H, 5'OH), 4.79 (m, 1H, H4'), and 3.52 (m, 2H, H5').

C. PREPARATION OF 2',3'-DIDEOXY-7-DEAZAADENOSINE (35)

A 450-mL Parr bottle was charged with olefin 34 (3.80 g), ethanol (76 mL), 10% palladium on carbon (380 mg, Aldrich) and 40 psi of hydrogen. After shaking for 4.67 hours at 25°, 14.5 psi of hydrogen had been absorbed and hydrogen uptake had ceased. TLC (two elutions with 85:13:2 dichloromethanemethanol-concentrated ammonium hydroxide: starting material 34, 0.45; product 35, 0.48) showed complete conversion to a single UV-active new product. The catalyst was removed by filtration through filter aid and washed with ethanol. Removal of solvent from the filtrate and vacuum drying overnight afforded 3.98 g (104%) of dideoxynucleoside 35 as a white foam. NMR indicated that the product was homogeneous except for the presence of 8 wt% of ethanol (96% corrected yield). Similar batches of this material resisted crystallization and became extremely hygroscopic upon azeotropic drying with anhydrous solvents. Therefore this material was stored under vacuum for about 1 week and used when NMR indicated that the material contained 5 wt% of ethanol. The lack of crystallinity and spectral characteristics observed for this product were in accord with those reported previously by Robins et al., Can. J. Chem., 55, 1259 (1977).

$^1$H-NMR (DMSO-$d_6$): 8.04 (s, 1H, H2) 7.33 (d, J=3.6, 1H, H8), 6.97 (broad s, 2H, $NH_2$), 6.56 (d, J=3.6, 1H, H7), 6.34 (dd, J=5.2 and 6.4, 1H, H1'), 4.96 (t, J=5.6, 1H, 5'0H) 4.33 (t, J=5.1, 0.43H, ethanol OH), 4.04 (m, 1H, H4'), 3.4–3.6 (m, 2.86H, H5' and ethanol $CH_2$), 2.33, 2.21 and 2.02 (m, 4H, H2' and H3'), and 1.06 (t, J=7.0, 1.3H, ethanol $CH_3$).

D. PREPARATION OF 7-IODO-2',3'-DIDEOXY-7-DEAZAADENOSINE (36)

A mechanically-stirred solution of 95% pure dideoxynucleoside 35 (2.95 g, 11.96 mmol), anhydrous sodium acetate (4.13 g, 50.3 mmol, 4 eg), and mercuric acetate (3.81 g, 11.95 mmol, 1.00 eq, Fisher, 99.9%) in water (190 mL) was heated under nitrogen at 65° for 2 hours. After cooling the resulting white suspension of mercurial to 25°. iodine (4.79 g, 18.9 mmol, 1.6 eq) and ethyl acetate (190 mL) were added. After 1 hour, the suspended mercurial had been consumed and a clear purple solution remained. After 2 hours, sodium sulfite (6.35 g) was added and the purple color disappeared. After stirring for 30 minutes, hydrogen sulfide gas was gently bubbled into the reaction for 15 minutes. Mercuric sulfide (a black colloid) and iodide 36 (a white powder) precipitated from the reaction. Complete precipitation of mercury(II) was assessed by TLC by monitoring the disappearence of one of the two major UV-active spots. The reaction mixture was filtered through filter aid and separated into two layers. The filter aid was washed with boiling ethyl acetate (9×100 mL) until TLC indicated that no further product was being extracted. Each ethyl acetate extract was washed with the aqueous layer. The combined ethyl acetate layers were dried over magnesium sulfate and evaporated to dryness. The resulting crude solid turned red upon exposure to air. This material was dissolved in 3:1 dichloromethane-methanol (100 mL) and the free base form of a weakly basic anion exchange resin (5.0 g, BioRad AG3 X4A, 2.9 meq/g dry) was added. Hydrogen sulfide was bubbled into the red solution for 10 minutes and the red color was discharged. A slight cloudiness was eliminated by briefly warming and the solution was rapidly filtered through a 2 cm plug (15 g) of silica gel. The silica gel was eluted with additional 3:1 dichloromethane-methanol (100 mL). Silica gel (50 g) was added to the filtrate and hydrogen sulfide was bubbled in for 10 minutes. The solvent was removed from this mixture with a rotary evaporator and the silica gel was "dried" by co-evaporating with chloroform (200 mL). This silica gel was rapidly loaded onto a silica gel column (500 g) which had been degassed with a stream of nitrogen. Elution under nitrogen with 5% (6 L) and 10% (4 L) methanol in dichloromethane afforded 2.92 g (64%) of iodide 36 as a white powder and 456 mg (7.5%) of less polar 7,8-diiodo-2',3'-dideoxy-7-deazaadenosine. Recrystallization of the major product from boiling ethyl acetate (200 mL) afforded 2.626 g of white needles (mp 158°–160°). Concentration of the mother liquors to 10 mL afforded a second crop of 0.391 g of light red needles (mp 156°–158°). Both crops were homogeneous according to NMR and TLC and together represent a 64% overall yield from olefin 34.

$^1$H-NMR (DMSO-$d_6$): 8.09 (s, 1H, H2), 7.67 (s, 1H, H8), 6.65, (broad s, 2H, NH$_2$), 6.34 (dd, J=4.4 and 6.8, 1H, H1'), 4.95 (t, J=5.5, 1H, 5'OH), 4.04 (apparent hept. J=3.5, 1H, H4'), 3.59 and 3.49 (m, 1H, H5'), 2.30, 2.28 and 2.00 (m, 4H, H2' and H3').

E. PREPARATION OF 7-(3-TRIFLUOROACETAMIDO-1-PROPYNYL)-2',3'-DIDEOXY-7-DEAZAADENOSINE (37)

Iodide 36 (720.3 mg, 2.00 mmol) was coupled for 90 minutes with N-propargyltrifluoroacetamide following the standard procedure given in Example 5C. Chromatography with 7% methanol in dichloromethane afforded 705.8 mg (92%) of coupling product 37 as an off white powder which was homogeneous according to NMR and TLC. Recrystallization from boiling ethyl acetate (10 mL) afforded 372 mg of white microcrystals (mp 169°–171°).

$^1$H-NMR (DMSO-$d_6$): 10.1 (distorted t, 1H, NHTFA), 8.10 (s, 1H, H2), 7.78 (s, 1H, H8), 6.0–7.5 (very broad s, NH$_2$), 6.34 (dd, J=4.5 and 7.0, 1H, H1'), 4.98 (t, J=5, 1H, 5'OH), 4.31 (slightly broadened s, 2H, —CH$_2$N—), 4.10 (apparent hept, J=3.5, 1H, H4'), 3.60, and 3.40 (m, 1H, H5'), 2.37, 2.18 and 2.00 (m, 4H, H2' and H3'). TLC (90:9:1 dichloromethane-methanol-concentrated ammonium hydroxide: UV): starting iodide 36, R$_f$=0.36; product 37, 0.26).

F. PREPARATION OF 7-(3-AMINO-1-PROPYNYL)-2',3'-DIDEOXY-7-DEAZAADENOSINE 5'-TRIPHOSPHATE (7-AP3-ddc7ATP)

Alkynylamino nucleoside 37 (1.00 mmol) was converted to the corresponding 5'-triphosphate and the trifluoroacetyl group was removed following the general procedure described in Example 5E. After addition of the second aliquot of phosphorus oxychloride the solution was stirred for 120 minutes. Assuming an absorption coefficient for the product equal to that of the starting material (12,700), the yield of 7-AP3-ddc7ATP, based on the absorption at 279.5 nm, was 40%.

$^1$H-NMR (D$_2$O): 7.97 (s, 1H, H2), 7.80 (s, 1H, H8), 6.33 (m, 1H, H1'), 4.44 (m, 1H, H4'), 4.27 (m, 1H, H5'a), 4.14 (m, 1H, H5'b), 4.11 (broad s, 2H, —CH$_2$—), 2.6–2.0 (m, 4H, H2' and H3'), plus counterion (triethylammonium) peaks. $^{31}$P-NMR (D$_2$O): –8.59 (broad d, J=20, 1P), –9.56 (d, J=20, 1P), and –21.38 (m, 1P). UV (pH 8.2 aq Tris): maxima at 238 and 279.5 nm.

EXAMPLE 9

General Coupling Procedure for Preparation of a Fluorescent-labeled Chain Terminator Preparation of a T-Terminator: 5-(SF-505-Sar-AP3) ddUTP The amine 5-(AP3)ddUTP (60 micromole) from Example 6C was taken up in water (0.300 mL) and diluted with DMF (0.600 mL). A solution of dye-labeling reagent Ac2EtSF-505-Sar-NHS-(72 mg, 126 micromole) from Example 1E in DMF (0.600 mL) was added and the mixture was stirred at 50° C. for 4 hours. Concentrated aqueous ammonia (1.5 mL) was added, the flask was tightly stoppered, and heating was continued at 50° C. for 20 minutes. The resulting red solution was diluted to 60 mL with water and applied to column of DEAE-Sephadex A-25-120 (1×35 cm bed) that had been equilibrated with 2.0M pH 7.7 aqueous TEAB (50 mL) and then 0.2M pH 7.7 aqueous TEAB (50 mL). The column was eluted with a linear gradient of pH 7.7 aqueous TEAB: 0.2M (150 mL)→2.0M (150 mL). The column was driven at 100 mL/hour collecting fractions every 3 minutes. The eluent was monitored by absorbance at 510 nm (40 AUFS). Two lesser by-product bands eluted first followed by the stronger product band with nearly baseline resolution. The fractions estimated to contain pure product were pooled, stripped down (T<30+ C.), coevaporated with absolute ethanol (3×), and taken up in a small volume (5.2 mL) of water. The solution was assayed by visible absorption (pH 8.2 50 mM aq Tris buffer) and lyophilized. A dilute solution of the product displayed an absorption maximum at 491 nm. The yield, calculated assuming the free dye absorption coefficient (72,600), was 31 micromoles (51%).

Additional fluorescent-labeled chain terminator compounds were prepared according to the general procedure disclosed. The nomenclature in Table 1 represents the fluorescent-labeled spacer (e.g. SF-512-Sar) and dideoxynucleotide-linker (AP3-ddNTP) materials which were prepared in the preceding examples and combined according to the general procedure to prepare new compositions useful in sequencing DNA.

TABLE 1

Summary of Data for Preparation of Other Fluorescent-labeled Chain Terminators
Summary of Data for Preparation of Other Terminators

| Compound | Scale | Column Gradient | Yield | AbsMax |
| --- | --- | --- | --- | --- |
| 5-(SF512-Sar-AP3)ddCTP | 40 umol | 0.4–0.7 M | 47% | 501 |
| 5-(SF519-Sar-AP3)ddCTP | 10 umol | 0.4–0.7 M | 27% | 508 |
| 7-(SF512-Sar-AP3)ddc7ATP | 10 umol | 0.4–0.7 M | 58% | 505.5 |
| 7-(SF526-Sar-AP3)ddc7GTP | 50 umol | 0.4–0.7 M | 53% | 519.5 |

TABLE 1-continued

Summary of Data for Preparation of
Other Fluorescent-labeled Chain Terminators
Summary of Data for Preparation of Other Terminators

| Compound | Scale | Column Gradient | Yield | AbsMax |
| --- | --- | --- | --- | --- |
| 5-(SF505-Sar-AP3)ddCTP | 10 umol | 0.4–0.7 M | 33% | 492 |
| 7-(SF505-Sar-AP3)ddc7GTP | 10 umol | 0.4–0.7 M | 42% | 497.5 |
| 5-(SF526-Sar-AP3)ddUTP | 7.5 umol | 0.4–0.7 M | 60% | 516.5 |
| 7-(SF512-Sar-AP3)ddc7GTP | 10 umol | 0.4–0.7 M | 60% | 505 |
| 5-(SF512-Sar-AP3)AcyCTP (acyclo) | 10 umol | 0.4–0.7 M | 54% | 500.5 |

EXAMPLE 10

Partial DNA Base Sequence of Bacteriophage M13
Using a Modified Sanger

Chain Elongation Protocol with
Fluorescent-Labeled Chain Terminators

A. Modified DNA Chain Elongation Reactions

A quantity of 3 μg bacteriophage M13 mp 18 DNA template (New England Biolabs; 0.25 μg/μL) and 60 μg (−40) primer (New England Biolabs; 7.5 μg/μL were dispensed into each of four 1.5 mL Eppendorf plastic tubes. Each tube was then heated for 2 minutes in a boiling water bath and immediately cooled on wet ice for 5 minutes. After a 1 second pulse-spin in a microcentrifuge at room temperature, μL of a 5× reaction buffer (0.3M Tris-HCl, pH 8.3; 0.375M NaCl; 37.5 mM $MgCl_2$; 2.5 dithiothreitol), 10 μL of reagent grade $H_2O$, 1 μL of a solution containing the triphosphates of adenosine, thymidine, cytosine, and guanosine at 25 μM each (Pharmacia), and 1 μL of reverse transcriptase (avian myeloblastosis virus: New England Nuclear; 15 units/μL), were added to each tube and mixed. The tubes were incubated at 37° C. for 10 minutes. Four μL of 200 μM solutions of the fluorescent-labeled chain terminators of Example 9 were added to the four tubes; one tube receiving 7-(SF505-Sar-AP3)ddc7GTP, another 7-(SF512-Sar-AP3)ddc7ATP, another 5-(SF519-Sar-AP3)ddCTP, and the fourth 5-(SF526-Sar-AP3)ddTTP. The tubes were incubated at 42° C. for 30 minutes. A mixture of 22 μL from each of the four tubes was prepared and passed through a 5–25 Select-D spin column (5 Prime→3 Prime; Philadelphia) which had been prewashed with reagent grade $H_2O$, to separate unincorporated fluorescent-labeled chain terminators from fluorescent-labeled, elongated strands of DNA in the reaction mixture. The column effluent was collected and vacuum dried. A 0.5 mL quantity of 70% ethanol was added and the tube vortexed for 5 seconds. The tube was then spun 5 minutes in a microcentrifuge, the DNA pellet vacuum dried, and resuspended with 10 μL 95% formamide-25 mM EDTA. The tube was heated to 65° C. for 7 minutes in a water bath, and 10 μL of the DNA sample micropipetted onto a preconditioned 8% polyacrylamide: bis (19:1) gel (15 cm×40 cm×0.35 mm) containing 8.3M urea and 1× TEAB buffer. The sample was electrophoresed at 27 watts as described in B below.

B. Fluorescent-Labeled DNA Strand Electrophoresis

Gel preconditioning consisted of exposing the gel to 27 watts continuous power (approximately 2000 volts) for about 30 minutes before the sample was loaded. During this period, the gel surface temperature stabilized at 49° C.

During the electrophoresis, the vertical gel was irradiated by an argon ion laser (Omnichrome Model 532, in a region 28 cm below the sample loading well. The laser was passed through a 488 nm line filter (Bart Associates), which excluded other wavelengths from entering the gel. Final laser power at the gel surface was 35 mW in an approximately 1 mm diameter.

Detection of fluorescent emissions from the fluorescent-labeled DNA strands was achieved by two photomultiplier tubes (PMT; Hamamatsu R1612) with a −950 volt bias each. Wavelength-selective filters (Barr Associates) were placed between the fluorescent emissions and the two PMT's, such that one filter associated with one PMT allowed emissions in the range 496 to 528 nm to pass, while the other filter associated with the second PMT allowed emissions in the range of 522 to 553 nm to pass. In addition, a fiber optic face plate (Incom) collecting aperture was placed in the light path between the fluorescent emissions and wavelength-selective filters to limit the half-angle of detection to below abut 22 degrees. The signals from each PMT were separately digitized after preamplification and data were obtained from both PMT's simultaneously every 5 seconds. The digitized data were stored in a sequential data file by the system controller (Hewlett-Packard 9000, Model 20).

C. Bacteriophage M13 Partial Sequence

The data derived from fluorescent emissions during electrophoresis of the fluorescent-labeled M13 mp 18 DNA strands were analyzed by known methods. A partial nucleoside sequence is shown in Table 2 for illustration.

TABLE 2

Partial Nucleoside Sequence of M13 mp 18

| Base Number | Nucleoside | Ratio (W) |
| --- | --- | --- |
| 3 | T | 0.14 |
| 4 | G | 0.90 |
| 5 | T | 0.19 |
| 6 | A | 0.78 |
| 7 | A | 0.75 |
| 8 | A | 0.80 |
| 9 | A | 0.75 |
| 10 | C | 0.35 |
| 11 | G | 1.88 |
| 12 | A | 0.89 |
| 13 | C | 0.32 |
| 14 | G | 1.88 |
| 15 | G | 1.92 |
| 16 | C | 0.33 |
| 17 | C | 0.36 |
| 18 | A | 0.81 |
| 19 | G | 1.89 |
| 20 | T | 0.16 |

The data clearly show that a narrow, distinct range of ratios were derived corresponding to each of the four nucleosides in M13 mp 18 DNA.

EXAMPLE 11

A. Preparation of 1-(2-Hydroxyethoxymethyl)-5-iodocytosine (5-IAcyC)

A mixture of 1-(2-hydroxyethoxymethyl) cytosine (AcyC) (1.85 g, 10.0 mmol) and mercuric acetate (3.35 g, 10.5 mmol) was refluxed in methanol (50 mL) and methylene chloride (100 mL). Iodine (3.05 g, 12.0 mmol) was added and the mixture stirred for 1 hour. The free base form of AG3×4 resin (38 meg) was added and the solution bubbled with hydrogen sulfide for 15 min. The solids were removed by filtration and the filtrate stripped down onto silica gel (10 g). The silica was loaded onto a silica gel column (4×25 cm) and eluted with a step gradient of methylene chloride/methanol (20:1→10:1→5:1). Evaporation followed by vacuum-drying afforded a colorless solid (1.73 g, 56%).

Recrystallization from 95% ethanol afforded analytically pure material. M.p: 172° C. Anal: Calc. [C(7)H(10)N(3)O(3)I(1)] C 27.03, H 3.24, N 13.51. Found: C 27.08, H 3.41, N 13.51. UV (MeOH): max 292.5 (5,300). NMR (DMSO-$d_6$): delta 3.481 (m, 4H), 4.659 (t, J=5 hz, 1H), 5.070 (s, 2H), 6.665 (bs, 1H), 7.869 (bs, 1H), and 8.107 (s, 1H).

B. Preparation of 1-(2-Hydroxyethoxymethyl)-5-(3-trifluoroacetamido-1-propynyl)cytosine (5-(TFA-AP3) AcyC)

1-(2-Hydroxyethoxymethyl)-5-iodocytosine (311 mg, 1.00 mmol) was subjected to the general coupling procedure disclosed in Example 5C. Flash chromatography on silica gel (3×20 cm) eluting with a step gradient of methylene chloride/methanol (20:1 →10:1→5:1) afforded the product as a pale yellow foam (77.4 mg, 23%)., $^1$H-NMR (DMSO-$d_6$): 3.472 (bs, 4H), 4.276 (d, J=5.0 hz, 2H), 4.653 (bt, J=4.5 hz, 1H), 5.091 (s, 2H), 6.925 (bs, 1H), 7861 (bs, 1H), 8.037 (s, 1H), and 9.964 (bs, 1H).

C. Preparation of 1-(2-hydroxyethoxymethyl)-5-(3-amino-1-propynyl)cytosine 5-triphosphate(5-AP3-AcyCTP)

The hydroxyl group of the sugar part of alkynylamino nucleoside (5-(TFA-AP3)AcyC) (0.167 mmol) was converted to a triphosphate and the trifluoroacetyl group was removed following the general procedure given in Example 5E. After addition of the second aliquot of phosphorus oxychloride, phosphorylation was allowed to proceed for 75 minutes. Assuming an absorption coefficient for the product equal to that of the starting material (7,790), the yield of triphosphate, based on its UV absorption at 291 nm, was 21%.

EXAMPLE 12

Preparation of a Thymidine Derivative Labeled with a Protected Dye ($R_1$=$R_2$=H)

A. Preparation of 5'-Deoxy-5'-(methyl-amino)-thymidine)

5'-O-(p-toluenesulfonyl)thymidine (19.8 g, 50 mmol) was placed in a pressure vessel into which monomethylamine (250 g) was condensed. The vessel was sealed and allowed to stand at room temperature for 3 days. The vessel was cooled, opened, and the monomethylamine allowed to evaporate. The remaining contents of the vessel were removed by rinsing with water. The aqueous solution was passed through a column (6.5×20 cm) of AG50W×8 ion-exchange resin (H+form). The column was washed with water until the washings were neutral. The product was then eluted with 1N aqueous ammonium hydroxide. The eluent was stripped down and the resulting solid chromatographed on a column (6.5×20 cm) of silica gel with methylene chloride/methanol/concentrated aqueous ammonium hydroxide (85:13:2) as the eluting solvent. The product containing fractions were stripped down, then taken up in water and lyophilized. The product was a pale-yellow, amorphous solid (8.81 g, 69%). A satisfactory combustion analysis could not be obtained for this material.) $[\alpha]_D^{25}$ (c=1.0 in water): +25.9 deg. ir (KBr): cm$^{-1}$ 1693, 1472, 1273, 1076. NMR (DMSO-$d_6$): δ1.790 (s, 3H), 2.051 (ddd, 13.4, 6.3, 3.5 hz, 1H), 2.142 (dr, 13.4, 6.9 hz, 1H), 2.314 (s, 3H), 2.658 (d, 5.5 hz, 2H), 3.775 (td, 5.3, 3.2 hz, 1H), 4.171 (dr, 6.3, 3.2 hz, 1H), 6.134 (t, 6.9 hz, 1H) and 7.639 (s, 1H).

B. Coupling

The product from Example 1B (4.14 g, 10.0 mmol), N-hydroxysuccinimide (1.21 g, 10.5 mmol), and N,N'-dicyclohexylcarbodiimide (3.09 g, 15.0 mmol) were stirred in dry methylene chloride (100 mL) at room temperature for 1 hour. The mixture was cooled in ice and the resulting precipitate removed by filtration. The residue was rinsed with 5 mL of chilled methylene chloride. The combined filtrates were added in a stream to a suspension of the product from (A). (2.68 g, 10.5 mmol) in absolute ethanol (300 mL). After stirring at room temperature for 90 minutes, the reaction mixture was stripped down, taken up in 100 mL of methylene chloride, and extracted with 2×100 mL of water. The organic layer was dried over sodium sulfate and stripped down. The residue was loaded onto a column (6.5×30 cm) of silica gel as a methylene chloride solution and the column was eluted with 20:1 methylene chloride/ethanol. The elution was monitored by thin layer chromatography on silica gel in 10:1 methylene chloride/methanol. Fractions containing pure product were retained while mixed fractions were rechromatographed. The combined solutions of pure product were stripped down and traces of solvent were removed by extensive vacuum drying to afford the product as a pale yellow, stiff foam (3.97 g, 61%). (A satisfactory combustion analysis could not be obtained for this amorphous solid.) $[\alpha]_D^{25}$ (c=0.96 in ethanol): +50.8°, ir (KBr): cm$^{-1}$ 1768, 1691, 1610, 1490, 1420, 1205 and 1150. FAB-MS (thioglycerol matrix) m/e 606 (M—CH$_3$CH$_2$O). NMR (DMSO-$d_6$): (Showed a 3:1 mixture of rotational isomers about the newly formed tertiary amide linkage). δ(major and minor) 1.038 (m, 3H), 1.780 and 1.800 (m, 2H), 1.78 (m, 2H), 2.04 (m, 2H), 2.23 (m, 2H), 2.291 (s, 6H), 2.683 and 2.711 (s, 3H), 2.895 and 2.859 (q, 6 hz, 2H), 3.5–3.2 (m, 2H), 3.805 and 3.57 (m, 1H), 4.032 and 3.98 (m, 1H), 5.249 and 5.295 (d, 3.6 hz, 1H), 6.116 and 6.012 (t, 6.9 hz, 1H), 7.1–6.9 (m, 4H), 7.467 and 7.185 (s, 1H), 7.6–7.5 (m, 2H) and 11.275 and 11.332 (s, 1H).

EXAMPLE 13

Preparation of a Protected, Dye ($R_1$=$R_2$=H)-Labeled Nucleoside Phosphoramidite The product from Example 11 (2.61 g, 4.00 mmol) was taken up in benzene, frozen, and lyophilized. Dry methylene chloride (32 mL), dry diisopropylethylamine (2.8 mL, 16 mmol) and N,N-diisopropyl methyl phosphonamidous chloride (1.15 mL, 5.9 mmol) were added in the order listed and the resulting mixture was stirred under an atmosphere of argon for 15 minutes. The reaction mixture was added to a preshaken mixture of ethyl acetate (160 mL) and saturated aqueous sodium bicarbonate (80 mL), shaken, and the layers separated. The organic layer was washed with 2×80 mL of saturated aqueous sodium chloride, dried over sodium sulfate, and stripped down. The residue was chromatographed on a column (4×20 cm) of silica gel with 45:45:10 methylene chloride/ethyl acetate/triethylamine as the eluting solvent. The eluent was monitored by thin layer chromatography on silica gel in the same solvent. The fractions containing product were stripped down and traces of solvent removed by extensive vacuum drying to afford the product as a pale yellow, stiff foam (2.89 g). The $^{31}$P NMR spectrum of the product showed a mixture of four products resulting from rotational isomerism about the tertiary amide linkage (6:1) and diastereomerism about the trivalent phosphorus (1:1). (The spectrum also revealed a 13 wt% contamination by N,N-diisopropyl methyl phosphonamidous acid. This material did not interfere in the use of the product for oligonucleotide synthesis.) Corrected yield: 77%. $^{31}$P NMR (CDCl$_3$): δ147.81 and 146.99 (s, major) and 148.18 and 147.75 (s, minor).

We claim:

1. A fluorescent-labeled triethylammonium salt having the structure:

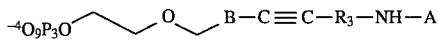

wherein B is uracil, cytosine, 7-deazaadenine, 7-deazaguanine, or 7-deazahypoxanthine; and A is a fluorophore having the structure:

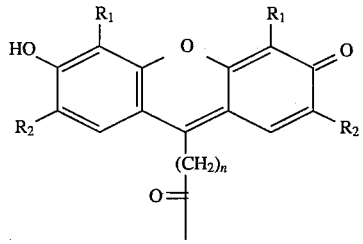

wherein n=2 or 3, and R$_1$ and R$_2$ are H, lower alkyl, halo, lower alkoxy, and cyano; and R$_3$ is a straight-chained C$_1$–C$_4$ alkylene moiety, provided that if B is a pyrimidine, B is N$_1$-linked to the acyclic sugar moiety and C$_5$-linked to one end of the triple bond (pyrimidine numbering), and if B is a 7-deazapurine, B is N$_9$-linked to the acyclic sugar moiety and C$_7$-linked to one end of the triple bond (purine numbering).

2. A fluorescent-labeled triethylammonium salt having the structure:

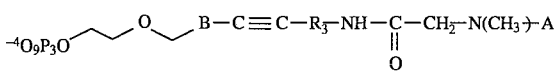

wherein B is uracil, cytosine, 7-deazaadenine, 7-deazaguanine, or 7-deazahypoxanthine; and A is a fluorophore having the structure:

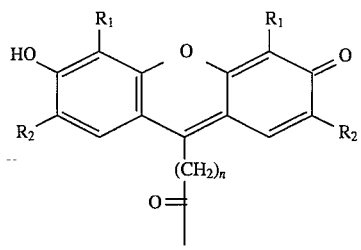

wherein n=2 or 3, and R$_1$ and R$_2$ are H, lower alkyl, halo, lower alkoxy, and cyano; and R$_3$ is a straight-chained C$_1$–C$_4$ alkylene moiety provided that if B is a pyrimidine, B is N$_1$-linked to the acyclic sugar moiety and C$_5$-linked to one end of the triple bond (pyrimidine numbering), and if B is a 7-deazapurine, B is N$_9$-linked to the acyclic sugar moiety and C$_7$-linked to one end of the triple bond.

3. The fluorescent-labeled triethylammonium salt of claim 2 wherein R$_3$ is CH$_2$.

* * * * *